United States Patent
Blitzer et al.

(10) Patent No.: US 10,350,178 B2
(45) Date of Patent: *Jul. 16, 2019

(54) METHODS AND COMPOSITIONS FOR TREATMENT OF DEMYELINATING DISEASES

(71) Applicant: Pathologica LLC, San Francisco, CA (US)

(72) Inventors: Jeremy Blitzer, San Francisco, CA (US); John McKearn, St. Louis, MO (US)

(73) Assignee: Pathologica LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,824

(22) Filed: Aug. 23, 2018

(65) Prior Publication Data
US 2018/0360783 A1 Dec. 20, 2018

Related U.S. Application Data

(63) Continuation of application No. 14/759,599, filed as application No. PCT/US2014/010714 on Jan. 8, 2014, now Pat. No. 10,085,955.

(60) Provisional application No. 61/823,276, filed on May 14, 2013, provisional application No. 61/750,336, filed on Jan. 8, 2013.

(51) Int. Cl.
A61K 31/15 (2006.01)
A61K 31/137 (2006.01)
A61K 38/03 (2006.01)
A61K 38/21 (2006.01)
A61K 31/136 (2006.01)
A61K 31/155 (2006.01)
A61K 31/225 (2006.01)
A61K 31/277 (2006.01)
A61K 31/4704 (2006.01)
A61K 9/00 (2006.01)

(52) U.S. Cl.
CPC .......... A61K 31/15 (2013.01); A61K 9/0053 (2013.01); A61K 31/136 (2013.01); A61K 31/137 (2013.01); A61K 31/155 (2013.01); A61K 31/225 (2013.01); A61K 31/277 (2013.01); A61K 31/4704 (2013.01); A61K 38/03 (2013.01); A61K 38/21 (2013.01)

(58) Field of Classification Search
None
See application file for complete search history.

(56) References Cited

U.S. PATENT DOCUMENTS

| | | |
|---|---|---|
| 4,201,788 A | 5/1980 | Voorhees |
| 4,520,031 A | 5/1985 | Knight, III |
| 5,580,715 A | 12/1996 | McGrath |
| 5,614,557 A | 3/1997 | Bey |
| 5,639,600 A | 6/1997 | McGrath |
| 5,744,122 A | 4/1998 | McGrath |
| 6,169,115 B1 | 1/2001 | Kaddurah-Daouk |
| 6,537,523 B1 | 3/2003 | McGrath |
| 6,544,541 B1 | 4/2003 | Zahradka |
| 6,924,095 B2 | 8/2005 | McGrath |
| 7,087,648 B1 | 8/2006 | McGrath |
| 7,198,946 B2 | 4/2007 | Marton |
| 7,445,794 B1 | 11/2008 | Newell |
| 7,754,765 B2 | 7/2010 | Wang |
| 7,879,914 B2 | 2/2011 | McGrath et al. |
| 8,258,186 B2 | 9/2012 | McKearn et al. |
| 8,445,540 B2 | 5/2013 | Hadlock et al. |
| 8,609,734 B2 | 12/2013 | McKearn et al. |
| 8,858,991 B2 | 10/2014 | McKearn |
| 9,668,988 B2 | 6/2017 | McKearn |
| 9,675,566 B2 | 6/2017 | McKearn |
| 9,867,794 B2 | 1/2018 | Hadlock |
| 10,292,950 B2 | 5/2019 | McKearn |
| 2003/0130357 A1 | 7/2003 | Ramesh |
| 2003/0175832 A1 | 9/2003 | Marton |
| 2004/0219208 A1 | 11/2004 | Kawamura |
| 2005/0042277 A1 | 2/2005 | Srinivas |
| 2005/0159493 A1 | 7/2005 | McGrath |
| 2005/0256207 A1 | 11/2005 | McGrath |
| 2006/0160087 A1 | 7/2006 | McGrath |
| 2007/0078187 A1 | 4/2007 | McGrath |
| 2008/0262092 A1 | 10/2008 | Hadlock |
| 2009/0017114 A1 | 1/2009 | Heasley |
| 2009/0181089 A1 | 7/2009 | Schellekens |

(Continued)

FOREIGN PATENT DOCUMENTS

CN 101300004 A 11/2008
EP 1389480 A1 2/2004

(Continued)

OTHER PUBLICATIONS

U.S. Appl. No. 15/441,122; Non-Final Office Action dated Sep. 13, 2018; 37 pages.

(Continued)

Primary Examiner — Heidi Reese
(74) Attorney, Agent, or Firm — Dennis A. Bennett; Cynthia Hathaway; Clifford A. Schlecht

(57) ABSTRACT

Disclosed herein is a method of prevention of progression of a multiple sclerosis in a patient, comprising the administration of methylglyoxal bis(guanylhydrazone) (MGBG) to the patient in need thereof. Also disclosed herein is a method of prevention or reduction in severity of the initiation phase of autoimmune response in a patient having multiple sclerosis, comprising the administration of MGBG to the patient in need thereof.

19 Claims, 17 Drawing Sheets

(56) References Cited

U.S. PATENT DOCUMENTS

| | | |
|---|---|---|
| 2010/0189790 A1 | 7/2010 | Safadi |
| 2011/0091418 A1 | 4/2011 | McGrath |
| 2011/0112199 A1 | 5/2011 | McKearn |
| 2012/0219970 A1 | 8/2012 | McGrath |
| 2012/0269891 A1 | 10/2012 | McKearn |
| 2012/0289604 A1 | 11/2012 | McKearn |
| 2014/0051765 A1 | 2/2014 | McKearn |
| 2014/0187643 A1 | 7/2014 | McKearn |
| 2014/0377345 A1 | 12/2014 | McKearn |
| 2015/0359761 A1 | 12/2015 | Blitzer |
| 2017/0290788 A1 | 10/2017 | McKearn |
| 2018/0050000 A1 | 2/2018 | McKearn |
| 2018/0369170 A1 | 12/2018 | McKearn |

FOREIGN PATENT DOCUMENTS

| | | |
|---|---|---|
| EP | 2283830 A1 | 2/2011 |
| EP | 2343075 A1 | 7/2011 |
| JP | 2008112659 | 5/2008 |
| WO | 1996021450 A2 | 7/1996 |
| WO | 1999021542 A2 | 5/1999 |
| WO | 2000074742 A1 | 12/2000 |
| WO | 200160392 A1 | 8/2001 |
| WO | 03089601 A2 | 10/2003 |
| WO | 2004089341 A1 | 10/2004 |
| WO | 2005041988 A1 | 5/2005 |
| WO | 2006081431 | 8/2006 |
| WO | 2006091522 A2 | 8/2006 |
| WO | 2007016338 A2 | 2/2007 |
| WO | 2007035957 A2 | 3/2007 |
| WO | 2008112656 | 9/2008 |
| WO | 2008112659 A2 | 9/2008 |
| WO | 2009018368 | 2/2009 |
| WO | 2010037395 A2 | 4/2010 |
| WO | 2010045265 A1 | 4/2010 |
| WO | 2010066203 A1 | 6/2010 |
| WO | 2011009039 | 1/2011 |
| WO | 2011009039 A2 | 1/2011 |
| WO | 2011080344 | 7/2011 |
| WO | 2012100043 A2 | 7/2012 |
| WO | 2014110154 A1 | 7/2014 |

OTHER PUBLICATIONS

U.S. Appl. No. 15/583,697; Advisory Action, dated Oct. 5, 2018; 19 pages.

U.S. Appl. No. 15/594,199; Non-Final Office Action, dated Oct. 26, 2018; 32 pages.

Dal Canto, M. et al., "Two Models of Multiple Sclerosis: Eperimental Allergic Encephalomyelitis (EAE) and Theiler's Murine Encephalomyelitis Virus (TMEV) Infection. A Pathological and Immunological Comparison", Microsc Res Tech., 32(3):215-29, (1995).

Kapoor, S., "Osteopontin: A Major Player in the Pathogenesis of Endocrine and Systemic Diseases", Endocr J., 55 (4):785, (2008).

Racke, M. et al., "Nuclear Receptors and Autoimmune Disease: The Potential of PPAR Agonists to Treat Multiple Sclerosis", J Nutr., 136(3):700-3, (2006).

Steinman, L. et al., "New Targets for Treatment of Multiple Sclerosis", J Neurol Sci., 274(1-2):1-4, (2008).

U.S. Appl. No. 15/594,199; Notice of Allowance dated Jan. 17, 2019; 17 pages.

"Fingolimod", Wikipedia, Available from the Internet, <URL: https://en.wikipedia.org/w/index.php?title=Fingolimod&oldid=524066559>, Last Retrieved Oct. 12, 2017, Published Nov. 20, 2012 according to Wikipedia.

Ackerman, J. et al., "Drugs Affecting the Cell Cycle via Actions on the Polyamine Metabolic Pathway", Progress in Cell Cycle Res. 5, 461-468, (2003).

Aher, et al., "Formulation Optimization and Pharmacokinetic Studies of an Enteric Coated Sustained Release Mucoadhesive Tablet of Zaltoprofen," Am. J. PharmTech Res., 4(4):133-62, (2014).

Allan, A. et al., "Role of the Integrin-Binding Protein Osteopontin in Lymphatic Metastasis of Breast Cancer", American Journal of Pathology, 169(1):233-246, (2006).

Allen, LV et al., Ansel's Pharmaceutical Dosage Forms and Drug Delivery Systems, 8th Edition, 1995, Lippincott Williams & Wilkins, Media, PA, pp. 260, 262 and 268-271.

Ang, C. et al., "Plasma Osteopontin Levels are Predictive of Disease Stage in Patients With Transitional Cell Carcinoma of the Bladder", BJU Int., 96:803-5, (2005).

Anonymous, "Cancer Chemotherapy Reports", JNCI: J Natl Cancer Inst, 22(2):441, (Feb. 1959).

Anonymous, "Naproxen Delayed Release", Drugs.com webpage at https://www.drugs.com/pro/naproxen-delayed-release.html, accessed Jul. 14, 2018; 33 pages, (2017).

Banerjee, S. et al., "Gene Expression Profiling in Inflammatory Airway Disease Associated With Elevated Adenosine", American Journal of Physiology Lung Cellular and Molecular Physiology, 282:169-82, (2002).

Bao, L. et al., "Osteopontin in Metastatic Lesions as a Prognostic Marker in Ovarian Cancers", Journal of Biomedical Science, 14:373-81, (2007).

Birnbaum, G., "Long-Term Disease-Modifying Therapies", Multiple Sclerosis, Ch. 8:1-18, (Feb. 2009).

Bitonti et al., Characterization of Trypanosoma brucei brucei S-adenosyl-L-methionine decarboxylase and its inhibition by Berenil, pentamidine and methylglyoxal bis(guanylhydrazone). Biochem J. 237(3): 685-9 (1986).

Boeshore, K. et al., Novel Changes in Gene Expression Following Axotomy of a Sympathetic Ganglion: A Microarray Analysis, J Neurobiol. 59, 216-235, 2004.

Bonvini, JM et al., Lack of In Vivo Function of Osteopontin in Experimental Anti-GBM Nephritis, J Am Soc Nephrol. 11, 1647-1655, 2000.

Bramwell et al., Serial plasma osteopontin levels have prognostic value in metastatic breast cancer. Clin Cancer Res. 12(11 Pt 1):3337-43 (2006).

Brown , L. et al., Osteopontin Expression and Distribution in Human Carcinomas, Am J Pathol 145(3), 610-623,1994.

Bruemmer, D. et al., Angiotensin II-Accelerated Atherosclerosis and Aneurysm Formation is Attenuated in Osteopontin-Deficient Mice, J Clin Invest. 112(9), 1318-1331, 2003.

Chabas D et al., 'The Infuence of the Proinfammatory Cytokine, Osteopontin, on Autoimmune Demyelinating Disease,' Science, Nov. 23, 2001 294(5547): 1731-5.

Chambers, A. et al., Osteopontin Expression in Lung Cancer, Lung Cancer 15, 311-323, 1996.

Chiocchetti, A. et al., High Levels of Osteopontin Associated with Polymorphisms in its Gene are a Risk Factor for Development of Autoimmunity/Lymphoproliferation, Blood 103(4), 1376-1382, 2004.

Coppola D et al., Correlation of osteopontin protein expression and pathological stage across a wide variety of tumor histologies. Clin Cancer Res. 10(1 Pt 1):184-90 (2004).

Cronstein, B., Low-Dose Methotrexate: A Mainstay in the Treatment of Rheumatoid Arthritis, Pharm Revs. 57(2), 163-172, 2005.

Della Ragione, F. et al., Effect of Analogues of 5'-Methylthioadenosine on Cellular Metabolism, Biochem J. 210, 429-435, 1983.

Denhardt, D. et al., Role of Osteopontin in Cellular Signaling and Toxicant Injury, Annu Rev Pharmacol Toxicol. 41, 723-749, 2001.

Dunzendorfer, U., Some aspects of clearance of mitoguazone in cancer patients and experimental cancer models, Arzneimittel-Forschung (1986), 36(3), 506-8 CODEN: ARZNAD; ISSN: 0004-4172.

Dutta, S. et al., "Distinct Absorption Characteristics of Oral Formulations of Valproic Acid/Divalproex Available in the United States", Epilepsy Res., 73(3):275-83, (2007).

Ekelund, S. et al., Guanidino-Containing Drugs in Cancer Chemotherapy: Biochemical and Clinical Pharmacology, Biochem Pharmacol. 61, 1183-1193, 2001.

EP 2121586 Extended European Search Report, dated Jul. 22, 2011, 27 pages.

EP 2453886 Extended European Search Report, dated Nov. 5, 20125, 7 pages.

(56) References Cited

OTHER PUBLICATIONS

Fedarko, N. et al., Elevated Serum Bone Sialoprotein and Osteopontin in Colon, Breast, Prostate, and Lung Cancer, Clin Cancer Res. 7, 4060-4066, 2001.
Fischer D et al., A role for adenosine deaminase in human monocyte maturation, J Clin Invest. 58(2):399-407 (1976).
Freedlander, B.L., Carcinostatic Action of Polycarbonyl Compounds and Their Derivatives II. Glyoxal Bis (Guanylhydrazone) and Derivatives, Cancer Research, 18(4):360-3, (Apr. 1958).
Freedlander, B.L., Carcinostatic Action of Polycarbonyl Compounds and Their Derivatives III. Hydroxymethylglyoxal Bis(guanylhydrazone), Cancer Research, 18(12):1286-9, (Dec. 1958).
Freireich, E. et al., Methylglyoxal Bis (Guanylhydrazone): A New Agent Active Against Acute Myelocytic Leukemia, Cancer Chemotherapy Reports 16, 183-186, 1962.
Furger, K. et al., The Functional and Clinical Roles of Osteopontin in Cancer and Metastasis, Curr Mol Med. 1(5), 321-632, 2001.
Giannessi, F. "Carnitine Palmitoyltransferase Inhibitors in the Management of Type 2 Diabetes: An Old Promise to be Maintained", Drugs of the Future, Prous Science, ES, 28(4):371-81, (Apr. 1, 2003).
Guo X et al., 'Spermidine alleviates severity of murine experimental autoimmune encephalomyelitis,' Invest Ophthalmol Vis Sci, Apr. 1, 2011, 52(5): 2696-703.
Hadjimichael, O. et al., Persistent Pain and Uncomfortable Sensations in Persons With Multiple Sclerosis, Pain 127, 35-41, 2007.
Harth, M. et al., Monocyte Dependent Excited Oxygen Radical Generation in Rheumatoid Arthritis: Inhibition by Gold Sodium Thiomalate, J Rheumatol 10(5), 701-707, 1983.
Hasko G et al., Shaping of monocyte and macrophage function by adenosine receptors. Pharmacol Ther. 113 (2):264-75 (2007, e-published Sep. 2006).
Herr, H. et al., Phase 1 Trial of Alpha-Difluoromethyl Ornithine (DFMO) and Methylglyoxal Bis (Guanylhydrazone) MGBG) in Patients With Advanced Prostatic Cancer, Urology 28(6), 508-511, 1986.
Hershfield, M., New Insights Into Adenosine-Receptor-Mediated Immunosuppression and the Role of Adenosine in Causing the Immunodeficiency Associated With Adenosine Deaminase Deficiency, Eur J Immunol. 35, 25-30, 2005.
Hibasami, H. et al., Studies of Inhibition of Rat Spermidine Synthase and Spermine Synthase, Biochem J. 187, 419-428, 1980.
Holland, J. et al., "Growth Inhibitors of Transplanted Rodent Tumors by Glyoxal-bis-guanylhydrazones", Cancer Research (Suppl. ), 21: No. 3, Part 2, pp. 15-26, 1961.
Howden, "Review Article: Immediate-Release Proton-Pump Inhibitor Therapy—Potential Advantages", Alimentary Pharmacol. Therapeutics, 22(Suppl. 3):25-30, (2005).
Huang, Y. et al., Molecular Mechanisms of Polyamine Analogs in Cancer Cells, Anti-Cancer Drugs 16, 229-241, 2005.
Hur, EM et al., Osteopontin-Induced Relapse and Progression of Autoimmune Brain Disease Through Enhanced Survival of Activated T Cells, Nature Immunol. 8(1), 74-83, 2007.
International Application No. PCT/US2014/010714; International Preliminary Report on Patentability, dated May 2, 2014; 6 pages.
International Application No. PCT/US2014/010714; International Search Report and Written Opinion of the International Search Authority, dated May 2, 2014; 11 pages.
Jensen, B., Dialyzability of Methyl Glyoxal Bis Guanyl Hydrazone, Cancer Treatment Reports, (1983) vol. 67, No. 3, pp. 283-284. CODEN: CTRRDO. ISSN: 0361-5960.
Kaczmarek L et al., Inhibitors of polyamine biosynthesis block tumor necrosis factor-induced activation of macrophages. Cancer Res 52:1891-4 (1992).
Kamatani N et al., Dependence of adenine production upon polyamine synthesis in cultured human lymphoblasts. Biochim Biophys Acta. 675(3-4):344-50 (1981).
Kaminska et al., Pretreatment serum levels of cytokines and cytokine receptors in patients with non-small cell lung cancer, and correlations with clinicopathological features and prognosis. M-CSF—an independent prognostic factor. Oncology. 70(2):115-25 (2006).
Kawamura, K. et al., Differentiation, Maturation, and Survival of Dendritic Cells by Osteopontin Regulation, Clin Diagn Lab Immunol. 12(1), 206-212, 2005.
Kelsen, D. et al., Phase II Trials of Methylglyoxal-bis (Guanylhydrazone), Am J Clin Oncol 5, 221-225, 1982.
Khan, G., "Controlled Release Oral Dosage Forms: Some Recent Advances in Matrix Type Drug Delivery Systems," The Sciences 1(5), 350-354, 2001.
Khan, M. et al., "A pH-dependent colon targeted oral drug delivery system using methacrylic acid copolymers. I. Manipulation Of drug release using Eudragit L100-55 and Eudragit S100 combinations", J Control Release., 58(2):215-22, (1999).
Kim JH et al., Osteopontin as a potential diagnostic biomarker for ovarian cancer. JAMA. 287(13):1671-9 (2002).
Kim, Y. et al., "Preparation and Evaluation of Enteric-Coated Delayed-Release Pellets of Duloxetine Hydrochloride Using a Fluidized Bead Coater", Archives of Pharmacol. Res., 38(12):2163-71, (2015).
Knight, W.A. III et al., "Phase I-II trial of methyl-GAG: a Southwest Oncology Group Pilot Study," Cancer Treat Rep. 63 (11-12):1933-7 (1979).
Levin, Robert H., Different patterns of remission in acute myelocytic leukemia. A comparison of the effects of the methylglyoxal bis(guanylhydrazone) and 6-mercaptopurine, Blood (1963), 21, 689-98 CODEN: BLOOAW; ISSN: 0006-4971.
Liaw L et al., Altered wound healing in mice lacking a functional osteopontin gene (spp1). J Clin Invest. 101(7):1468-78 (1998).
Licht, D. et al., "Is it Possible to Achieve Bio-Equivalence Between an Oral Solid Immediate-Release and an Analogue Enteric-Coated Formulation?", J. Pharmacy and Pharmacol., 68(10):1278-89, (2016).
Lieber, C. et al., S-Adenosylmethionine: Molecular, Biological, and Clinical Aspects—An Introduction, Am J Clin Nutr 76(suppl), 1148S-1150S, 2002.
Liesmann, J. etal., Pharmacokinetics of Methyl-Gloxyl Bis-Guanylhydrozone (MGBG), AACR Abstracts 605, 151, 1980.
Lim, S. W. et al., "MGBG Therapy of Relapsed Extralymphatic HIV-Associated Non-Hodgkin's Lymphoma (HIV NHL)", Proceedings, American Society of Clinical Oncology, Meeting, Waverly Press, Baltimore, MD, US, 14:A1274, (Mar. 1, 1995).
Maddox, A.M., Polyamines increase in human peripheral blood and bone marrow mononuclear cells following administration of methylglyoxal bis(guanylhydrazone), Chemotherapy, (1988) vol. 34, No. 5, pp. 419-429. Journal code: 0144731. ISSN: 0009-3157.
Manni, A. et al., "Cellular mechanisms mediating the anti-invasive properties of the ornithine decarboxylase inhibitor [alpha]-difluoromethylornithine (DFMO) in human breast cancer cells", Clinical & Experimental Metastasis ; Official Journal of the Metastasis Research Society, Kluwer Academic Publishers, DO, 21(5):461-7, (May 24, 2004).
Marton, et al., 'Polyamines as Targets for Therapeutic Intervention.' Ann. Rev. Pharm. Toxicol., vol. 35, 55-91, (1995).
Matsui, Y. et al., Osteopontin Deficiency Attenuates Atherosclerosis in Female Apolipoprotein E-Deficient Mice, Arterioscler Thromb Vase Biol. 23, 1029-1034, 2003.
Maubec et al., 'Subcutaneous Inflammatory Edema Induced by MINE Chemotherapy', Annales de dermatologie et de venerologie, vol. 128, No. 4, pp. 534-537 (Apr. 2001). See enclosed translated abstract.
Mazzali, M. etal., Osteopontin—A Molecule for All Seasons, QJM 95, 3-13, 2002.
Messina, L. et al., Polyamine Involvement in Functional Activation of Human Macrophages, J Leukoc Biol. 52, 585-587, 1992.
Mezzano et al., Overexpression of chemokines, fibrogenic cytokines, and myofibroblasts in human membranous nephropathy. Kidney Int. 57(1):147-58 (2000).
Mi, Zhiyong et al., Differential osteopontin expression in phenotypically distinct subclones of murine breast cancer cells mediates metastatic behavior. J Biol Chem. 279(45): 46659-67 (2004).
Mihich, E. et al., Pharmacology of Methylglyoxal-bis-(guanylhydrazone) (CH3-G) I. Toxic and Pathologic Effects, Cancer Res, (1962) vol. 22, Sep. (No. 9) pp. 962-972 (plus figs).

(56) References Cited

OTHER PUBLICATIONS

Mihich, E., Anti-Tumor Effects and Toxicology of Methylglyoxal Bis (Guanylhydrazone), Proc. Nat. Acad. Sciences Abstracts 1959.
Mihich, Enrico, Current Studies with Methylglyoxal-bis(guanylhydrazone), Cancer Res, (1963) vol. 23, Sep. (No. 9) pp. 1375-1389.
Mitoguazone, "Drugs of the Future," 1992 ES, (1992), vol. 17, No. 3, ISSN 0377-8282, pp. 253-254, XP009190054.
Mor G et al., Serum protein markers for early detection of ovarian cancer. Proc Natl Acad Sci USA. 102(21):7677-82 (2005).
Nemir, M. et al., Targeted Inhibition of Osteopontin Expression in the Mammary Gland Causes Abnormal Morphogenesis and Lactation Deficiency, J Biol Chem. 275(2), 969-976, 2000.
Noiri E, et al. Reduced tolerance to acute renal ischemia in mice with a targeted disruption of the osteopontin gene. Kidney Int. 56(1):74-82 (1999).
NZ 597488 Examination Report, dated Aug. 8, 2012, 2 pages.
Oates et al., The identification of osteopontin as a metastasis-related gene product in a rodent mammary tumour model. Oncogene. 13(1):97-104 (1996).
Ohmori R et al., Plasma osteopontin levels are associated with the presence and extent of coronary artery disease. Atherosclerosis. 170(2):333-7 (2003).
Okada H et al., Tubular osteopontin expression in human glomerulonephritis and renal vasculitis. Am J Kidney Dis. 36 (3):498-506 (2000).
Oliverio, V. et al., The Distribution, Excretion, and Metabolism of Methylglyoxal-Bis-Guanylhydrazone-C14, Clin Pharmacol and Experimental Thera Ser. 141, 149-156, 1963.
Panzer U et al., Monocyte chemoattractant protein-1 and osteopontin differentially regulate monocytes recruitment in experimental glomerulonephritis. Kidney Int. 59(5):1762-9 (2001).
Pelleteir, D. et al., "Fingolimod for Multiple Sclerosis," New Eng. J. Med. 2012 vol. 366 pp. 339-347.
Pixley et al., CSF-1 regulation of the wandering macrophage: complexity in action. Trends Cell Biol. 14(11):628-38 (2004).
Pixley, F. et al., Protein Tyrosine Phosphatase Phi Regulates Paxillin Tyrosine Phosphorylation and Mediates Colony-Stimulating Factor 1-Induced Morphological Changes in Macrophages, Mol Cell Biol. 21(5), 1795-1809, 2001.
Regelson, William, Clinical experience with methylglyoxal bis(guanylhydrazone) dihydrochloride: A new agent with clinical activity in acute myelocytic leukemia and the lymphomas., Cancer Chemother Repts, (1963) vol. 27, pp. 15-26.
Regelson, William, Initial clinical study of parenteral methylglyoxal bis(guanylhydrazone) diacetate, Cancer Chemother Repts, (1961) vol. 11, pp. 81-86.
Regenass U et al., CGP 48664, A new S-adenosylmethionine decarboxylase inhibitor with broad spectrum antiproliferative and antitumor activity. Cancer Res. 54(12):3210-3217 (1994).
Renkl et al., Osteopontin functionally activates dendritic cells and induces their differentiation toward a Th1-polarizing phenotype. Blood. 106(3):946-55 (2005).
Rittling SR et al., Osteopontin function in pathology: lessons from osteopontin-deficient mice. Exp Nephrol. 7(2):103-13 (1999).
Roach, H., "Arthritis & Rheumatism," 2008, Journal of the American College of Rheumatology, 58(8), pp. 2217-2218.
Rudland et al., Prognostic significance of the metastasis-associated protein osteopontin in human breast cancer. Cancer Res. 62(12):3417-27 (2002).
Sakaguchi H et al., Clinical implications of osteopontin in metastatic lesions of uterine cervical cancers. Cancer Lett. 247(1):98-102 (2007).
Salvi, M. et al., The Effect of Methylglyoxal-Bis (Guanylhydrazone) on Mitochondrial Ca2+ Fluxes, Biochem Pharmacol. 63, 247-250, 2002.
Sato T et al., Osteopontin/Eta-1 upregulated in Crohn's disease regulates the Th1 immune response. Gut. 54 (9):1254-62 (2005).

Schilling, S. et al., "Fumaric Acid Esters are Effective in Chronic Experimental Autoimmune Encephalomyelitis and Suppress Macrophage Infiltration", Clin. Exp Immunol. 145(1):101-7, (Jul. 2006).
Seiler N et al., Polyamines and apoptosis. J Cell Mol Med. 9(3):623-642, 2005 J Cell Mol Med. Jul.-Sep. 2005; 9(3): 623-42.
Sherr et al., The FMS gene and the CSF-1 receptor. Cancer Surv. 5(2): 221-32 (1986).
Shevde LA et al., Osteopontin knockdown suppresses tumorigenicity of human metastatic breast carcinoma, MDA-MB-435. Clin Exp Metastasis 23(2): 123-33 (2006).
Siimes, M., Synergistic Action of 2 Polyamine Anti Metabolites leads to a Rapid Therapeutic Response in Childhood Leukemia, International Journal of Cancer, (1981) vol. 28, No. 5, pp. 567-570. CODEN: IJCNAW. ISSN: 0020-7136.
Simon M.S. et al., 'Phase II trial of methylglyoxal bis-guanylhydrazone (MGBG) in refractory small cell lung cancer', Investigational New Drugs, Martinus Nijhoff Publishers, Boston, US, (Jan. 1, 1990), vol. 8, ISSN 0167-6997, pp. S79-S81, XP008169410.
Singh, R. et al., Definition of a Specific Interaction Between the Early T Lymphocyte Activation 1 (Eta-1) Protein and Murine Macrophages in Vitro and its Effects Upon Macrophages in Vivo, J Exp Med. 171, 1931-1942, 1990.
Standal T et al., Role of osteopontin in adhesion, migration, cell survival and bone remodeling. Exp Oncol. 26(3): 179-84 (2004).
Takahashi F et al., Osteopontin is induced by nitric oxide in RAW 264.7 cells. IUBMB Life. 49: 217-221 (2000).
Takami, H., Experimental chronochemotherapy with methylglyoxal bis-(guanylhydrazone) (methyl-GAG), Proceedings of the American Association for Cancer Research, (1981) vol. vol. 22, pp. 882. CODEN: PAACA3.
Thiele, J. et al., Condensation Products of Aminoguanidine With Aldehydes and Ketones of the Aliphatic Series, Annalen Der Chemie 302, 275-299, 1898.
Thompson, H. et al., "History, Literature, and Theory of Enteric Coatings," 2006; Journal of the American Pharmaceutical Association, 34(5):135-138.
Tong, A. et al., "The Pathology of Atopic Dermatitis," 1986, Clin. Rev. Allergy, 4, pp. 27-42.
Tushinski RJ et al., The regulation of mononuclear phagocyte entry into S phase by the colony stimulating factor CSF-1. J Cell Physiol. 122(2): 221-8 (1985).
U.S. Appl. No. 12/837,753; First Action Interview—office action dated Apr. 27, 2012; 2 pages.
U.S. Appl. No. 13/865,816; Affidavit-traversing rejections or objections rule 132 dated Jan. 27, 2017; 28 pages.
U.S. Appl. No. 13/865,816; First Action Interview—office action dated Oct. 2, 2015; 3 pages.
U.S. Appl. No. 13/865,816; Notice of Allowance dated Sep. 12, 2017; 9 pages.
U.S. Appl. No. 14/033,738; Notice of Allowance dated Feb. 13, 2017; 6 pages.
U.S. Appl. No. 14/033,738; Notice of Allowance dated Feb. 28, 2017; 4 pages.
U.S. Appl. No. 14/063,541; Notice of Allowance dated Nov. 23, 2016; 8 pages.
U.S. Appl. No. 14/458,919; Non-Final Office Action dated May 12, 2017; 13 pages.
U.S. Appl. No. 14/480,847; Examiner Initiated Interview Summary dated Jan. 30, 2017; 2 pages.
U.S. Appl. No. 14/480,847; Non-Final Office Action dated Jun. 28, 2016; 15 pages.
U.S. Appl. No. 14/480,847; Notice of Allowance dated Jan. 30, 2017; 8 pages.
U.S. Appl. No. 14/759,599; Non-Final Office Action dated Jun. 6, 2016; 7 pages.
U.S. Appl. No. 14/759,599; Final Office Action dated Feb. 27, 2017; 6 pages.
U.S. Appl. No. 14/759,599; Non-Final Office Action dated Oct. 5, 2017; 8 pages.
U.S. Appl. No. 14/759,599; Notice of Allowance dated May 21, 2018; 7 pages.
U.S. Appl. No. 15/583,697; Applicant-Initiated Interview Summary dated Jul. 13, 2018, 2 pages.

(56) References Cited

OTHER PUBLICATIONS

U.S. Appl. No. 15/583,697; Final Office Action dated Jun. 28, 2018; 24 pages.
U.S. Appl. No. 15/583,697; Non-Final Office Action dated Mar. 2, 2018; 11 pages.
U.S. Appl. No. 13/865,816, Applicant-Initiated Interview Summary, dated Feb. 8, 2016, 3 pages.
U.S. Appl. No. 14/033,738, Examiner-Initiated Interview Summary, dated May 11, 2016, 1 page.
U.S. Appl. No. 14/033,738, Final Office Action, dated Sep. 15, 2015, 11 pages.
U.S. Appl. No. 14/033,738, Non-Final Office Action, Apr. 17, 2015, 13 pages.
U.S. Appl. No. 14/063,541, Affidavit-Traversing Rejections or Objections Rule 132, Nov. 5, 2015, 28 pages.
U.S. Appl. No. 14/063,541, Applicant-Initiated Interview Summary, Dec. 16, 2014, 3 pages.
U.S. Appl. No. 14/063,541, Final Office Action, dated May 5, 2015, 7 pages.
U.S. Appl. No. 14/063,541, Non-Final Office Action, Dec. 27, 2013, 8 pages.
U.S. Appl. No. 14/063,541, Non-Final Office Action, Aug. 14, 2014, 6 pages.
U.S. Appl. No. 14/063,541, Non-Final Office Action, May 5, 2016, 8 pages.
U.S. Appl. No. 14/458,919, Affidavit-Traversing Rejections or Objections Rule 132, Oct. 6, 2015, 8 pages.
U.S. Appl. No. 14/458,919, Final Office Action, Apr. 29, 2016, 18 pages.
U.S. Appl. No. 14/458,919, Non-Final Office Action, Apr. 6, 2015, 11 pages.
U.S. Pat. No. 8,258,186, Applicant-Initiated Interview Summary, May 16, 2012, 3 pages.
U.S. Pat. No. 8,258,186, Non-Final Office Action, Apr. 5, 2012, 7 pages.
U.S. Pat. No. 8,258,186, Notice of Allowance, Jun. 14, 2012, 7 pages.
U.S. Pat. No. 8,445,540, Final Office Action, Apr. 1, 2010, 12 pages.
U.S. Pat. No. 8,445,540, Non-Final Office Action, May 27, 2009, 12 pages.
U.S. Pat. No. 8,445,540, Notice of Allowance, dated Jan. 22, 2013, 8 pages.
U.S. Pat. No. 8,609,734, Applicant-Initiated Interview Summary, Feb. 12, 2013, 4 pages.
U.S. Pat. No. 8,609,734, Non-Final Office Action, Dec. 4, 2012, 9 pages.
U.S. Pat. No. 8,609,734, Notice of Allowance, Aug. 2, 2013, 6 pages.
U.S. Pat. No. 8,858,991, Applicant-Initiated Interview Summary, Dec. 23, 2013, 3 pages.
U.S. Pat. No. 8,858,991, Examiner-Initiated Interview Summary, Feb. 21, 2014, 1 page.
U.S. Pat. No. 8,858,991, Examiner-Initiated Interview Summary, Feb. 25, 2014, 2 pages.
U.S. Pat. No. 8,858,991, Final Office Action, Feb. 21, 2014, 16 pages.
U.S. Pat. No. 8,858,991, Non-Final Office Action, May 9, 2013, 18 pages.
U.S. Pat. No. 8,858,991, Notice of Allowance, dated Jun. 9, 2014, 10 pages.
Vogt et al., Elevated osteopontin levels in active relapsing-remitting multiple sclerosis. Ann Neurol. 53(6): 819-22 (2003).
Von Hoff, D. D., et al., "Methylglyoxal Bis-Guanylhydrazone in Advanced Bladder Cancer", European Journal of Cancer and Clinical Oncology, Oxford, GB, 26(7):848, (Jan. 1, 1990).
Von Hoff, D.D., "MGBG: Teaching an old drug new tricks," 1994, Annals of Oncology 5: 487-493.
Wagner, CA et al., Novel Insights and Therapeutics in Multiple Sclerosis [v1; ref status: indexed, http://f1000r.es/59z], F1000Research 2015, 4(F1000 Faculty Rev):517 (doi:10.12688/f1000research.6378.1).
Wallace HM et al., Inhibitors of polyamine metabolism: review article. Amino Acids. 26(4):353-65 (2004).
Wang, X., "Diffusion Tensor Imaging Detects Treatment Effects of FTY720 in Experimental Autoimmune Encephalomyelitis Mice", NMR Biomed. 26(12):1742-50, (Aug. 2013).
Webb et al., Direct observation and quantification of macrophage chemoattraction to the growth factor CSF-1. J Cell Sci. 109: 793-803 (1996).
Weber et al., Phosphorylation-Dependent Interaction of Osteopontin With its Receptors Regulates Macrophage Migration and Activation, J Leukoc Biol. 72, 752-761, 2002.
White, Florence R., 'Methyl-GAG', Cancer Bulletin, vol. 24, 1 pp. 79-84, XP009164055, ISSN: 0008-5448 Nov. 1962 (Nov. 1, 1962).
WO 2008/112659 International Preliminary Report on Patentability, dated Sep. 15, 2009, 6 pages.
WO 2008/112659 International Search Report, dated Sep. 2, 2008, 4 pages.
WO 2008/112659 Written Opinion, dated Sep. 2, 2008, 5 pages.
WO 2011/009039 International Preliminary Report on Patentability, dated Jan. 17, 2012, 7 pages.
WO 2011/009039 International Search Report, dated Apr. 25, 2011, 5 pages.
WO 2011/009039 Written Opinion, dated Apr. 25, 2011, 6 pages.
WO 2012/100043 International Preliminary Report on Patentability, dated Jul. 23, 2013, 8 pages.
WO 2012/100043 International Search Report, dated Aug. 7, 2012, 4 pages.
WO 2012/100043 Written Opinion, dated Aug. 7, 2012, 7 pages.
WO 2014/110154 International Preliminary Report on Patentability, dated Jul. 14, 2015, 6 pages.
WO 2014/110154 International Search Report, dated May 2, 2014, 6 pages.
WO 2014/110154 Written Opinion, dated May 2, 2014, 5 pages.
Wong CK et al., Elevation of plasma osteopontin concentration is correlated with disease activity in patients with systemic lupus erythematosus. Rheumatology (Oxford). 44(5): 602-6 (2005).
www.metrohealth.org (accessed online May 18, 2009), 2 pages.
Xu, G. et al., Role of Osteopontin in Amplification and Perpetuation of Rheumatoid Synovitis, J Clin Invest. 115(4), 1060-1067, 2005.
Yoshitake, H. et al., Osteopontin-Deficient Mice are Resistant to Ovariectomy-Induced Bone Resorption, PNAS 96, 8156-8160, 1999.
Yu, X. et al., A Functional Role for Osteopontin in Experimental Crescentic Glomerulonephritis in the Rat, Proc Assoc Am Physicians 110(1), 50-64, 1998.
Zagon, I. et al., Multiple Sclerosis: Perspectives in Treatment and Pathogenesis, Department of Neural & Behavioral Sciences, Pennsylvania State University College of Medicine, Hershey, Pennsylvania, USA, 2017, 204 pages.
Zhang, J. et al., The Role of Adenosine A2A and A2B Receptors in Regulation of TNF-alpha Production by Human Monocytes, Biochem Pharmacol. 69, 883-889, 2005.
Zhao, et al., "Pharmacokinetics of Rhein Enteric-Coated Sustained-Release Pellets in Rabbits", Zhongguo Shiyan Fangjixue Zazhi, 19(8):159-62, (2013), (Abstract only).
Zhong, J. et al., Osteopontin Deficiency Protects Mice from Dextran Sodium Sulfate-Induced Colitis, Inflamm Bowel Dis. 12(8), 790-796, 2006.
Ziemssen, T. et al., Evaluation of Study and Patient Characteristics of Clinical Studies in Primary Progressive Multiple Sclerosis: A Systematic Review, PLoS One, 2015, 22 pages.
U.S. Appl. No. 15/594,199; Corrected Notice of Allowability, dated Apr. 3, 2019; 11 pages.
U.S. Appl. No. 16/371,734; Application as filed, dated Apr. 1, 2019; 32 pages.

METHODS AND COMPOSITIONS FOR TREATMENT OF DEMYELINATING DISEASES

This application is a continuation of U.S. application Ser. No. 14/759,599, filed Jul. 7, 2015, which is a national stage entry under 35 U.S.C. § 371 of international application no. PCT/US2014/010714, filed Jan. 8, 2014, which claims the benefit of priority of U.S. provisional applications No. 61/750,336, filed Jan. 8, 2013, and No. 61/823,276, filed May 14, 2013, the disclosures of which are incorporated by reference as if written herein in their entireties.

Disclosed herein are new oral pharmaceutical compositions of SAMDC inhibitors, polyamine analogs, and polyamine biosynthesis inhibitors, and their application for the treatment of conditions including demyelinating diseases, autoimmune disorders affecting the nervous system, and other neurodegenerative conditions.

MGBG (methylglyoxal bis(guanylhydrazone); mitoguazone) is a competitive polyamine inhibitor of S-adenosyl methionine decarboxylase (SAMDC, AMD-I), which catalyzes the synthesis of spermidine, a polyamine. The amino-acid-derived polyamines have long been associated with cell growth and cancer, and specific oncogenes and tumor-suppressor genes regulate polyamine metabolism. Inhibition of polyamine synthesis has proven to be generally ineffective as an anticancer strategy in clinical trials, but it is a potent cancer chemoprevention strategy in preclinical studies. Despite its novel mechanism of action and promising preclinical data, initial clinical trials of MGBG were ceased in the middle of 1960s due to severe toxicity especially to self-renewing normal tissues such as the bone marrow and intestinal tract (particularly severe mucositis), which were both dose and schedule dependent.

Regardless, research has continued with MGBG. A number of studies have examined potential uses in combination with other chemotherapeutic agents and innovative dosing regimens, designed to minimize side effects and dose where possible. Others have focused on elucidating MGBG's modes of action in the body. Yet others have investigated MGBG's activity in diseases other than cancer.

Perhaps due to negative clinical findings in these early studies, to date, MGBG had been confined to intravenous use. As a practical matter, this presents a number of problems for treatment of many diseases, particularly of chronic or recurrent conditions. Administration via IV injection or infusion must be done by a medical professional in a hospital setting. This not only presents an inconvenience and increased cost to the subject, but it also exposes him or her to hospital-based infections and illnesses, this latter both from venipuncture and the hospital or clinic visit itself. In immunocompromised individuals, individuals undergoing treatment with immune system suppressors, and the elderly, this is a relevant concern. Thus, a subject with a long-term chronic condition such as an autoimmune or hyperproliferative disorder, or a doctor treating such a subject, might find the cost, inconvenience, and risks of such a treatment more important than any potential therapeutic benefits the drug might offer. Additionally, I.V. infusion drugs suffer from high Cmax and Tmax liabilities as opposed to oral drugs, which are more slowly absorbed.

An oral formulation of MGBG, in contrast, would present several benefits. First, an oral formulation, for example a simple pill or tablet, may be taken outside of a hospital setting, increasing the potential for subject ease of use and compliance. This permits a subject to avoid infection risks concomitant with IV administration and hospital visits. Where early treatment can prevent the development of disease complications, this is of particular benefit. Chronic low-dose administration of MGBG is practically impossible in an IV formulation. Additionally, oral delivery typically avoids the high concentration peak and rapid clearance associated with an IV bolus dose. Yet another advantage of an oral drug would be the ability to formulate MGBG as a combination composition with one or more other therapeutic agents.

Figure 1:
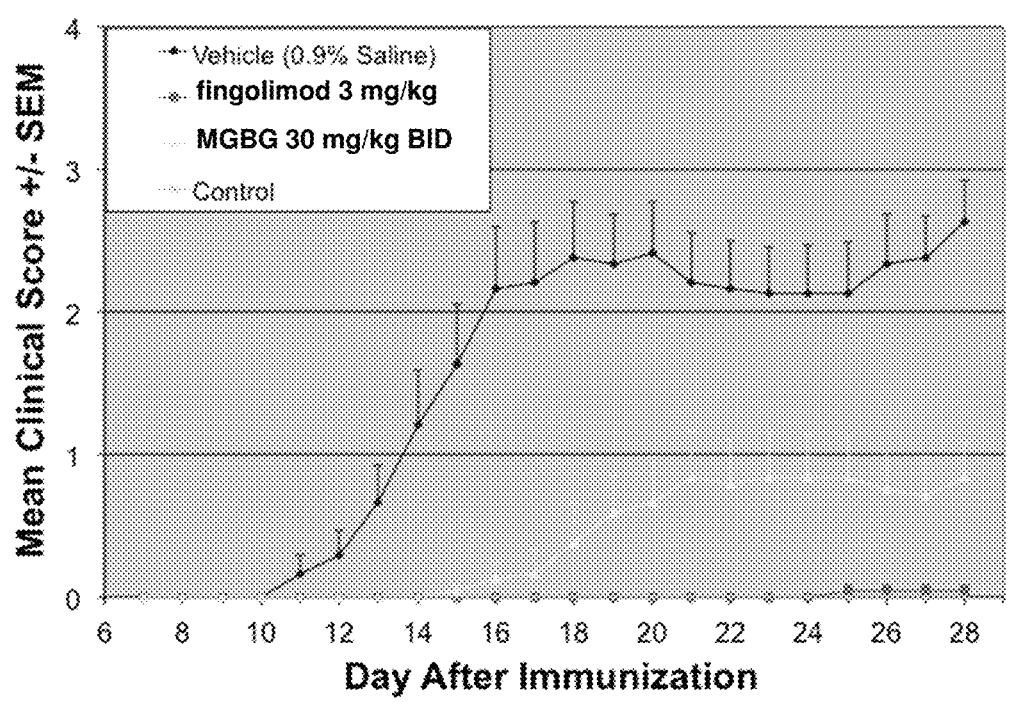
FIG. 1 shows the mean clinical scores of subjects in the first 28-day murine model of experimental autoimmune encephalomyelitis (EAE) (a chronic progressive model of MS) induced by inoculation with myelin oligodendrocyte glycoprotein (MOG) peptides, wherein test subjects were dosed with vehicle, 30 mpk MGBG (twice-daily), or 3 mpk fingolimod (once-daily), and compared with mock-immunized subjects.

Accordingly, provided herein is a method of treatment or prevention of a demyelinating disease, or a symptom thereof, comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes *dorsalis*, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments above is combined with one or more of the other non-contradictory embodiments, such that the resulting embodiment includes the two or more recited elements and/or limitations.

Also provided herein is a method of treatment of a symptom of an autoimmune disease affecting the nervous system comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the symptom is chosen from CNS inflammation, demyelination, and paralysis.

In certain embodiments, the autoimmune disease affecting the nervous system is chosen from multiple sclerosis, polymyalgia, myasthenia gravis, Guillain-Barré Syndrome, chronic inflammatory demyelinating polyneuropathy, transverse myelitis, Balo concentric sclerosis, pernicious anemia, acute disseminated encephalomyelitis (ADME), amyotrophic lateral sclerosis (ALS), autoimmune peripheral neuropathy, lupus erythematosus, psoriatic arthritis, rheumatoid arthritis, osteoarthritis, and rheumatic fever.

In certain embodiments, the autoimmune disease affecting the nervous system disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments is combined with one or more of the other non-contradictory embodiments, such that the resulting embodiment includes the two or more recited elements and/or limitations.

Also provided herein is a method of treatment or prevention of a demyelinating disease comprising the contemporaneous administration of a SAMDC inhibitor and an agent chosen from interferon beta-1a, interferon beta-1b, glatiramer acetate, mitoxantrone, natalizumab, fingolimod, dimethyl fumarate, and teriflunomide.

In certain embodiments, the other agent is fingolimod.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the demyelinating disease is chosen from multiple sclerosis, Guillain-Barré Syndrome, chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments above is combined with one or more of the other non-contradictory embodiments, such that the resulting embodiment includes the two or more recited elements and/or limitations.

Also provided herein is a pharmaceutical composition comprising a SAMDC inhibitor and another agent chosen from interferon beta-1a, interferon beta-1b, glatiramer acetate, mitoxantrone, natalizumab, fingolimod, and teriflunomide, together with a pharmaceutically acceptable carrier.

In certain embodiments, the SAMDC inhibitor is selectively uptaken into cells.

In certain embodiments, the SAMDC inhibitor is MGBG.

In certain embodiments, MGBG is dosed at 20 mg/day to 400 mg/day.

In certain embodiments, the other agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, the pharmaceutical formulation comprising the SAMDC inhibitor and fingolimod is formulated for oral administration.

In certain embodiments, the pharmaceutical formulation yields a therapeutically effective systemic plasma MGBG level when orally administered to a subject.

In certain embodiments, the pharmaceutical formulation is formulated for once-daily dosing.

In certain embodiments, the pharmaceutical formulation comprises 0.5 mg fingolimod per dosage unit.

In certain embodiments, the pharmaceutical formulation comprises less than 0.5 mg fingolimod per dosage unit.

In certain embodiments, the pharmaceutical formulation comprises 0.25 mg fingolimod per dosage unit.

In certain embodiments, the pharmaceutical formulation is formulated for twice-daily dosing.

In certain embodiments, the pharmaceutical formulation comprises 0.25 mg fingolimod per dosage unit.

In certain embodiments, the pharmaceutical formulation comprises less than 0.25 mg fingolimod per dosage unit.

In certain embodiments, the pharmaceutical formulation comprises about 0.125 mg fingolimod per dosage unit.

Also provided herein are embodiments in which each of the embodiments above is combined with one or more of the other non-contradictory embodiments, such that the resulting embodiment includes the two or more recited elements and/or limitations.

Also provided is a method of prevention of relapse or progression, or decreasing severity of symptoms in a relapse, of a demyelinating disease in a patient, comprising the administration of a therapeutically effective amount of a SAMDC inhibitor.

In certain embodiments, provided is a method of prevention of progression, or decreasing severity of symptoms in a relapse, of a demyelinating disease in a patient, comprising the administration of a therapeutically effective amount of MGBG.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes *dorsalis*, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the SAMDC inhibitor is not a T-cell regulator.

In certain embodiments, administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to another therapeutic agent approved for the treatment of a demyelinating disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, administration occurs concomitant with a reduced incidence of at least one side effect chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of at least two side effects chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of cytopenia, nephrotoxicity, and hepatotoxicity.

In certain embodiments, the cytopenia is chosen from lymphopenia and neutropenia.

In certain embodiments, administration additionally occurs concomitant with a reduced incidence of cardiotoxicity, and teratogenicity.

Also provided herein are embodiments in which each of the embodiments above is combined with one or more of the other non-contradictory embodiments, such that the resulting embodiment includes the two or more recited elements and/or limitations.

Also provided is a method treatment of progressive multiple sclerosis in a patient, comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the progressive multiple sclerosis is primary progressive.

In certain embodiments, the progressive multiple sclerosis is secondary progressive.

In certain embodiments, the progressive multiple sclerosis is progressive relapsing.

In certain embodiments, the administration of MGBG is oral.

In certain embodiments, MGBG is dosed at 20 mg/day to 400 mg/day.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, the treatment prevents relapse or progression of MS.

In certain embodiments, the SAMDC inhibitor is not a T-cell regulator.

In certain embodiments, administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to another therapeutic agent approved for the treatment of a demyelinating disease.

In certain embodiments, the demyelinating disease is multiple sclerosis.

In certain embodiments, administration occurs concomitant with a reduced incidence of at least one side effect chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of at least two side effects chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of cytopenia, nephrotoxicity, and hepatotoxicity.

In certain embodiments, the cytopenia is chosen from lymphopenia and neutropenia.

In certain embodiments, administration additionally occurs concomitant with a reduced incidence of cardiotoxicity, and teratogenicity.

Also provided herein are embodiments in which each of the embodiments above is combined with one or more of the other non-contradictory embodiments, such that the resulting embodiment includes the two or more recited elements and/or limitations.

Also provided is a method of blocking antigen presentation on cells in a patient having a demyelinating disease, wherein the antigens are derived from, mimic, or resemble antigens in the myelin sheath, comprising the administration of a therapeutically effective amount of a SAMDC inhibitor.

In certain embodiments, the cells are of myeloid lineage.

In certain embodiments, the cells are pro-inflammatory.

In certain embodiments, the cells are chosen from dendritic cells, macrophages, and B-cells.

In certain embodiments, the cells are dendritic cells.

In certain embodiments, the cells are M1 macrophages.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, the SAMDC inhibitor is not a T-cell regulator.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to another therapeutic agent approved for the treatment of a demyelinating disease.

In certain embodiments, the demyelinating disease is multiple sclerosis.

In certain embodiments, administration occurs concomitant with a reduced incidence of at least one side effect chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of at least two side effects chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of cytopenia, nephrotoxicity, and hepatotoxicity.

In certain embodiments, the cytopenia is chosen from lymphopenia and neutropenia.

In certain embodiments, administration additionally occurs concomitant with a reduced incidence of cardiotoxicity, and teratogenicity.

Also provided herein are embodiments in which each of the embodiments above is combined with one or more of the other non-contradictory embodiments, such that the resulting embodiment includes the two or more recited elements and/or limitations.

Also provided is a method of inhibition of infiltration of an antigen-presenting cells into the central nervous system of a patient having a demyelinating disease, comprising the administration of a therapeutically effective amount of a SAMDC inhibitor.

In certain embodiments, the cells are pro-inflammatory.

In certain embodiments, the cells are chosen from dendritic cells, macrophages, and B-cells.

In certain embodiments, the cells are dendritic cells.

In certain embodiments, the cells are M1 macrophages.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to another therapeutic agent approved for the treatment of a demyelinating disease.

In certain embodiments, the demyelinating disease is multiple sclerosis.

In certain embodiments, administration occurs concomitant with a reduced incidence of at least one side effect chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of at least two side effects chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of cytopenia, nephrotoxicity, and hepatotoxicity.

In certain embodiments, the cytopenia is chosen from lymphopenia and neutropenia.

In certain embodiments, administration additionally occurs concomitant with a reduced incidence of cardiotoxicity, and teratogenicity.

Also provided herein are embodiments in which each of the embodiments above is combined with one or more of the other non-contradictory embodiments, such that the resulting embodiment includes the two or more recited elements and/or limitations.

Also provided is a method of prevention or reduction in severity of the initiation phase of autoimmune response in a patient having a demyelinating disease, comprising the administration of a therapeutically effective amount of a SAMDC inhibitor.

In certain embodiments, the administration additionally prevents or reduces the amplification phase of autoimmune response in a patient having a demyelinating disease.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes *dorsalis*, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the SAMDC inhibitor is not a T-cell regulator.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

In certain embodiments, administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to another therapeutic agent approved for the treatment of a demyelinating disease.

In certain embodiments, the demyelinating disease is multiple sclerosis.

In certain embodiments, administration occurs concomitant with a reduced incidence of at least one side effect chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of at least two side effects chosen from cytopenia, nephrotoxicity, hepatotoxicity, cardiotoxicity, and teratogenicity.

In certain embodiments, the cytopenia is chosen from lymphopenia and neutropenia.

In certain embodiments, administration occurs concomitant with a reduced incidence of cytopenia, nephrotoxicity, and hepatotoxicity.

In certain embodiments, the cytopenia is chosen from lymphopenia and neutropenia.

In certain embodiments, administration additionally occurs concomitant with a reduced incidence of cardiotoxicity, and teratogenicity.

Also provided herein are embodiments in which each of the embodiments above is combined with one or more of the other non-contradictory embodiments, such that the resulting embodiment includes the two or more recited elements and/or limitations.

Also provided is a method of treatment or prevention of demyelination in a subject in need thereof, comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments above is combined with one or more of the other non-contradictory embodiments, such that the resulting embodiment includes the two or more recited elements and/or limitations.

Also provided is a method of reduction in severity of cellular apoptosis in the nerve tissue of a subject in need thereof, comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments above is combined with one or more of the other non-contradictory embodiments, such that the resulting embodiment includes the two or more recited elements and/or limitations.

Also provided is a method of prevention of or reduction in the development of inflammatory foci in the nerve tissue of a subject in need thereof, comprising the administration of a therapeutically effective amount of a SAMDC inhibitor.

In certain embodiments, the SAMDC inhibitor is selectively uptaken into cells.

In certain embodiments, the SAMDC inhibitor is MGBG.

In certain embodiments, the administration of MGBG is oral.

In certain embodiments, MGBG is dosed at 20 mg/day to 400 mg/day.

In certain embodiments, the demyelinating disease is chosen from multiple sclerosis, optic neuritis, an idiopathic inflammatory demyelinating disease, Guillain-Barré Syndrome, chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

In certain embodiments, the demyelinating disease is multiple sclerosis.

In certain embodiments, the method additionally comprises the administration of an agent chosen from interferon beta-1a, interferon beta-1b, glatiramer acetate, mitoxantrone, natalizumab, fingolimod, laquinimod, dimethyl fumarate, and teriflunomide.

In certain embodiments, the agent is fingolimod.

In certain embodiments, fingolimod is dosed at 0.5 mg per day.

In certain embodiments, fingolimod is dosed at less than 0.5 mg per day.

In certain embodiments, fingolimod is dosed at 0.25 mg per day.

Also provided herein are embodiments in which each of the embodiments above is combined with one or more of the other non-contradictory embodiments, such that the resulting embodiment includes the two or more recited elements and/or limitations.

The present disclosure contemplates not only the methods disclosed above, but also:

the corresponding use of the compounds above in the treatment of disease, and in the specific diseases discussed; and the corresponding use of the compounds above in the manufacture of medicaments for the treatment of the diseases discussed.

In the interest of avoidance of repetition, such embodiments are not explicitly re-written herein. However, these embodiments should be understood to be included as if so written. For example, the present disclosure provides for:

Use of a therapeutically effective amount of a SAMDC inhibitor in the treatment or prevention of a demyelinating disease;

Use of a therapeutically effective amount of a SAMDC inhibitor in the treatment of a symptom of an autoimmune disease affecting the nervous system;

Use of a therapeutically effective amount of a SAMDC inhibitor and an agent chosen from interferon beta-1a, interferon beta-1b, glatiramer acetate, mitoxantrone, natalizumab, fingolimod, dimethyl fumarate, and teriflunomide in the treatment or prevention of a demyelinating disease;

Use of a therapeutically effective amount of a SAMDC inhibitor in the prevention of relapse or progression, or decreasing severity of symptoms in a relapse, of a demyelinating disease;

Use of a therapeutically effective amount of a SAMDC inhibitor in the treatment of progressive multiple sclerosis in a patient;

Use of a therapeutically effective amount of a SAMDC inhibitor in blocking antigen presentation on cells in a patient having a demyelinating disease, wherein the antigens are derived from, mimic, or resemble antigens in the myelin sheath;

Use of a therapeutically effective amount of a SAMDC inhibitor in the inhibition of infiltration of an antigen-presenting cells into the central nervous system of a patient having a demyelinating disease;

a method of prevention or reduction in severity of the initiation phase of autoimmune response in a patient having a demyelinating disease, comprising the administration of a therapeutically effective amount of a SAMDC inhibitor.

Use of a therapeutically effective amount of a SAMDC inhibitor in the treatment or prevention of demyelination in a subject in need thereof;

Use of a therapeutically effective amount of a SAMDC inhibitor in the reduction in severity of cellular apoptosis in the nerve tissue of a subject in need thereof; and/or Use of a therapeutically effective amount of a SAMDC inhibitor in the prevention of or reduction in the development of inflammatory foci in the nerve tissue of a subject in need thereof;

and all dependent embodiments listed above and in the claims below. The present disclosure also provides for:

Use of a SAMDC inhibitor in the manufacture of a medicament for the treatment or prevention of a demyelinating disease;

Use of a SAMDC inhibitor in the manufacture of a medicament for the treatment of a symptom of an autoimmune disease affecting the nervous system;

Use of a SAMDC inhibitor and an agent chosen from interferon beta-1a, interferon beta-1b, glatiramer acetate, mitoxantrone, natalizumab, fingolimod, dimethyl fumarate, and teriflunomide in the manufacture of a medicament for the treatment or prevention of a demyelinating disease;

Use of a SAMDC inhibitor in the manufacture of a medicament for the prevention of relapse or progression, or decreasing severity of symptoms in a relapse, of a demyelinating disease;

Use of a SAMDC inhibitor in the manufacture of a medicament for the treatment of progressive multiple sclerosis in a patient;

Use of a SAMDC inhibitor in the manufacture of a medicament for blocking antigen presentation on cells in a patient having a demyelinating disease, wherein the antigens are derived from, mimic, or resemble antigens in the myelin sheath;

Use of a SAMDC inhibitor in the manufacture of a medicament for the inhibition of infiltration of an antigen-presenting cells into the central nervous system of a patient having a demyelinating disease;

a method of prevention or reduction in the manufacture of a medicament for severity of the initiation phase of autoimmune response in a patient having a demyelinating disease, comprising the administration of a SAMDC inhibitor.

Use of a SAMDC inhibitor in the manufacture of a medicament for the treatment or prevention of demyelination in a subject in need thereof;

Use of a SAMDC inhibitor in the manufacture of a medicament for the reduction in severity of cellular apoptosis in the nerve tissue of a subject in need thereof; and/or Use of a SAMDC inhibitor in the manufacture of a medicament for the prevention of or reduction in the development of inflammatory foci in the nerve tissue of a subject in need thereof;

and all dependent embodiments listed above and in the claims below.

Also disclosed herein are oral pharmaceutical formulations of MGBG and other polyamine analogs, polyamine biosynthesis inhibitors, and polyamine inhibitors of SAMDC. Also disclosed are methods for the treatment of diseases comprising the administration of MGBG and other polyamine analogs, polyamine biosynthesis inhibitors, and polyamine inhibitors of SAMDC.

Also provided herein are methods for the treatment of pain comprising the administration of MGBG and other polyamine analogs, polyamine biosynthesis inhibitors, and polyamine inhibitors of SAMDC.

Also provided herein is a pharmaceutical composition for oral delivery, comprising a polyamine analog or polyamine biosynthesis inhibitor together with at least one pharmaceutically acceptable oral excipient.

Also provided herein is an oral pharmaceutical composition, comprising polyamine analog or polyamine biosynthesis inhibitor together with at least one oral pharmaceutically acceptable excipient, which yields a therapeutically effective systemic plasma polyamine analog or polyamine biosynthesis inhibitor level when orally administered to a subject.

Also provided herein is an oral pharmaceutical composition, comprising polyamine analog or polyamine biosynthesis inhibitor together with at least one oral pharmaceutically acceptable excipient, which yields a therapeutically effective systemic plasma polyamine analog or polyamine biosynthesis inhibitor level for the treatment of pain when orally administered to a subject.

In certain embodiments, the polyamine analog or polyamine biosynthesis inhibitor is a compound disclosed herein.

In certain embodiments, the polyamine analog or polyamine biosynthesis inhibitor is one known in the art.

In certain embodiments, the pharmaceutical composition yields a therapeutically effective systemic plasma level of a polyamine analog or polyamine biosynthesis inhibitor for a period of at least 4, 5, 6, 7, 8, 9, 10, 11, 12, 13, 14, 15, 16, 17, 18, 19, 20, 21, 22, 23, 24, 30, 36, or 48 hours. In further embodiments, the pharmaceutical composition yields a therapeutically effective systemic plasma level of a polyamine analog or polyamine biosynthesis inhibitor for at least a 6-hour period. In further embodiments, the pharmaceutical composition yields a therapeutically effective systemic plasma level of a polyamine analog or polyamine biosynthesis inhibitor for at least a 12-hour period. In further embodiments, the pharmaceutical composition yields a therapeutically effective systemic plasma level of a polyamine analog or polyamine biosynthesis inhibitor for at least an 18-hour period. In further embodiments, the pharmaceutical composition yields a therapeutically effective systemic plasma level of a polyamine analog or polyamine biosynthesis inhibitor for at least a 24-hour period.

In certain embodiments, the pharmaceutical composition yields a plasma level of a polyamine analog or polyamine biosynthesis inhibitor of at least 25, 50, 55, 60, 65, 75, 80, 85, 90, or 95 percent of the peak plasma concentration for at least 4 hours. In certain embodiments, the pharmaceutical composition yields a plasma level of a polyamine analog or polyamine biosynthesis inhibitor of at least 75% of the peak plasma concentration for at least 4, 6, 8, 10, 12, 14, 16, 18, 20, 22, or 24 hours. In certain embodiments, the pharmaceutical composition yields a plasma level of a polyamine analog or polyamine biosynthesis inhibitor of at least 75% of the peak plasma concentration for at least 4 hours. In certain embodiments, the pharmaceutical composition yields a plasma level of a polyamine analog or polyamine biosynthesis inhibitor of at least 75% of the peak plasma concentration for at least 6 hours. In certain embodiments, the pharmaceutical composition yields a plasma level of a polyamine analog or polyamine biosynthesis inhibitor of at least 75% of the peak plasma concentration for at least 8 hours. In certain embodiments, the pharmaceutical composition yields a plasma level of a polyamine analog or polyamine biosynthesis inhibitor of at least 50% of the peak plasma concentration for at least 8 hours. In certain embodiments, the pharmaceutical composition yields a plasma level of a polyamine analog or polyamine biosynthesis inhibitor of at least 50% of the peak plasma concentration for at least 12 hours. In certain embodiments, the pharmaceutical composition yields a plasma level of a polyamine analog or polyamine biosynthesis inhibitor of at least 50% of the peak plasma concentration for at least 18 hours. In certain embodiments, the pharmaceutical composition yields a plasma level of a polyamine analog or polyamine biosynthesis inhibitor of at least 25% of the peak plasma concentration for at least 18 hours. In further embodiments, the peak plasma concentration is a therapeutically effective concentration. In yet further embodiments, the percentage of peak plasma concentration is therapeutically effective over the given time period.

In certain embodiments, the pharmaceutical composition comprising the polyamine analog or polyamine biosynthesis inhibitor has an oral bioavailability of at least 10, 20, 25, 26, 27, 28, 29, 30, 31, 32, 33, 34, 35, 36, 37, 38, 39, 40, 45, 50, 55, or 60 percent. In further embodiments, the pharmaceutical composition has an oral bioavailability of at least 10%, 20%, 25%, 30%, 35%, 40%, or 45%. In further embodiments, the pharmaceutical composition has an oral bioavailability of at least 30%, at least 35%, at least 40% or at least 45%. In certain embodiments, the pharmaceutical composition has an oral bioavailability of at least 20%. In certain embodiments, the pharmaceutical composition has an oral bioavailability of at least 30%. In certain embodiments, the pharmaceutical composition has an oral bioavailability of at least 35%. In certain embodiments, the pharmaceutical composition has an oral bioavailability of at least 40%. In certain embodiments, the pharmaceutical composition has an oral bioavailability of at least 45%. In certain embodiments, the pharmaceutical composition has an oral bioavailability which yields a therapeutically effective plasma level of a polyamine analog or polyamine biosynthesis inhibitor for at least a 24 hour period in the subject with once-daily dosing. In certain embodiments, the pharmaceutical composition has an oral bioavailability which yields a therapeutically effective plasma level of a polyamine analog or polyamine biosynthesis inhibitor for at least a 24 hour period in the subject with twice-daily dosing. In certain embodiments, the pharmaceutical composition has an oral bioavailability which yields a therapeutically effective plasma level of a polyamine analog or polyamine biosynthesis inhibitor for at least a 24 hour period in the subject with thrice-daily dosing.

In certain embodiments, the pharmaceutical composition comprising the polyamine analog or polyamine biosynthesis inhibitor has a half life of at least 4, 6, 8, 10, 12, 14, 16, 18, 19, 20, 21, 22, 23, 24, 26, 28, 30, or 36 hours. In certain embodiments, the pharmaceutical composition has a half life of at least 12 hours. In further embodiments, the pharmaceutical composition has a half life of at least 18 hours. In further embodiments, the pharmaceutical composition has a half life of at least 20 hours. In further embodiments, the pharmaceutical composition has a half life of at least 24 hours. In certain embodiments, the pharmaceutical composition has a half life of at least 48, 72, 96, or 120 hours.

Additionally provided herein is a pharmaceutical composition for oral delivery, comprising MGBG together with at least one pharmaceutically acceptable oral excipient.

Also provided herein is an oral pharmaceutical composition, comprising MGBG together with at least one oral pharmaceutically acceptable excipient, which yields a therapeutically effective systemic plasma MGBG level when orally administered to a subject.

Also provided herein is an oral pharmaceutical composition, comprising MGBG together with at least one oral pharmaceutically acceptable excipient, which yields a therapeutically effective systemic plasma MGBG level for the treatment of pain when orally administered to a subject.

In certain embodiments, the pharmaceutical composition yields a therapeutically effective systemic plasma MGBG level for a period of at least 4, 5, 6, 7, 8, 9, 10, 11, 12, 13, 14, 15, 16, 17, 18, 19, 20, 21, 22, 23, 24, 30, 36, or 48 hours. In further embodiments, the pharmaceutical composition yields a therapeutically effective systemic plasma MGBG level for at least a 6-hour period. In further embodiments, the pharmaceutical composition yields a therapeutically effective systemic plasma MGBG level for at least a 12-hour period. In further embodiments, the pharmaceutical composition yields a therapeutically effective systemic plasma MGBG level for at least an 18-hour period. In further embodiments, the pharmaceutical composition yields a therapeutically effective systemic plasma MGBG level for at least a 24-hour period.

In certain embodiments, the pharmaceutical composition yields a plasma level of MGBG of at least 25, 50, 55, 60, 65, 75, 80, 85, 90, or 95 percent of the peak plasma concentration for at least 4 hours. In certain embodiments, the pharmaceutical composition yields a plasma level of MGBG of at least 75% of the peak plasma concentration for at least 4, 6, 8, 10, 12, 14, 16, 18, 20, 22, or 24 hours. In certain embodiments, the pharmaceutical composition yields a plasma level of MGBG of at least 75% of the peak plasma concentration for at least 4 hours. In certain embodiments, the pharmaceutical composition yields a plasma level of MGBG of at least 75% of the peak plasma concentration for at least 6 hours. In certain embodiments, the pharmaceutical composition yields a plasma level of MGBG of at least 75% of the peak plasma concentration for at least 8 hours. In certain embodiments, the pharmaceutical composition yields a plasma level of MGBG of at least 50% of the peak plasma concentration for at least 8 hours. In certain embodiments, the pharmaceutical composition yields a plasma level of MGBG of at least 50% of the peak plasma concentration for at least 12 hours. In certain embodiments, the pharmaceutical composition yields a plasma level of MGBG of at least 50% of the peak plasma concentration for at least 18 hours. In certain embodiments, the pharmaceutical composition yields a plasma level of MGBG of at least 25% of the peak plasma concentration for at least 18 hours. In further embodiments, the peak plasma concentration is a therapeutically effective concentration. In yet further embodiments, the percentage of peak plasma concentration is therapeutically effective over the given time period.

In certain embodiments, the pharmaceutical composition comprising MGBG has an oral bioavailability of at least 10, 20, 25, 26, 27, 28, 29, 30, 31, 32, 33, 34, 35, 36, 37, 38, 39, 40, 45, 50, 55, or 60 percent. In further embodiments, the pharmaceutical composition has an oral bioavailability of at least 10%, 20%, 25%, 30%, 35%, 40%, or 45%. In further embodiments, the pharmaceutical composition has an oral bioavailability of at least 30%, at least 35%, at least 40% or at least 45%. In certain embodiments, the pharmaceutical composition has an oral bioavailability of at least 20%. In certain embodiments, the pharmaceutical composition has an oral bioavailability of at least 30%. In certain embodiments, the pharmaceutical composition has an oral bioavailability of at least 35%. In certain embodiments, the pharmaceutical composition has an oral bioavailability of at least 40%. In certain embodiments, the pharmaceutical composition has an oral bioavailability of at least 45%. In certain embodiments, the pharmaceutical composition has an oral bioavailability which yields a therapeutically effective plasma level of MGBG for at least a 24 hour period in the subject with once-daily dosing. In certain embodiments, the pharmaceutical composition has an oral bioavailability which yields a therapeutically effective plasma level of MGBG for at least a 24 hour period in the subject with twice-daily dosing. In certain embodiments, the pharmaceutical composition has an oral bioavailability which yields a therapeutically effective plasma level of MGBG for at least a 24 hour period in the subject with thrice-daily dosing.

In certain embodiments, the pharmaceutical composition comprising MGBG has a half life of at least 4, 6, 8, 10, 12, 14, 16, 18, 19, 20, 21, 22, 23, 24, 26, 28, 30, or 36 hours. In certain embodiments, the pharmaceutical composition has a half life of at least 12 hours. In further embodiments, the pharmaceutical composition has a half life of at least 18 hours. In further embodiments, the pharmaceutical composition has a half life of at least 20 hours. In further embodiments, the pharmaceutical composition has a half life of at least 24 hours. In certain embodiments, the pharmaceutical composition has a half life of at least 48, 72, 96, or 120 hours.

Also provided herein is a pharmaceutical composition comprising MGBG together with at least one oral pharmaceutically acceptable excipient, which yields a therapeutically effective systemic plasma MGBG level when orally administered to a subject, which does not have substantially dose-limiting side effects. In certain embodiments, said side effects are gastrointestinal. In further embodiments, said gastrointestinal side effects are chosen from nausea, vomiting, diarrhea, abdominal pain, oral mucositis, oral ulceration, pharyngitis, stomatitis, gastrointestinal perforations, gastrointestinal ulcers, gastrointestinal obstructions, and gastrointestinal bleeds. In further embodiments, said gastrointestinal side effects are chosen from inhibition of gastrointestinal mucosal proliferation, inhibition of migration of developing epithelial lumen cells, and inhibition of differentiation of stem or progenitor cells into epithelial lumen cells. In certain embodiments, said side effects are chosen from thrombocytopenia, leukopenia, phlebitis, laryngitis, cellulitis, dermatitis, and hypoglycemia.

Also provided herein is a low-dose oral pharmaceutical composition for chronic delivery, comprising a therapeutically effective amount of MGBG and at least one pharmaceutically acceptable excipient, which does not have substantial gastrointestinal side effects. In certain embodiments, the low-dose oral pharmaceutical composition for chronic delivery, comprising a therapeutically effective amount of MGBG and at least one pharmaceutically acceptable excipient, which does not have substantial gastrointestinal side effects, yields a therapeutically effective plasma level of MGBG for at least a 24 hour period in the subject with once-daily dosing.

In certain embodiments, the pharmaceutical composition is formulated as a tablet or capsule. For example, in certain embodiments, the pharmaceutical composition comprises:
  0.1-50% of a polyamine analog or a polyamine biosynthesis inhibitor;
  0.1-99.9% of a filler;
  0-10% of a disintegrant;
  0-5% of a lubricant; and,
  0-5% of a glidant.

In certain embodiments, the pharmaceutical composition comprises:
  0.1-50% of MGBG;
  0.1-99.9% of a filler;
  0-10% of a disintegrant;
  0-5% of a lubricant; and,
  0-5% of a glidant.

In further embodiments,
  said filler is chosen from a sugar, a starch, a cellulose, and a poloxamer;
  said disintegrant is chosen from povidone and crospovidone;
  said lubricant is magnesium stearate; and
  said glidant is silicon dioxide.

In further embodiments,
  said filler is chosen from lactose and microcrystalline cellulose;
  said disintegrant is chosen from povidone and crospovidone;
  said lubricant is magnesium stearate; and
  said glidant is silicon dioxide.

In certain embodiments, the pharmaceutical composition comprises:
  10-300 mg of a polyamine analog or a polyamine biosynthesis inhibitor, making up 2-50% of the tablet content or capsule fill content;
  0-10% of a disintegrant;
  0-5% of a lubricant;
  0-5% of a glidant; and
  30-98% of a filler.

In certain embodiments, the pharmaceutical composition comprises:
  10-300 mg of MGBG, making up 2-50% of the tablet content or capsule fill content;
  0-10% of a disintegrant;
  0-5% of a lubricant;
  0-5% of a glidant; and
  30-98% of a filler.

In further embodiments, the pharmaceutical composition comprises
  0.1-10% of a binder;
  0-5% of a surfactant;
  0-10% of an intergranular disintegrant; and
  0-10% of an extragranular disintegrant.

In further embodiments, the pharmaceutical composition may additionally comprise
  0-10% of a binder;
  0-5% of a surfactant;
  0-10% of an intergranular disintegrant; and
  0-10% of an extragranular disintegrant.

In further embodiments,
  said binder is chosen from copolyvidone, hydroxypropylcellulose, hydroxypropylmethylcellulose, and povidone;
  said surfactant is chosen from polyoxyethylene (20) sorbitan monooleate, a poloxamer, and sodium lauryl sulfate;
  said intergranular disintegrant is chosen from croscarmellose sodium, sodium starch glyconate, and crospovidone; and
  said extragranular disintegrant is chosen from croscarmellose sodium, sodium starch glyconate, and crospovidone.

Also provided herein is a method of treating or delaying the onset or development of a condition in a subject in need thereof comprising the administration of an oral pharmaceutical composition comprising MGBG and at least one pharmaceutically acceptable excipient. In certain embodiments, the oral pharmaceutical composition is delivered in a therapeutically effective amount. In certain embodiments, said oral pharmaceutical composition has an oral bioavailability of at least 30%. In certain embodiments, said oral pharmaceutical composition does not have substantially dose-limiting side effects. In certain embodiments, the plasma level of MGBG is at least 75% of the peak plasma concentration for 4 or more hours. In further embodiments, said oral pharmaceutical composition yields a therapeutically effective systemic plasma MGBG level for at least a 12-hour period when orally administered to a subject.

In certain embodiments, said condition is chosen from a proliferative disorder, an inflammatory disease, and an autoimmune disease, a neuropathy, and a neurodegenerative disease. In certain embodiments, said condition is chosen from rheumatoid arthritis, osteoarthritis, multiple sclerosis, amyotrophic lateral sclerosis, HIV neuropathy, and HIV associated dementia.

In certain embodiments, said proliferative disorder is chosen from a cancer, psoriasis, psoriatic arthritis and atopic dermatitis. In certain embodiments, the neuropathy is chosen from peripheral neuropathy, diabetic neuropathy, entrapment neuropathy (carpel tunnel syndrome), postherpetic neuralgia (PHN), chemotherapy-induced neuropathy, and HIV neuropathy.

In certain embodiments, the condition is chosen from a proliferative disorder, rheumatoid arthritis, osteoarthritis, multiple sclerosis, and amyotrophic lateral sclerosis. In certain embodiments, the proliferative disorder could, for example, be chosen from a cancer, psoriasis, psoriatic arthritis, and atopic dermatitis.

Also provided is an oral pharmaceutical composition, comprising a polyamine analog or polyamine biosynthesis inhibitor together with at least one oral pharmaceutically acceptable excipient, which yields a therapeutically effective systemic plasma level of the polyamine analog or polyamine biosynthesis inhibitor for the treatment of pain when orally administered to a subject. Also provided is an oral pharmaceutical composition, comprising MGBG together with at least one oral pharmaceutically acceptable excipient, which yields a therapeutically effective systemic plasma level of MGBG for the treatment of pain when orally administered to a subject.

Also provided herein is a method of treatment of pain in a subject in need thereof comprising the administration of a polyamine analog or a polyamine biosynthesis inhibitor, or a salt or protected derivative thereof. Also provided herein is a method of treatment of pain in a subject in need thereof comprising the administration of MGBG. In certain embodiments, the MGBG is administered in a therapeutically effective amount. Further provided is a method of treatment of pain in a subject in need thereof comprising the administration of a therapeutically effective amount of a pharmaceutical composition comprising MGBG and at least one pharmaceutically acceptable excipient.

In certain embodiments, the pain is chosen from inflammatory pain, pain due to nerve injury, chronic pain, intractable cancer pain, complex regional pain syndrome, neuropathic pain, surgical or post-surgical pain, dental pain, pain resulting from dermal injury, lower back pain, headaches, migraine, tactile allodynia, and hyperalgesia. In certain embodiments, the pain is chronic. In other embodiments, the pain is acute. In certain embodiments, the pain is inflammatory pain.

In certain embodiments, the administration of MGBG or its pharmaceutical composition is oral. In other embodiments, the administration is intravenous.

In certain embodiments, the administration is a combination of oral and intravenous. In certain embodiments, the first administration is oral and the second IV; in others the first is IV and the second oral; in either case, additional oral or IV dosing may follow. In certain embodiments, the pain is surgical or post-surgical pain. For example, in certain embodiments, the pre-surgical administration is oral and the peri-surgical administration is IV; in others the pre-surgical administration is IV, the pre-surgical administration is also IV, and the post-surgical administration is oral. In either case, additional oral or IV dosing may follow. In certain embodiments, the pre-, peri-, and post-surgical administration is IV.

Also provided herein is a method of treatment of a condition in a subject in need thereof comprising the administration of
an oral pharmaceutical composition comprising MGBG and at least one pharmaceutically acceptable excipient; and
another therapeutic agent.

In certain embodiments, the MGBG is delivered in a therapeutically effective amount. In other embodiments, the MGBG is delivered in a subtherapeutic amount. In certain embodiments, the other therapeutic agent is delivered in a therapeutically effective amount. In other embodiments, the other therapeutic agent is delivered in a subtherapeutic amount. In certain embodiments, the MGBG and the other therapeutic agent are delivered together in amounts which would individually be subtherapeutic but which together are therapeutically effective. In other embodiments, the MGBG and the other therapeutic agent are delivered together in amounts which are individually therapeutically effective.

Additionally provided herein is a method of treating a condition. The method comprises administering to a subject in need of such treatment an effective amount of MGBG, a salt of MGBG, a protected derivative of MGBG, or a polyamine analog or polyamine biosynthesis inhibitor or a salt, a protected derivative, or a stereoisomer thereof, wherein the condition is chosen from Crohn's disease, Parkinson's disease, inflammatory bowel disorder, multiple sclerosis (MS), amyotrophic lateral sclerosis (ALS), hepatitis, HBV, HCV, nephritis, cerebritis, glomerulonephritis, rheumatoid arthritis, type 2 diabetes, cardiac fibrosis and angiotensin type II associated hypertension, osteoporosis, a mast cell produced IgE mediated hypersensitivity immune reaction, peripheral sensory neuropathy associated with HIV infection or diabetes mellitus, asthma, autism, dermatomyositis, frailty, obesity, primary biliary cirrhosis, primary sclerosing cholangitis, post-radiation syndrome, psoriatic arthritis, sarcoidosis, scleroderma with or without pulmonary fibrosis, a kidney related autoimmune condition, diabetic nephropathy, a diabetic vascular complication, and a lymphoproliferation related autoimmune condition.

Additionally provided herein is a method of decreasing differentiation of macrophages from monocytes, comprising contacting a monocyte with an effective amount of an agent that inhibits S-adenosyl methionine decarboxylase or inhibits polyamine biosynthesis in the monocyte. In certain embodiments the agent is MGBG, or a salt or protected derivative thereof.

In one embodiment, the agent is capable of inhibiting SAMDC or any pathway containing AMD I, e.g., any entity upstream or downstream of a pathway containing SAMDC, especially any pathway containing SAMDC and associated with adenosine production. In another embodiment the agent is capable of inhibiting polyamine biosynthesis or any pathway involved in polyamine biosynthesis. In general, a pathway containing SAMDC or adenosine is understood to refer to a pathway in which either SAMDC or adenosine is involved, including, for example, as a substrate, catalyst, product or by-product.

The agent can be any kind of known or later discovered agent that can inhibit the activity of the enzyme S-adenosyl methionine decarboxylase, can inhibit polyamine biosynthesis in, for example, a cell. In one embodiment, the agent is a chemical agent, including, but not limited to, organic molecules and salts, protected derivatives and stereoisomers thereof, inorganic molecules or various ionic or elemental entities.

Compounds for use in the methods and compositions disclosed herein include polyamine analogs and polyamine biosynthesis inhibitors, as well as salts, prodrugs, solvates, anhydrous forms, protected derivatives, structural isomers, stereoisomers, amino acid conjugates, and porphyrin conjugates thereof. Any polyamine analog is suitable for use in the methods of the present invention.

Exemplary polyamine analogs used in the methods of the invention include compounds of the structural formulas 1, 2, 3, 4, 5, 6, and 7 and the corresponding stereoisomers, salts, and protected derivatives thereof.

Formula 1 has the structure

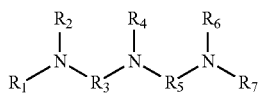

wherein $R_1$, $R_2$, $R_4$, $R_6$ and $R_7$ are independently chosen from hydrogen, alkyl and aryl; and $R_3$ and $R_5$, are alkyl groups.

Formula 2 has the structure

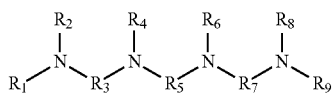

wherein $R_1$, $R_2$, $R_4$, $R_6$, $R_8$, and $R_9$ are independently chosen from hydrogen, alkyl and aryl; and $R_3$, $R_5$ and $R_7$ are alkyl groups.

Formula 3 has the structure

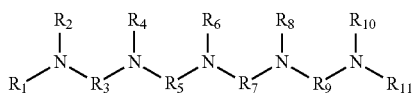

wherein $R_1$, $R_2$, $R_4$, $R_6$, $R_{10}$ and $R_{11}$ are independently chosen from hydrogen, alkyl and aryl; and $R_3$, $R_5$, $R_7$ and $R_9$ are alkyl groups.

Formula 4 has the structure

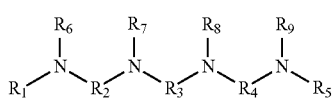

wherein $R_1$ and $R_5$ are independently chosen from methyl, ethyl, n-propyl, and isopropyl;

$R_2$, $R_3$, and $R_4$ are independently chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl; and $R_6$, $R_7$, $R_8$ and $R_9$ are independently chosen from hydrogen, methyl, and ethyl;

Formula 5 has the structure

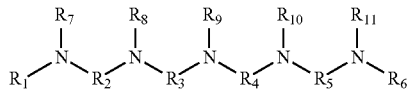

wherein $R_1$ and $R_6$ are independently chosen from methyl, ethyl, n-propyl, and isopropyl;

$R_2$, $R_3$, $R_4$ and $R_5$ are independently chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_3$-$C_{10}$ aryl-$C_1$-$C_6$ alkyl; and $R_7$, $R_8$, $R_9$, $R_{10}$ and $R_{11}$ are independently chosen from hydrogen, methyl, and ethyl.

In another embodiment, the polyamine analogs are compounds of the structures 2 and 3, wherein $R_3$, $R_5$, $R_7$ and $R_9$ are independently $(CH_2)_x$ groups;

x is an integer from 2 to 6; and $R_4$, $R_6$ and $R_8$ are hydrogen atoms.

In yet another embodiment, the polyamine analogs are compounds of the structures 2 and 3, wherein $R_3$, $R_5$, $R_7$ and $R_9$ are independently $(CH_2)_x$ groups;

x is an integer from 2 to 6;

$R_4$, $R_6$ and $R_8$ are hydrogen atoms;

$R_1$ and $R_{10}$ are alkyl groups; and $R_2$ and $R_{11}$ are hydrogen atoms.

In yet another embodiment, the polyamine analogs are compounds of the structures 2 and 3, wherein $R_3$, $R_5$, $R_7$ and $R_9$ are independently $(CH_2)_x$ groups;

x is an integer from 2 to 6;

$R_4$, $R_6$ and $R_8$ are hydrogen atoms;

$R_1$ and $R_{10}$ are alkyl groups;

$R_2$ and $R_{11}$ are hydrogen atoms; and the polyamine analogs have a molecular weight less than 500.

Further embodiments of compounds of the structure 4 include those wherein $R_6$, $R_7$, $R_8$ and $R_9$ are hydrogen.

In other embodiments, $R_1$ and $R_5$ are ethyl.

In yet further embodiments, $R_6$, $R_7$, $R_8$ and $R_9$ are hydrogen; and $R_1$ and $R_5$ are ethyl.

In yet further embodiments, $R_2$ and $R_4$ are independently chosen from $C_1$-$C_6$ alkyl; and $R_3$ is chosen from $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

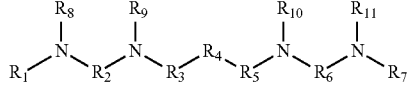

wherein $R_4$ is chosen from $C_2$-$C_6$ n-alkenyl, $C_3$-$C_6$ cycloalkyl, $C_3$-$C_6$ cycloalkenyl, and $C_3$-$C_6$ aryl;

$R_3$ and $R_5$ are independently chosen from a single bond, $C_1$-$C_6$ alkyl, and $C_1$-$C_6$ alkenyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, and $C_3$-$C_6$ aryl;

$R_1$ and $R_7$ are independently chosen from hydrogen, $C_1$-$C_6$ alkyl, and $C_2$-$C_6$ alkenyl; and $R_8$, $R_9$, $R_{10}$, and $R_{11}$ are hydrogen.

In certain embodiments of the compounds of formula 6, $R_1$ and $R_7$ are independently chosen from $C_1$-$C_6$ alkyl and $C_2$-$C_6$ alkenyl.

Additional polyamine analogs useful in the present invention include compounds of the formula 7, and the corresponding stereoisomers, salts, and protected derivatives thereof:

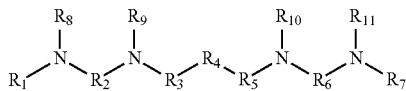

wherein $R_4$ is chosen from $C_1$-$C_6$ n-alkyl and $C_1$-$C_6$ branched alkyl;

$R_3$ and $R_5$ are independently chosen from a single bond or $C_1$-$C_6$ alkyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are hydrogen.

In certain embodiments of the compounds of formula 7
$R_2$ and $R_7$ are independently chosen from $C_1$-$C_6$ alkyl or $C_2$-$C_6$ alkenyl;

$R_4$ is chosen from $C_1$-$C_6$ saturated n-alkyl and $C_1$-$C_6$ saturated branched alkyl; and $R_3$ and $R_5$ are independently chosen from a single bond and $C_1$-$C_6$ saturated n-alkyl.

According to another embodiment of the present invention, the agent is a chemical moiety that inhibits the activity of S-adenosyl methionine decarboxylase, inhibits polyamine biosynthesis, and/or increases the activity of adenosine.

Examples of such moieties include, but are not limited to, those listed in Table 1. Irrespective of the form of the moiety listed in Table 1, it is understood that it includes, as applicable, a salt, protected derivative, and stereoisomer thereof.

TABLE 1

| Compound | Official Name (Not IUPAC) | Pub Chem ID |
| --- | --- | --- |
| Decarboxylated SAM | s-adenosyl-3-methylthiopropylamine | 5351154 |
| Mitoguazone or "MGBG" | Methylglyoxal bis(guanylhydrazone) | 9561662 |
| EGBG | Ethylglyoxal bis(guanylhydrazone) | 2354 |
| Berenil | Diminazene or Diminazene aceturate | 4735 |
| Pentamidine | 4-[5-(4-carbamimidoylphenoxy)pentoxy] benzenecarboximidamide | |
| | 5'-(Dimethylsulphino)-5'-deoxyadenosine | |
| | S-adneosyl-4-methylthiobutyrate | |
| | S-adenosyl-S-methyl-L-cysteine | |
| AMA | S-(5'-Deoxy-5'-adenosyl) methylthioethylhydroxylamine | |
| EMGBG | Ethylmethylglyoxal bis(guanylhydrazone) | |
| DEGBG | Diethylglyoxal bis(guanylhydrazone) | 9574151 |
| CGP-33'829 | 6-((2-carbamimidoylhydrazono)methyl) picolinimidamide | 5479208 |
| CGP-36'958 | | |
| CGP-39'937 | 2,2'-bipyridine-6,6'-bis(carboximidamide) | |
| CGP-48664 or CGP48664A or SAM 364A | 4-amidinoindan-1-one 2'-amidinohydrazone | 5486811 |
| AbeAdo or MDL-73811 | 5'-[[(Z)-4-amino-2-butenyl] methylamino]-5'-deoxyadenosine | 6436013 |
| MAOEA | 5'-deoxy-5'-[N-methyl-N-[2-(aminooxy)ethyl]amino]adenosine | 3081018 |
| MHZPA | 5'-deoxy-5'-[N-methyl-N-(3-hydrazinopropyl)amino]adenosine | 122092 |
| MHZEA | 5'-deoxy-5'-[(2-hydrazinoethyl)-methylamino]adenosine | |
| AdoMac | S-(5'-deoxy-5'-adenosyl)-1-ammonio-4-(methylsulfonio)-2cyclopentene | 3083364 |
| AdoMao | S-(5'-deoxy-5'-adenosyl)-1-aminoxy-4-(methylsulfonio)-2-cyclopentene | |
| APA | 1-Aminooxy-3-aminopropane | 65020 |
| AOE-PU | N-[2-aminooxyethyl]-1,4-diaminobutane | |
| AP-APA | 1-aminooxy-3-N-[3-aminopropyl]-aminopropane | |
| | 1,11-bis(ethyl)norspermine | |
| BES | 1,8-bis(ethyl)spermidine | |
| BES | 1,12-bis(ethyl)spermine | |
| DESPM | N1,N12-diethylspermine | |
| BE-3-3-3 | 1,11-bis(ethylamino)-4,8-diazaundecan | |
| BE-4-4-4 | 1,14-bis(ethylamino)-5,10-diazatetradecane | |
| DEHOP or DEHSPM | Diethylhomospermine, N1,N14-diethylhomospermine | |
| DENOP | diethyl-norspermine | |
| BE-4-4-4-4 | 1,19-bis(ethylamino)-5,10,15-triaza-nonadecane | |
| SL11037 | N-ethyl-N'-(2-(3'-ethylamino-propylamino methyl)-cis-cyclopropylmethyl)-propane 1,3-diamine tetrahydrochloride | |

TABLE 1-continued

| Compound | Official Name (Not IUPAC) | Pub Chem ID |
|---|---|---|
| SL11038 | N-ethyl-N'-(2-(3'-ethylamino-propylamino methyl)-trans-cyclobutylmethyl)-propane 1,3-diamine tetrahydrochloride | |
| SL11044 | N-ethyl-N'-(2-(3'-ethylamino-propylamino methyl)-transcyclopropylmethyl)-propane 1,3-diamine tetrahydrochloride | |
| SL11047 or SL47 | N,N'-bis(3-ethylaminopropyl)-cis-but-2-ene-1,4-diaminetetrahydrochloride | |
| SL11093 or SL93 | N,N'-(cyclopropane-1,2-diylbis(methylene))bis(N4-ethylbutane-1,4-diamine) | |

In yet another embodiment, the agent is a compound chosen from MGBG, MDL73811, CGP48664, Berenil, Pentamidine, SL47, and SL93, or a combination of two or more thereof. In yet another embodiment, the agent is MGBG, SL47 or SL93. In still another embodiment, two or more agents are used. The two or more agents can be used either sequentially or simultaneously.

MGBG is 1,1' [methylethanediylidene]dinitrilodiguanidine and is also known as methylglyoxal bis(guanylhydrazone), methyl-GAG, Me-G, and mitoguazone. As used herein, MGBG includes the free base and salts thereof. It is commonly, but not necessarily, used as a dihydrochloride. MGBG may be present as any one of the following isomers, or a tautomer and/or a syn/anti isomer thereof, mixture of one or more thereof:

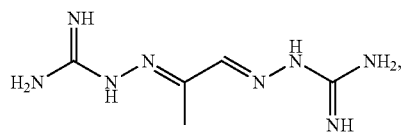

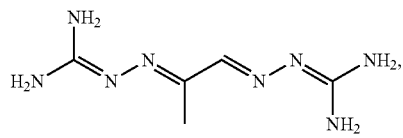

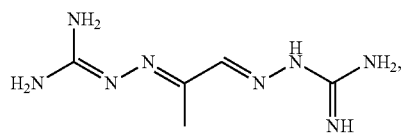

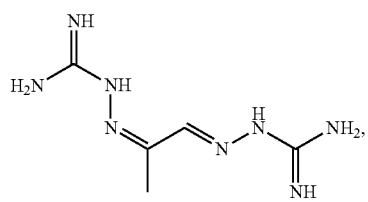

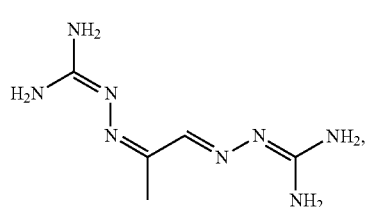

-continued

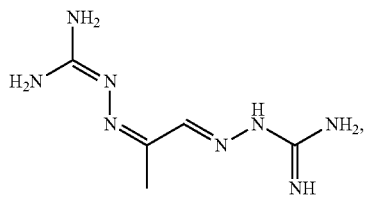

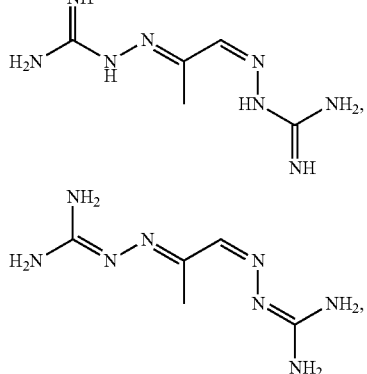

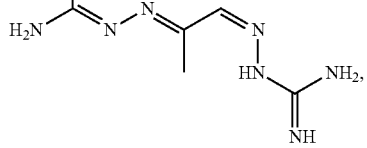

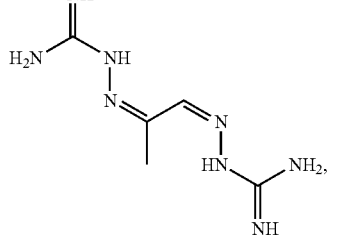

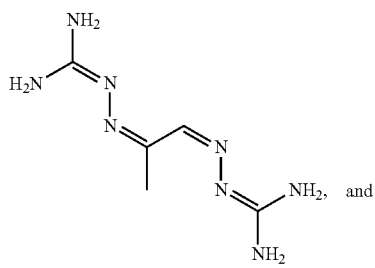

-continued

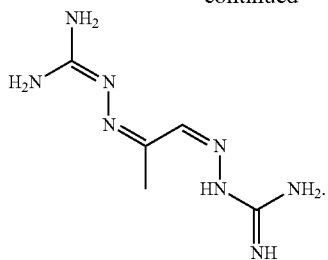

In certain embodiments, MGBG may be present one of the following isomers, or a tautomer and/or a syn/anti isomer thereof, mixture of one or more thereof:

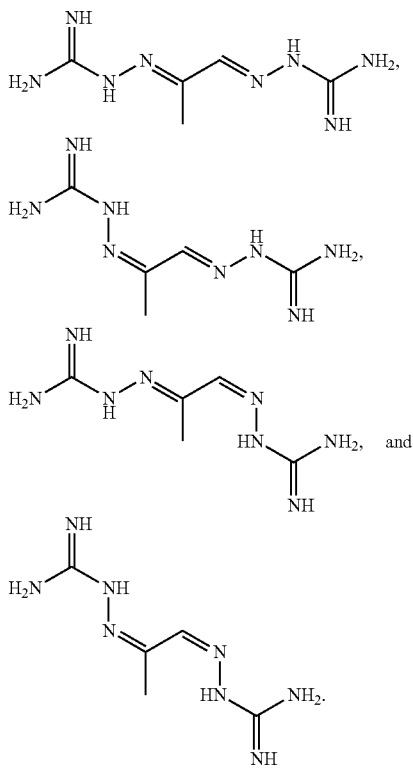

In certain embodiments, compounds have a structure chosen from Formulas 8a-8c:

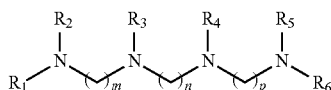
(8a)

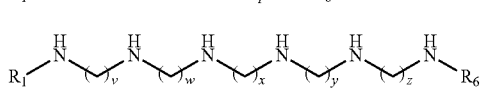
(8b)

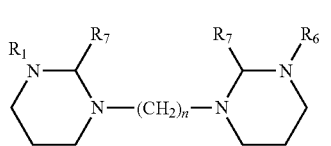
(8c)

$R_1$-$R_6$ are chosen from hydrogen, alkyl and aralkyl having from 1 to 12 carbon atoms, provided that, in formula (8a), $R_1$, and $R_6$ are not hydrogen;

$R_7$ chosen from hydrogen, alkyl, aryl and aralkyl having from 1 to 12 carbon atoms;

m, n, are each independently an integer from 3 to 6, inclusive; and v, w, x, y, and z are each independently an integer from 3 to 10, inclusive.

Additional disclosure may be found in WO98/10766, the disclosure of which is incorporated by reference as if written herein in its entirety, for example on pp. 3-4.

In certain embodiments, compounds have a structure of Formula 9a:

wherein

A is independently selected from the group consisting of $C_1$-$C_6$ alkyl, $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl;

B is independently selected from the group consisting of: a single bond, $C_1$$C_6$ alkyl, and $C_2$-$C_6$ alkenyl; and E is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl;

with the proviso that either at least one A moiety is selected from the group consisting of $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl, or at least one B moiety is selected from the group consisting of $C_2$-$C_6$ alkenyl; and all salts, hydrates, solvates, and stereoisomers thereof.

In another embodiment, the conformationally restricted polyamine analog is selected from among the group of compounds of the formula 9b:

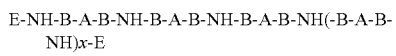

wherein:

A is independently selected from the group consisting of $C_1$-$C_6$ alkyl, $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl;

B is independently selected from the group consisting of: a single bond, $C_1$-$C_6$ alkyl, and $C_2$-$C_6$ alkenyl; and E is independently selected from the group consisting of hydrogen, $C_1$-$C_6$ alkyl, $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl;

x is an integer from 2 to 16;

with the proviso that either at least one A moiety is selected from the group consisting of $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl, or at least one B moiety is selected from the group consisting of $C_2$-$C_6$ alkenyl;

and all salts, hydrates, solvates, and stereoisomers thereof.

In another embodiment, x is 4,6, 8, or 10.

In another embodiment, x is 4. In another embodiment, x is 6.

In another embodiment, x is 8.

In another embodiment, x is 10.

In another embodiment, the conformationally restricted polyamine analog is selected from among the group of compounds of the formula 9c:

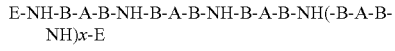

wherein:
A is independently selected from the group consisting of $C_1$-$C_6$ alkyl, $C_2$-$C_6$ alkenyl, $C_2$-$C_6$ alkynyl, $C_3$-$C_6$ cycloalkyl, $C_3$-$C_6$ aryl, and $C_3$-$C_6$ cycloalkenyl;
B is independently selected from the group consisting of: a single bond, $C_1$-$C_6$ alkyl, and $C_2$-$C_6$ alkenyl; and
E is independently selected from the group consisting of $C_1$-$C_6$ alkyl, $C_1$-$C_6$ alkanol, $C_3$-$C_6$ cycloalkanol, and $C_3$-$C_6$ hydroxyaryl, with the proviso that at least one E moiety be selected from the group consisting of $C_1$-$C_6$ alkanol, $C_3$-$C_6$ cycloalkanol, and $C_3$-$C_6$ hydroxyaryl; and
x is an integer from 0 to 16;
and all salts, hydrates, solvates, and stereoisomers thereof.

In another embodiment, the conformationally restricted polyamine analog is selected from among the group of compounds of the formula 9d:

wherein A is selected from the group consisting of $C_2$-$C_6$ alkene and $C_3$-$C_6$ cycloalkyl, cycloalkenyl, and aryl;
B is independently selected from the group consisting of a single bond and $C_1$-$C_6$ alkyl and alkenyl;
D is independently selected from the group consisting of $C_1$-$C_6$ alkyl and alkenyl, and $C_3$-$C_6$ cycloalkyl, cycloalkenyl, and aryl;
E is independently selected from the group consisting of hydrogen, $C_1$-$C_6$ alkyl and alkenyl; and all salts, hydrates, solvates, and stereoisomers thereof.

In another embodiment, the conformationally restricted polyamine analog is selected from macrocyclic polyamines of the formula 9e:

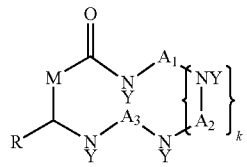

wherein
$A_1$, each $A_2$ (if present), and $A_3$ are independently selected from $C_1$-$C_8$ alkyl;
each Y is independently selected from hydrogen or $C_1$-$C_4$ alkyl;
M is selected from $C_1$-$C_4$ alkyl;
k is 0, 1, 2, or 3; and
R is selected from $C_1$-$C_{32}$ alkyl;
and all salts, hydrates, solvates, and stereoisomers thereof.
In additional embodiments, the Y group is hydrogen or —$CH_3$.
In another embodiment, $A_1$, each $A_2$ (if present), and $A_3$ are independently selected from $C_2$-$C_4$ alkyl.
In yet another embodiment, M is —CH2-.
In another embodiment, the conformationally restricted polyamine analog is selected from macrocyclic polyamine analogs of the formula 9f:

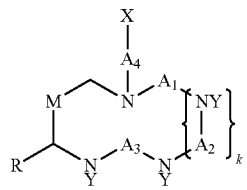

wherein
$A_1$, each $A_2$ (if present), and $A_3$ are independently selected from $C_1$-$C_8$ alkyl;
$A_4$ is selected from $C_1$-$C_8$ alkyl or null;
X is selected from —hydrogen, —Z, —CN, —$NH_2$, —C(=O)— $C_1$-$C_8$-alkyl, or —NHZ, with the proviso that when $A_4$ is null, X is hydrogen, —C(=O)— $C_1$-$C_8$-alkyl, or —Z;
Z is selected from the group consisting of an amino protecting group, an amino capping group, an amino acid, and a peptide;
each Y is independently selected from hydrogen or $C_1$-$C_4$ alkyl;
M is selected from $C_1$-$C_4$ alkyl;
k is 0, 1, 2, or 3; and
R is selected from $C_1$-$C_{32}$ alkyl;
and all salts, hydrates, solvates, and stereoisomers thereof.

In certain embodiments, $A_4$ is null.
In other embodiments, X is —Z, and —Z is hydrogen.
In other embodiments, X is —Z, and —Z is 4-morpholinocarbonyl.
In other embodiments, X is —Z and —Z is acetyl.
In other embodiments, X is —Z and —Z is t-Boc or Fmoc.
In other embodiments, Y is —CH3.
In other embodiments, M is —$CH_2$—.
In still further embodiments, k is 1.
In further embodiments, A, and $A_3$ are —$CH_2CH_2CH_2$—.
In still further embodiments, —$CH_2CH_2CH_2CH_2$—.
In still further embodiments, R is $C_{13}H_{27}$.
In yet further embodiments, one or more of the specific limitations on $A_4$, X, Z, Y, M, k, $A_1$, $A_3$, and R are combined.
In further embodiments of macrocyclic polyamine analog compounds,
$A_4$ is $C_1$-$C_8$ alkyl;
X is —NHZ; and
Z is selected from one of the 20 genetically encoded amino acids (alanine, cysteine, aspartic acid, glutamic acid, phenylalanine, glycine, histidine, isoleucine, lysine, methionine, asparagine, proline, glutamine, arginine, serine, threonine, valine, tryptophan, tyrosine), a peptide of the formula acetyl-SKLQL-, a peptide of the formula acetyl-SKLQ-I3-alanine-, or a peptide of the formula acetyl-SKLQ-.

In these cases, where Z is an amino acid or peptide, the therapeutic agent to be used is a polyamine-amino acid conjugate or polyamine-peptide conjugate.

In one embodiment, the only conformational restriction of the polyamine analog is due to a carbon-carbon double bond (an ethenyl group, C=C) in the molecule.

In another embodiment, the only conformational restriction of the polyamine analog is due to a cycloalkyl group, such as a cyclopropyl group, in the molecule.

Compounds include, but are not limited to:
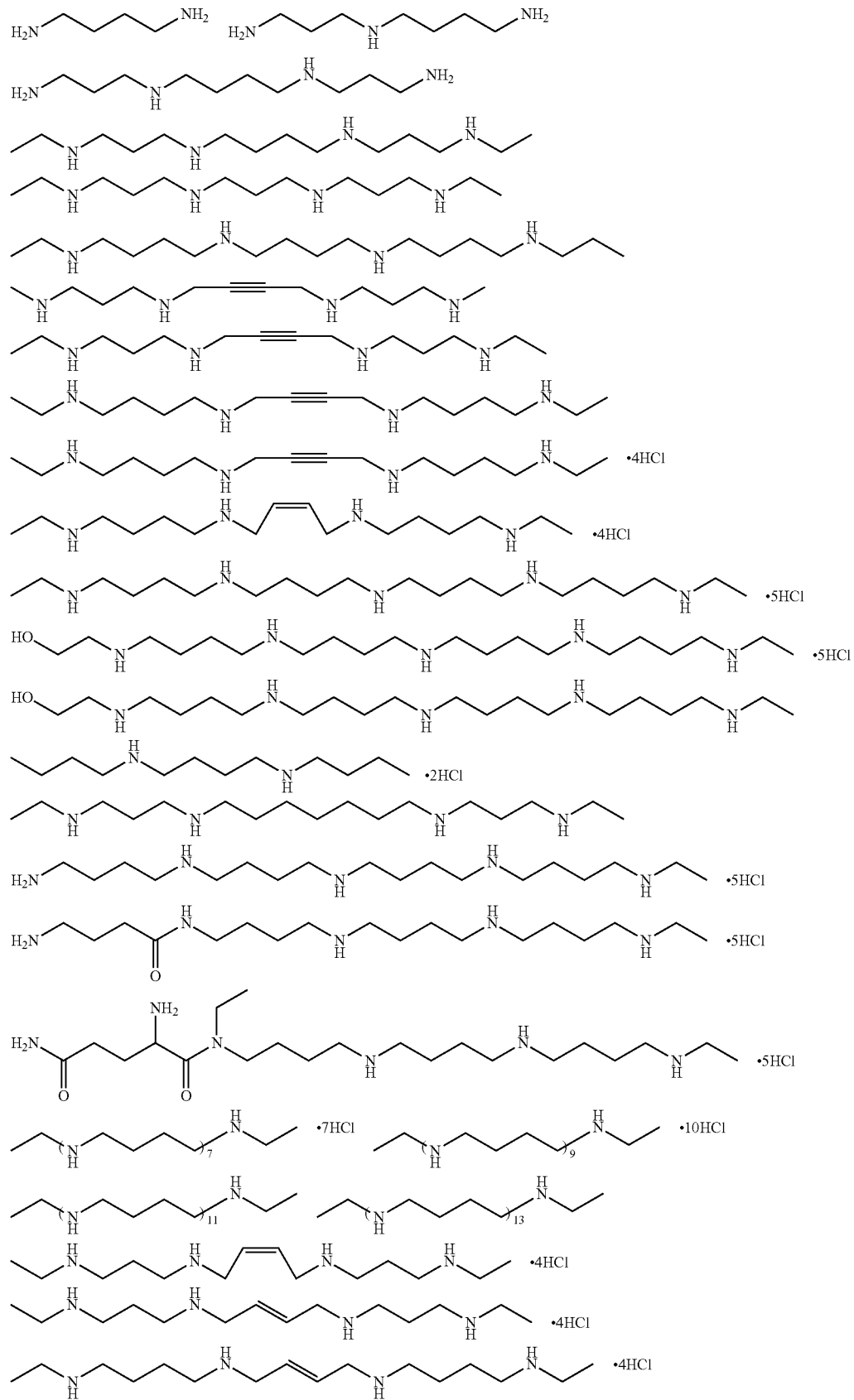

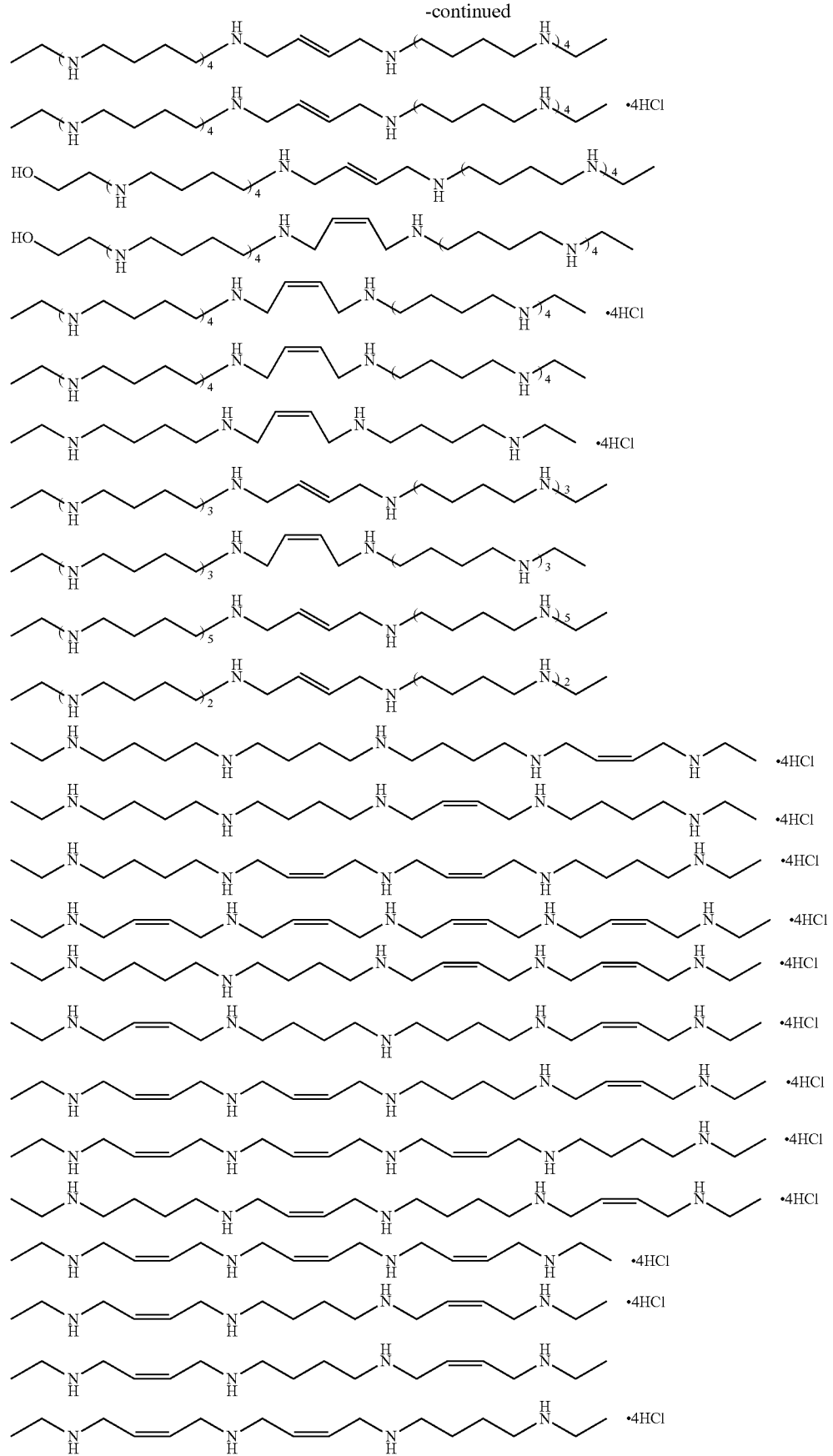

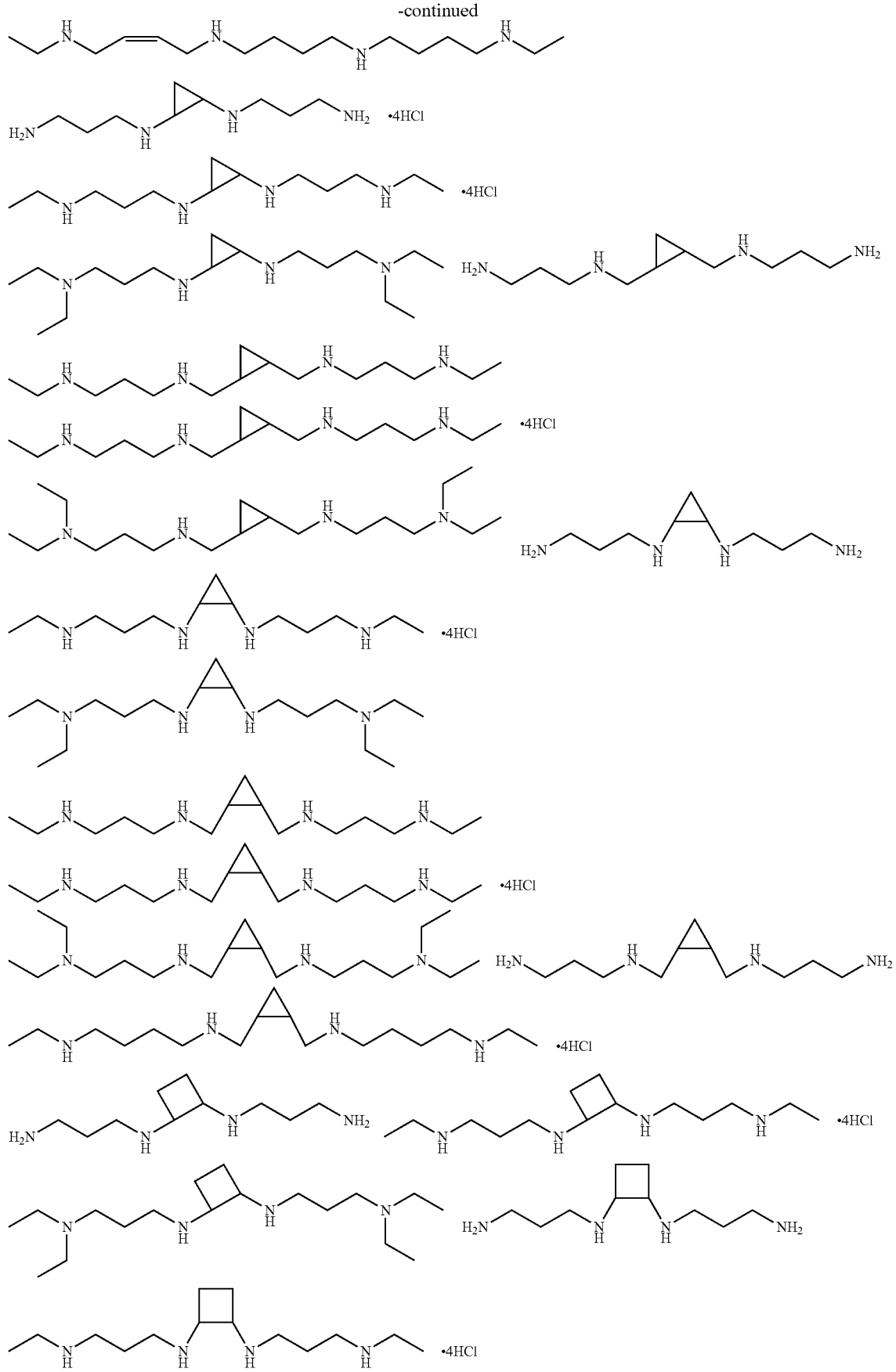

-continued
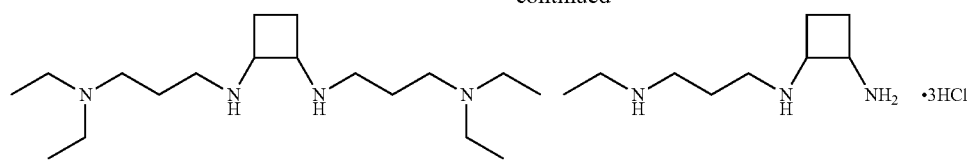
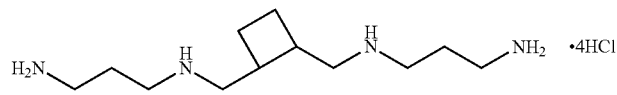
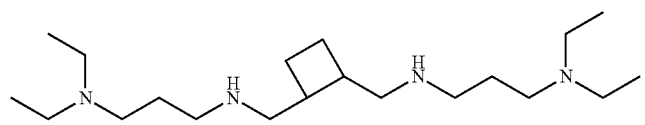
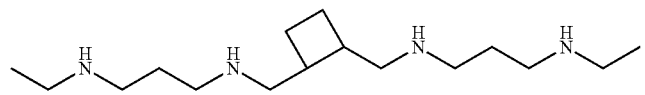
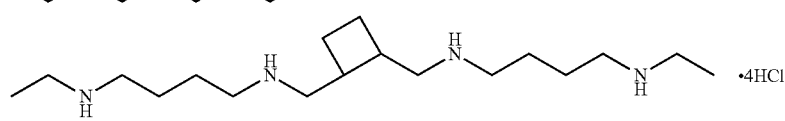
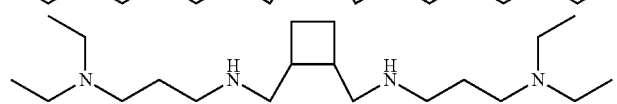
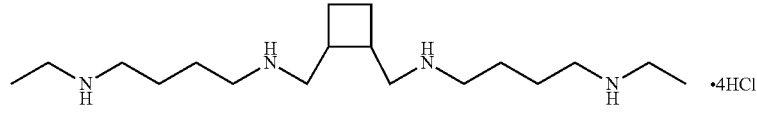
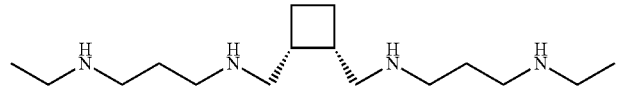
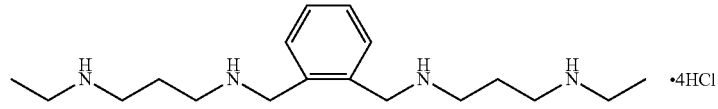
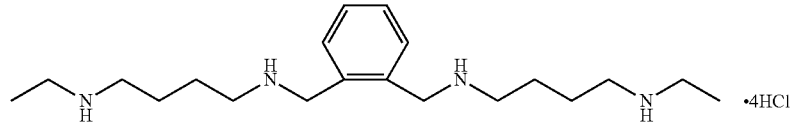
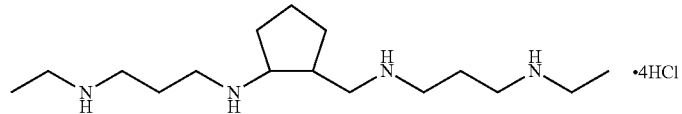
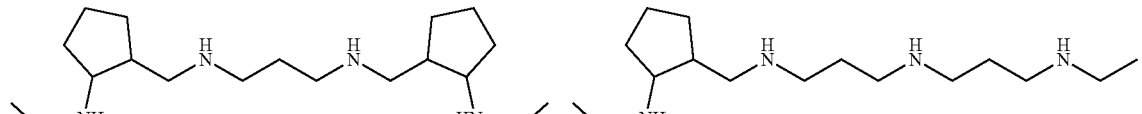
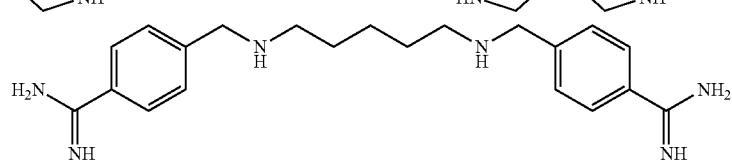

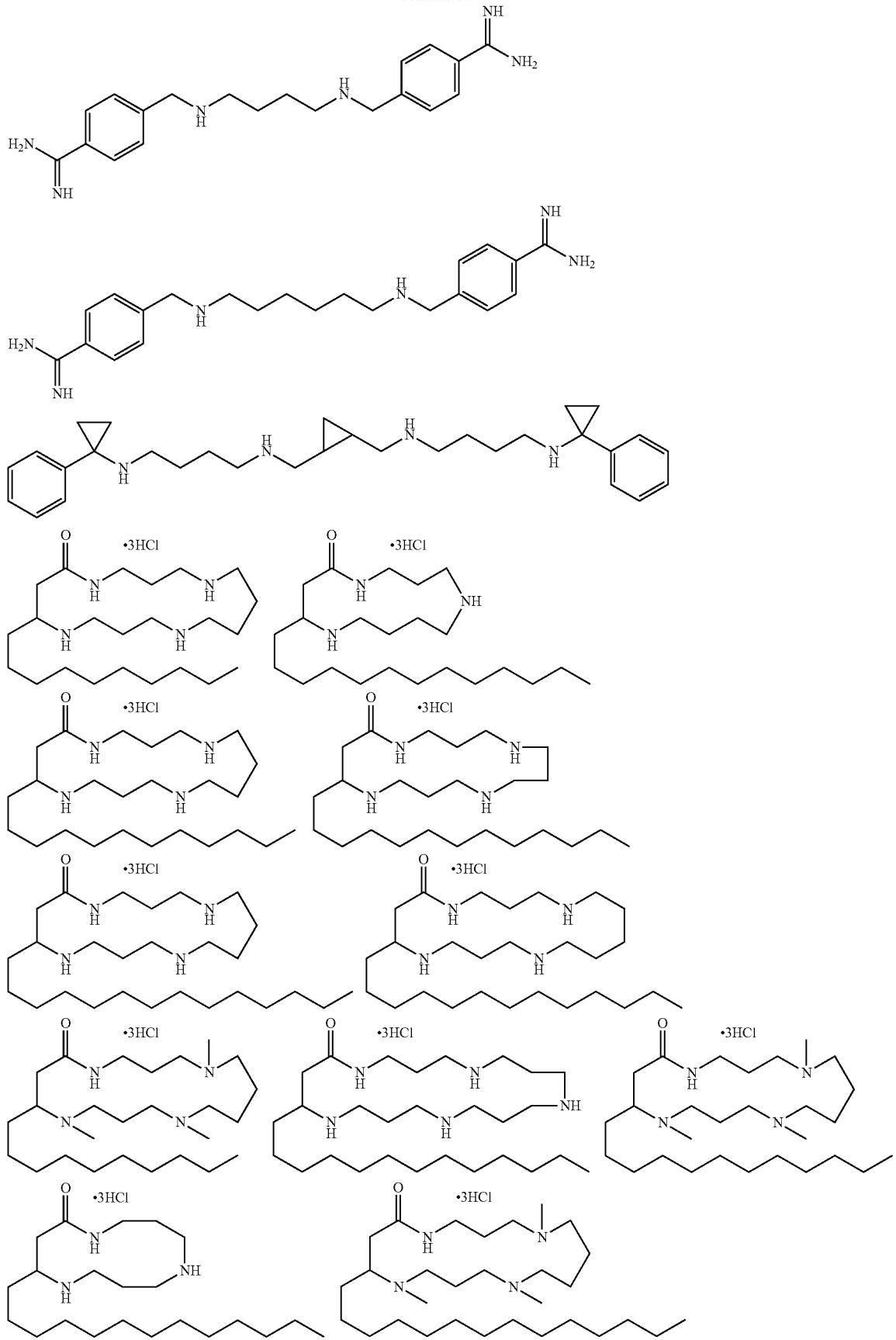

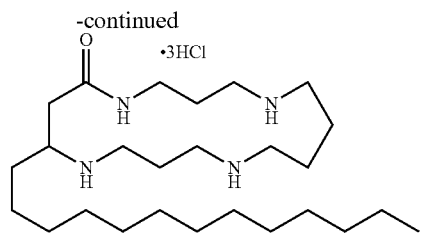
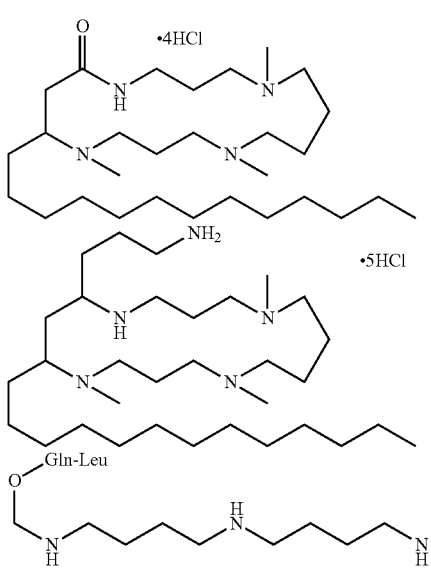
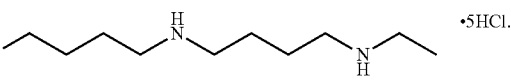

Additional disclosure may be found in WO2007/040535, the disclosure of which is incorporated by reference as if written herein in its entirety.

Additional analogs and derivatives include those encompassed by the following formula 10a:

R—X-polyamine wherein
R is selected from H or from the group of a straight or branched C1-50 saturated or unsaturated aliphatic, carboxyalkyl, carbalkoxyalkyl, or alkoxy; a C1-8 alicyclic; a single or multiring aryl substituted aliphatic; an aliphatic-substituted single or multiring aromatic; a single or multiring heterocyclic; a single or multiring heterocyclic 25 aliphatic; a C1-10 alkyl; an aryl sulfonyl; or cyano;

X may be —CO—, —SO$_2$, or —CH$_2$—, and

"polyamine" may be any naturally occurring, such as putrescine, spermine or spermidine, or synthetically produced polyamine Preferably, R is at least about C5, at least about C10, at least about C11, at least about C12, at least about C13, at least about C14, at least about C15, at least about C16, at least about C17, at least about C18, at least about C19, at least about C20, or at least about C22.

The linkage between X and the polyamine may be direct, wherein there are no atoms between X and the nitrogen of the amine group of the polyamine, or indirect, where there may be one or more atoms between X and the nitrogen of the amine group of the polyamine. The linkage. between X and the polyamine may occur via any amino group within the polyamine, although a primary amino group is used in preferred embodiments of the invention.

In preferred embodiments of the invention where the linkage between X and the polyamine is indirect, the intervening one or more atoms are preferably those of an amino acid or a derivative thereof. In particularly preferred embodiments of this type, the intervening one or more atoms are those of lysine, aspartic acid, glutamic acid, ornithine, or 2,4-diaminobutyric acid. Preferred compounds of this type may be represented as in Formula 10b:

R—X-L-polyamine wherein
R is a straight or branched C10-50 saturated or unsaturated aliphatic, carboxyalkyl, carbalkoxyalkyl, or alkoxy; a C1-8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; an aryl sulfonyl;

X is —CO—, —SO$_2$—, or —CH$_2$—; and

L is a covalent bond or a naturally occurring amino acid, ornithine, 2,4-diaminobutyric acid, or derivatives thereof.

The analogs and derivatives of the invention, may be optionally further substituted at one or more other positions of the polyamine. These include, but are not limited to, internal nitrogen and/or internal carbon atoms. In one aspect of the invention, preferred substituents are structures that increase polyamine transport inhibition, binding affinity or otherwise enhance the irreversibility of binding of the compound to a polyamine binding molecule, such as the polyamine transporter, an enzyme or DNA. Such additional substituents include the aziridine group and various other aliphatic, aromatic, mixed aliphatic-aromatic, or heterocyclic multi-ring structures. Reactive moieties which, like aziridine, bind covalently to a polyamine transporter or another polyamine binding molecule, are also within the scope of this invention. Examples of reactive groups that react with nucleophiles to form covalent bonds include chloro-, bromo- and iodo-acetamides, sulfonylfluorides, esters, nitrogen mustards, etc. Such reactive moieties are used for affinity labeling in a diagnostic or research context, and may contribute to pharmacological activity in inhibiting polyamine transport or polyamine synthesis. The reactive group can be a reactive photoaffinity group such as an azido or benzophenone group. Chemical agents for photoaffinity labeling are well-known in the art (Flemming, S. A., *Tetrahedron* 1995,51, 12479-12520).

A preferred aspect of the invention relates to a polyamine analog or derivative that is a highly specific polyamine transport inhibitor with pharmaceutical utility as an anticancer chemotherapeutic. One class of a polyamine analog or derivative of the invention that binds to a polyamine-binding site of a molecule and/or inhibits polyamine transport, is described by the following formula 10c:

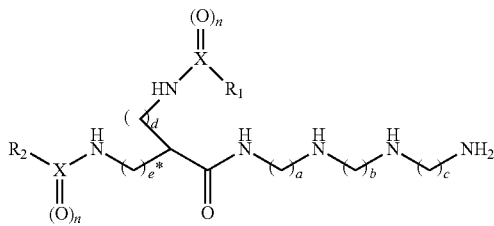

wherein
a, b, and c independently range from 1 to 10;
d and e independently range from 0 to 30;
each X is independently either a carbon (C) or sulfur (S) atom, and
$R_1$ and $R_2$ are as described below, or each of $R_1X(O)n-$ and of $R_2X(O)n-$ are independently replaced by H; and
* denotes a chiral carbon position;
and with the provisos that
if X is C, then n is 1;
if X is S, then n is 2; and
if X is C, then the X(O) group may be $CH_2$ such that n is 0.

In the above formula, $R_1$ and $R_2$ are independently selected from H or from the group of a straight or branched C1-50 saturated or unsaturated aliphatic, carboxyalkyl, carbalkoxyalkyl, or alkoxy; a C1-8 alicyclic; a single or multiring aryl substituted aliphatic; an aliphatic-substituted single or multiring aromatic; a single or multiring aromatic or saturated heterocyclic; a single or multiring heterocyclic aliphatic; a C1-10 alkyl; an aryl sulfonyl; or cyano.

Examples of heterocyclic rings as used herein include, but are not limited to, pyrrole, furan, thiophene, imidazole, oxazole, thiazole, pyrazole, 3-pyrroline, pyrrolidine, pyridine, pyrimidine, purine, quinoline, isoquinoline, and carbazole.

All of the above described aliphatic, carboxyalkyl, carbalkoxyalkyl, alkoxy, 30 alicyclic, aryl, aromatic, and heterocyclic moieties may, of course, also be optionally substituted with 1-3 substituents independently selected from halo (fluoro, chloro, bromo or iodo), lower alkyl (1-6C) and lower alkoxy (1-6C).

As used herein, carboxyalkyl refers to the substituent —R'—COOH wherein R' is alkylene; and carbalkoxyalkyl refers to —R'—COOR wherein R' and R are alkylene and alkyl respectively. In preferred embodiments, alkyl refers to a saturated straight- or branched-chain hydrocarbyl radical of 1-6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent. Aryl or alkyl sulfonyl moieties have the formula $SO_2R$ and alkoxy moieties have the formula —O—R, wherein R is alkyl, as defined above, or is aryl wherein aryl is phenyl, optionally substituted with 1-3 substituents independently selected from halo (fluoro, chloro, bromo or iodo), lower alkyl (1-6C) and lower alkoxy (1-6C).

A preferred group of compounds encompassed by the above is where d is 4 and e is 0.

An additional class of a polyamine analog or derivative of the invention that binds to a polyamine-binding site of a molecule and/or inhibits polyamine transport, is described by the following formula 10d:

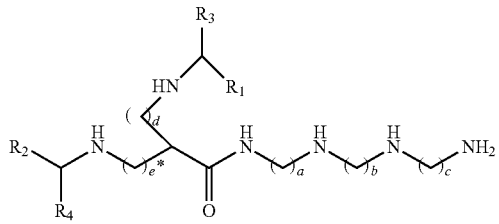

wherein
a, b, and c independently range from 1 to 10;
d and e independently range from 0 to 30;
$R_1$ and $R_2$ are defined as above for formula 8c and
$R_3$ and $R_4$ are independently selected from organic substituents including —$CH_3$ and as defined above for $R_1$ and $R_2$ in formula 8c above. This grouping of analogs is produced by reductive amination of the free amino precursor with a ketone.

In one preferred embodiment of the invention, $R_1$ and $R_2$ are identical and as described for formula 8c. Positions $R_3$ and $R_4$ may also be identical, and all of $R_1$ through $R_4$ may also be identical. Additionally, each of positions $R_1$, $R_2$, $R_3$, and $R_4$ in formula 8d may also be independently H.

In an additional aspect of the invention the proximal and/or the distal amino group relative to the polyamine (such as spermine) can be di-alkylated to form tertiary amines. These materials can be synthesized by reductive amination with a large excess of the carbonyl component. Additionally, these materials may be produced by a conjugate addition of the amine precursor to an α,β-unsaturated carbonyl or α,β-unsaturated nitrile.

Each of $R_1$, $R_2$, $R_3$, and $R_4$ can be independently varied and are as defined as above for formula III. Each of $R_1$, $R_2$, $R_3$, and $R_4$ may also be independently H. The values of a, b, c, d and e are as described above for formula 8d. This aspect of the invention is depicted in the following formula 10e:

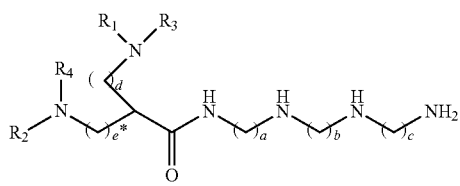

In a further aspect of the invention, compounds which lack the proximal or distal amino group on the acyl portion of the molecule are also provided. These are represented by formula 10f:

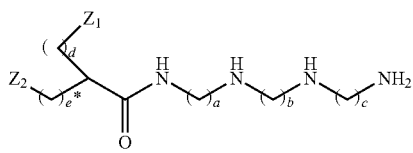

wherein
$Z_1$ is $NR_1R_3$ and $Z_2$ is selected from —$R_1$, —$CHR_1R_2$ or —$CR_1R_2R_3$ (wherein $R_1$, $R_2$, and $R_3$ are as defined above for formula 8c); or $Z_2$ is $NR_2R_4$ and $Z_1$ is selected from —$R_1$, —$CHR_1R_2$ or —$CR_1R_2R_3$ (wherein $R_1$, $R_2$, and $R_3$ are as defined above for formula 8d). Values for a, b, and c independently range from 1 to 10; d and e independently range from 0 to 30. Compounds encompassed by formula V may be prepared by first coupling amino acid derivatives (modified to contain the non-amine containing Z group) to a polyamine followed by appropriate derivatization of the amine containing Z group. Chemistries for such reactions are known in the art and disclosed herein.

In preferred embodiments of the invention, positions $R_1$, $R_2$, $R_3$, and $R_4$, of all the formulas set forth above are independently selected from the following, where each of g, h, j, and k are independently selected from 0 to 15:

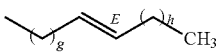

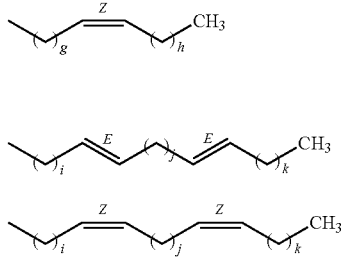

wherein E refers to "entgegen" and Z refers to "zusammen".

Compounds include, but are not limited to:

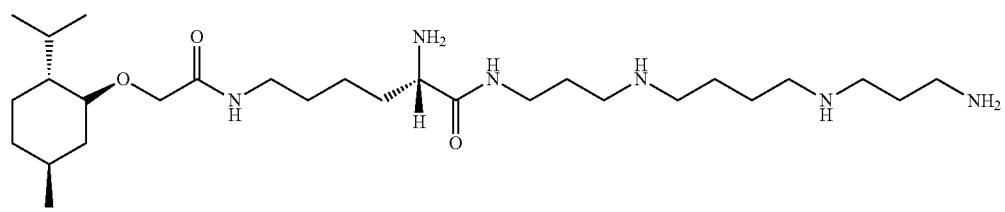

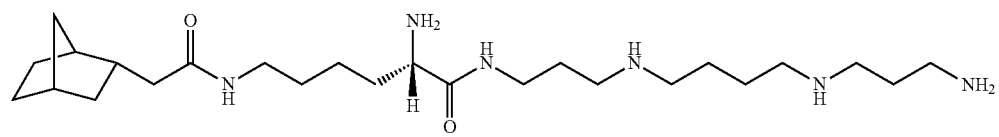

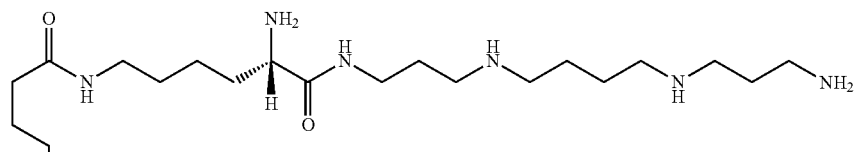

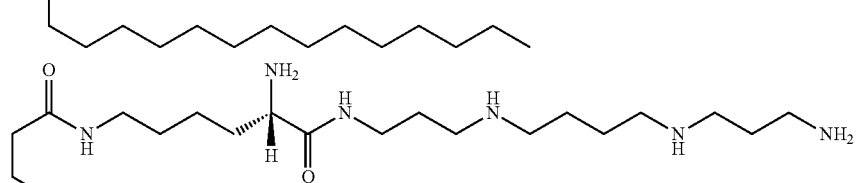

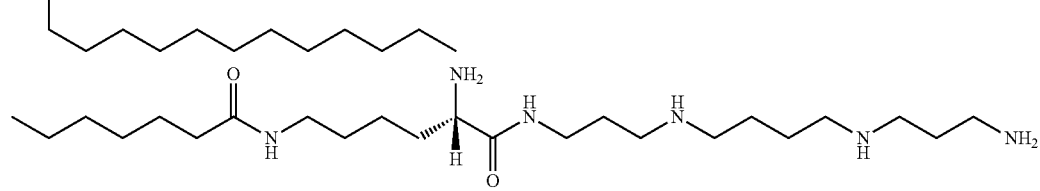

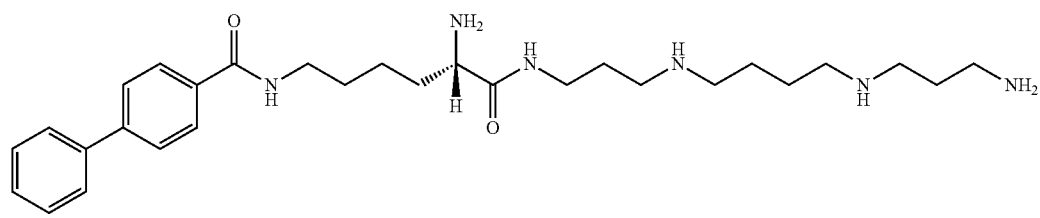

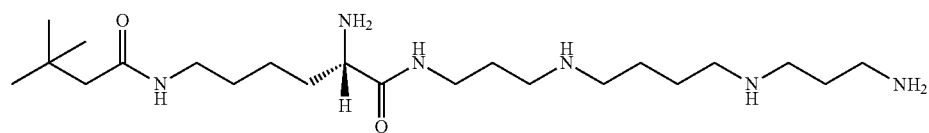

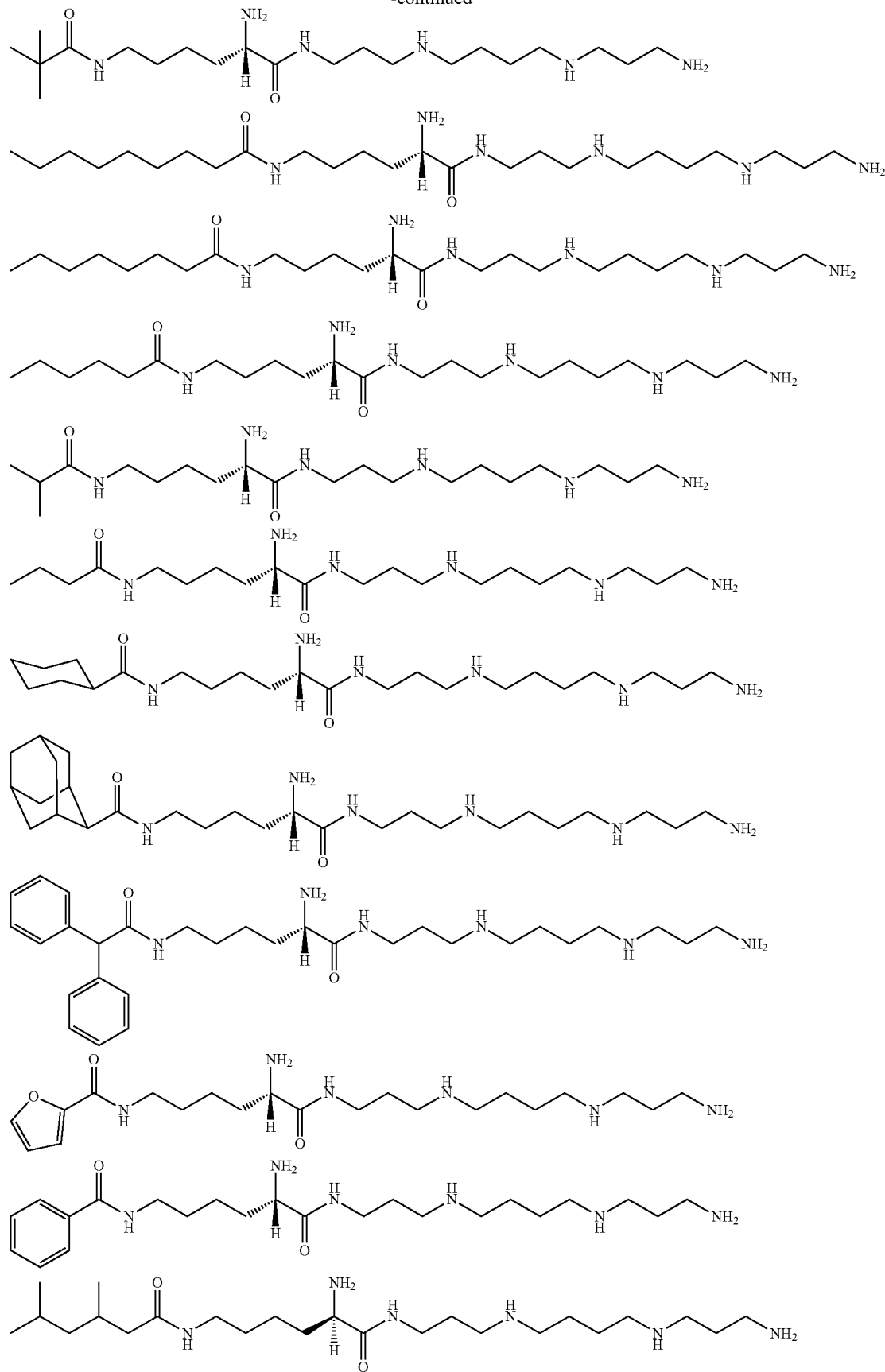

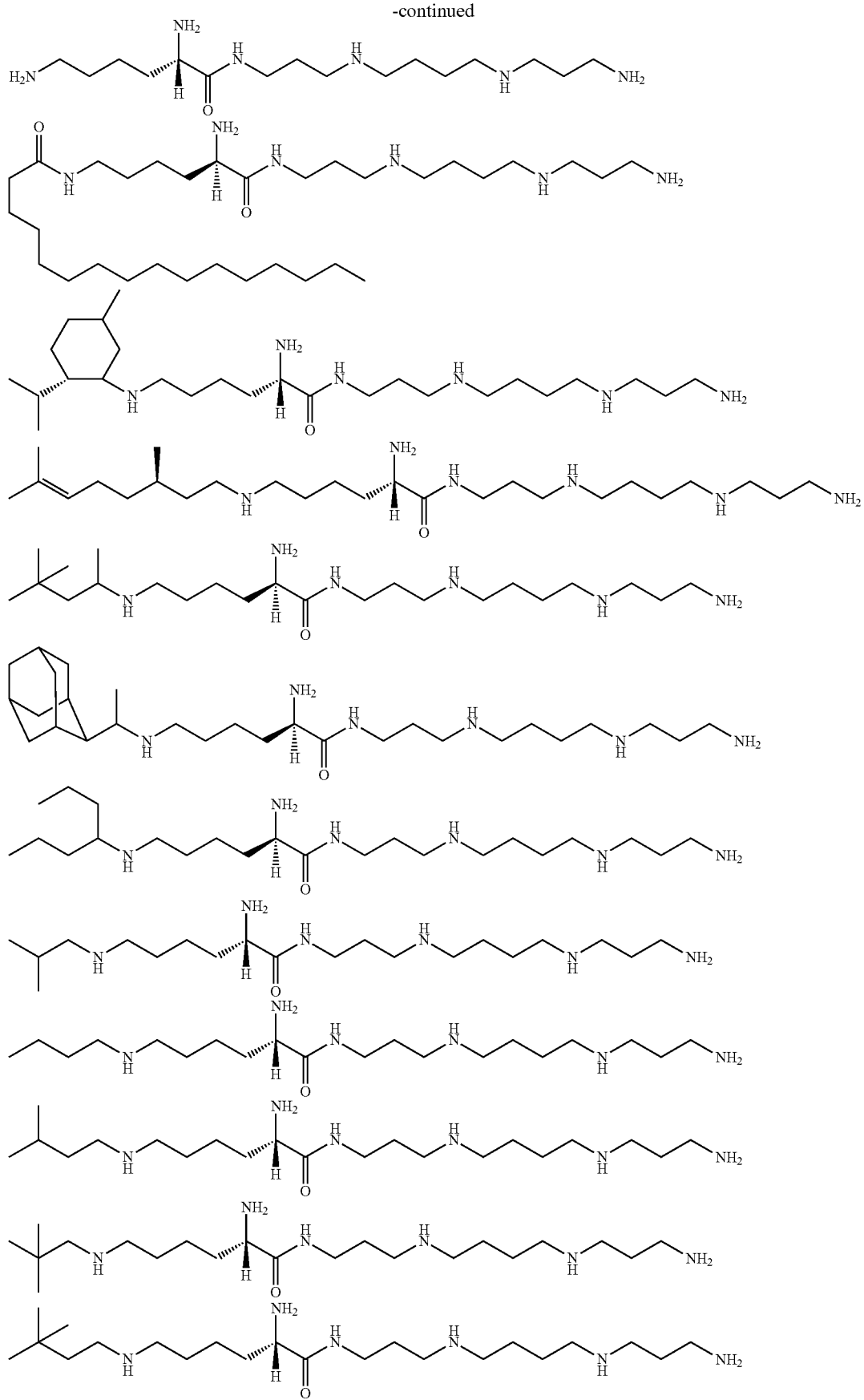

-continued

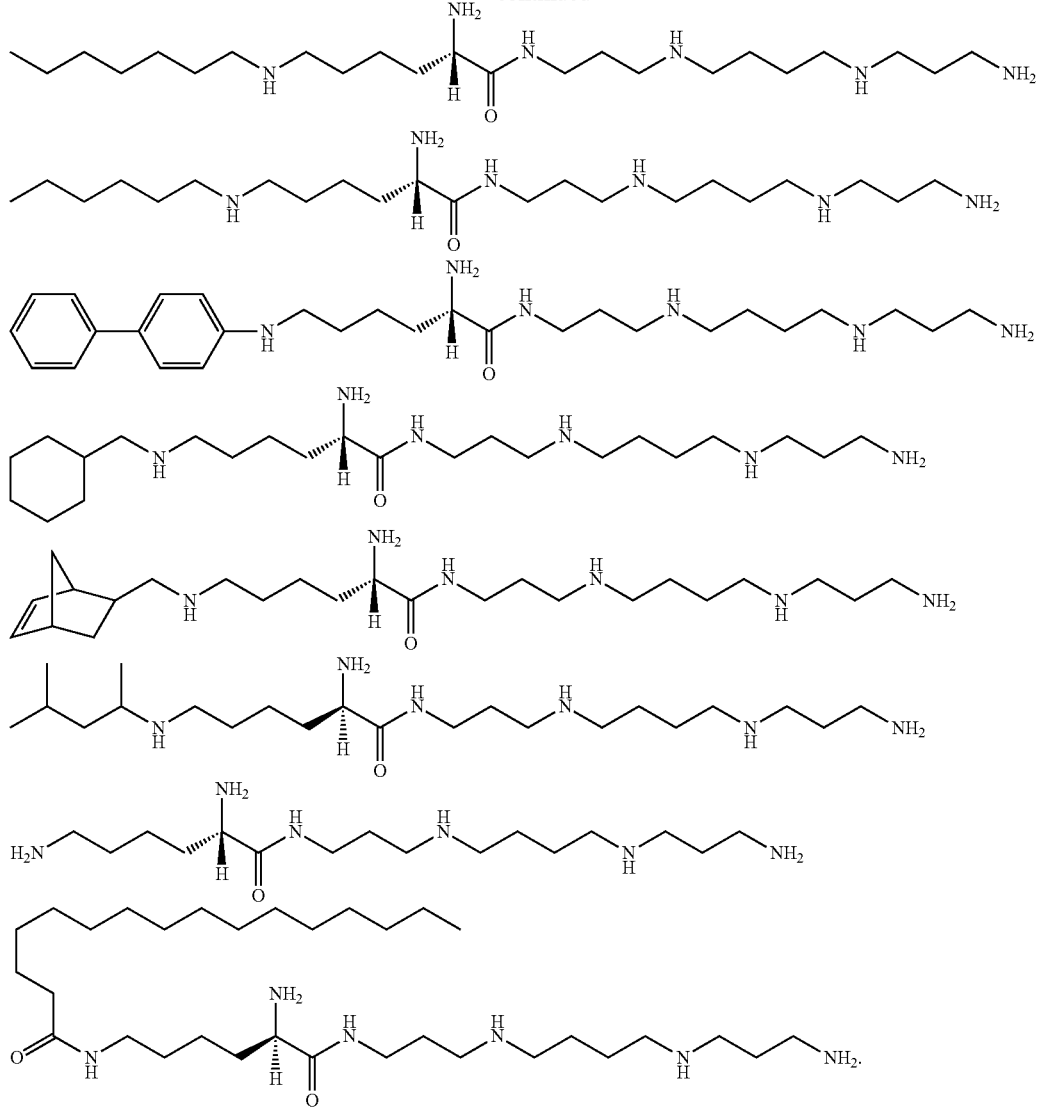

Additional disclosure may be found in WO2002/053519, the disclosure of which is incorporated by reference as if written herein in its entirety.

Additional analogs and derivatives include synthetic derivatives of original polyamines, wherein a carbon atom of said original polyamine comprises an amide group, said synthetic derivative inhibiting the cellular uptake of a natural polyamine by specifically binding a cellular transporter for said natural polyamine In certain embodiments, the carbon to which said amido group is located is between two internal nitrogen atoms of said original polyamine.

In certain embodiments, the synthetic derivative comprises a dimer of said original polyamine, the monomers of said dimer being linked together by a spacer side chain anchored to the amido group of each monomer.

In certain embodiments, the original polyamine is selected from the group consisting of putrescine, spermidine and spermine.

In certain embodiments, the original polyamine is spermine.

In certain embodiments, said synthetic derivative has the following general formula 11a:

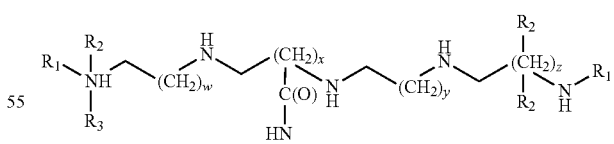

in which $R_1$ and $R^1_1$ independently represent a hydrogen atom or an alkyl group having 1 to 2 carbon atoms, $R_2$, $R^1_2$, or $R_3$ and $R^1_3$ independently represent a hydrogen atom or a methyl group, w and z independently represent an integer of 2 or 3, x represents an integer from 0 to n, n represents an integer from 3 to 6, the sum of x and y equals n, and S represents a hydrogen atom or a molecule which cannot be captured by said natural polyamine transporter.

In certain embodiments, said monomer has the following general formula 11b:

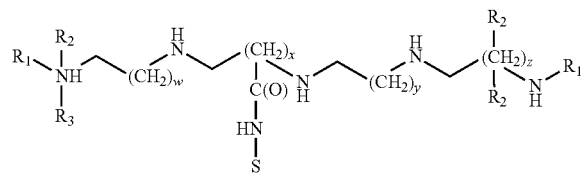

in which $R_1$ and $R^1_1$ independently represent a hydrogen atom or an alkyl group having 1 to 2 carbon atoms, $R_2$, $R^1_2$, or $R_3$ and $R^1_3$ independently represent a hydrogen atom or a methyl group, w and z independently represent an integer of 2 or 3, x represents an integer from 0 to n, n represents an integer from 3 to 6, the sum of x and y equals n, and wherein the spacer side chain comprises a linear hydrocarbon-containing backbone of 3 to 8 atoms.

In certain embodiments, said backbone comprises sulfur, oxygen or nitrogen.

In certain embodiments, w=2, z=2 x=o and y=3.
In certain embodiments, w=2, z=2, x=o and y=3.
In certain embodiments, w=2, z=2, x=o and y=4.
Compounds include, but are not limited to:

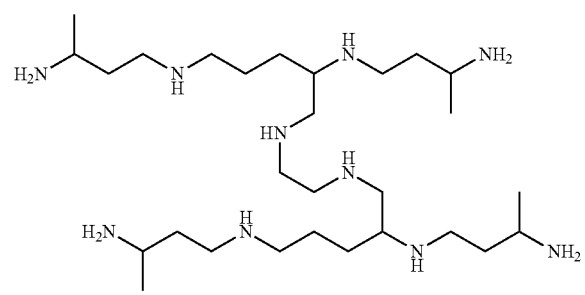

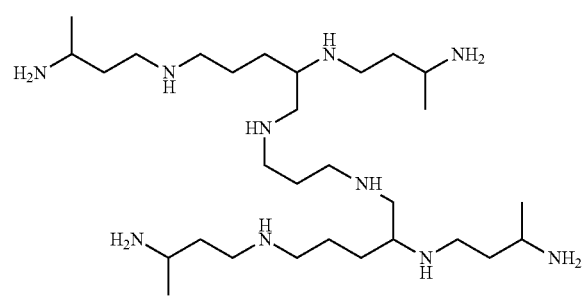

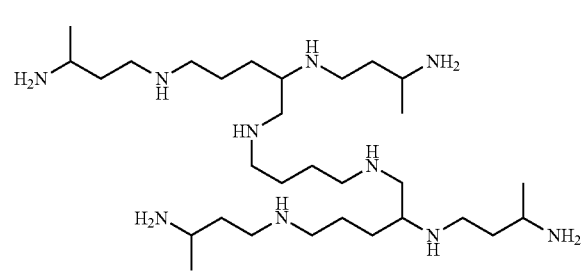

-continued

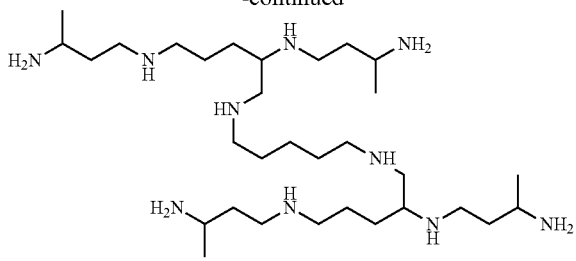

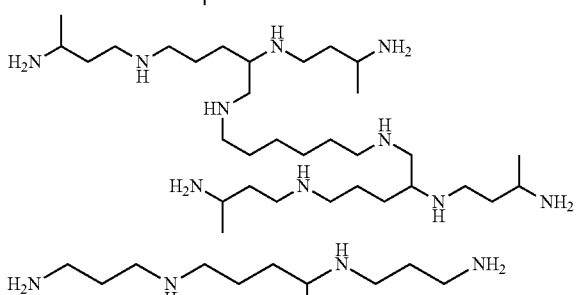

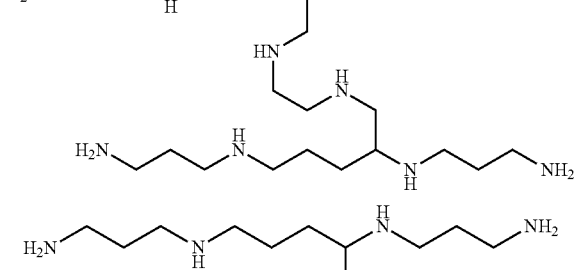

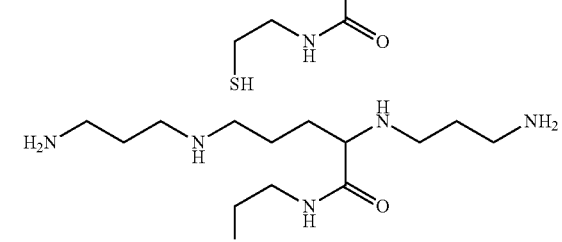

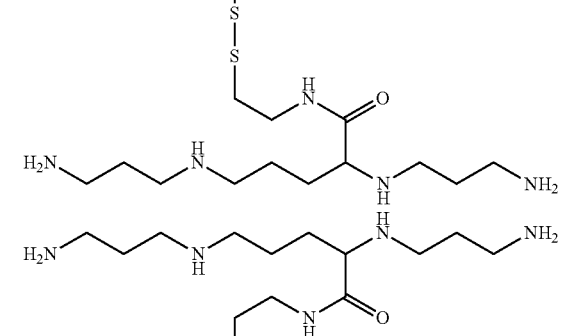

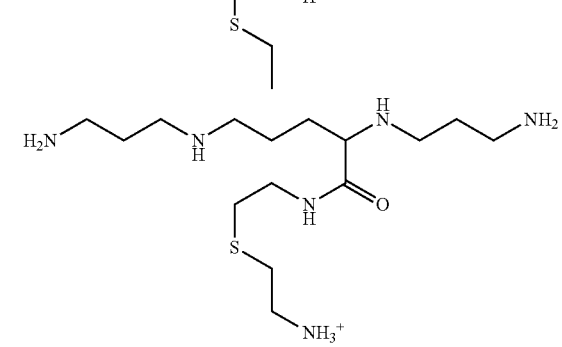

57
-continued
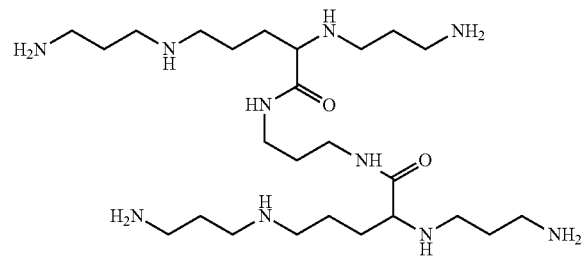
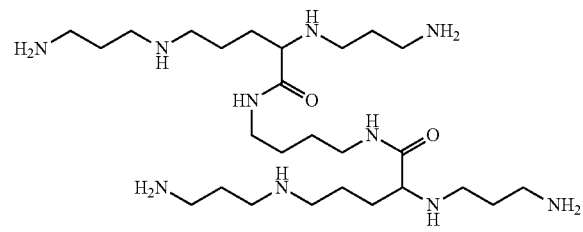
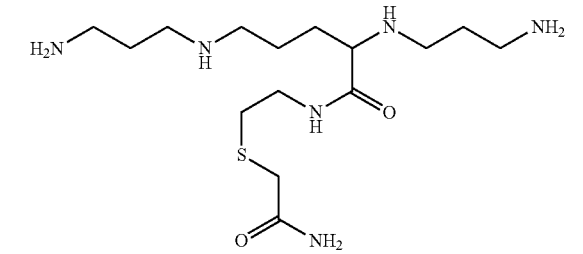
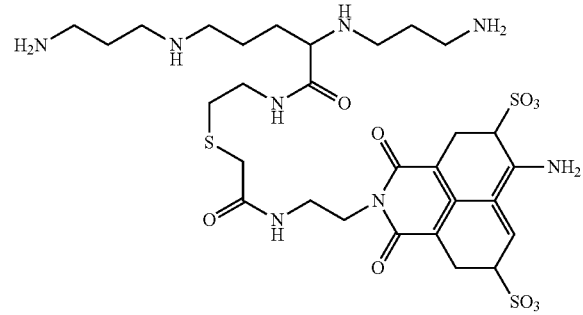
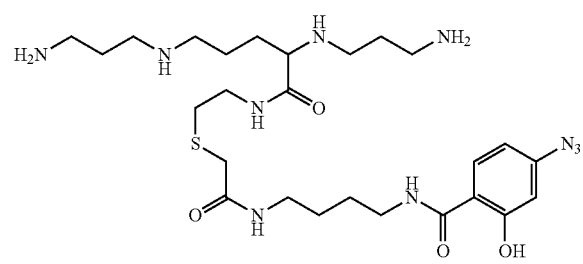
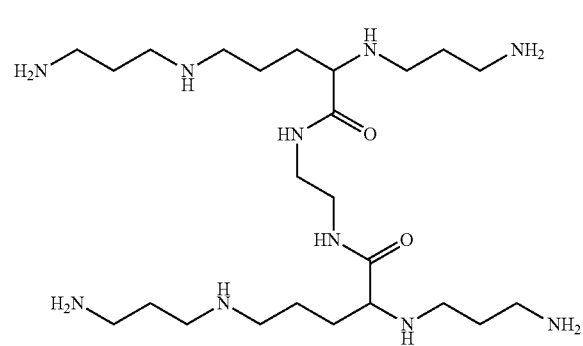
58
-continued
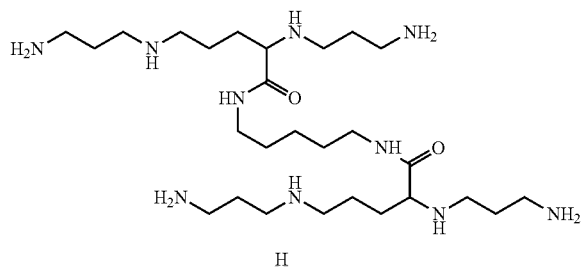
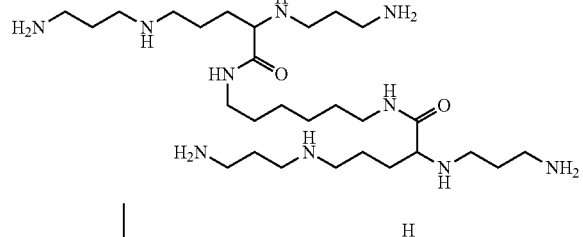
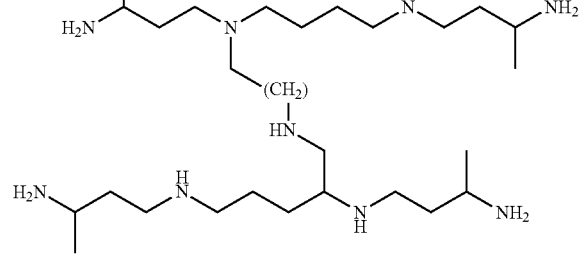
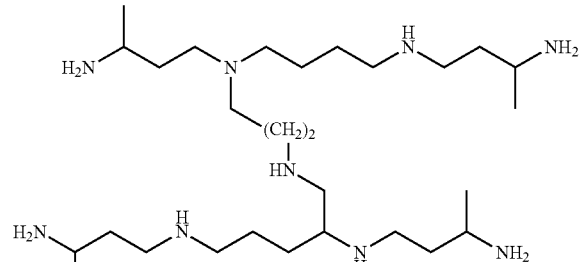
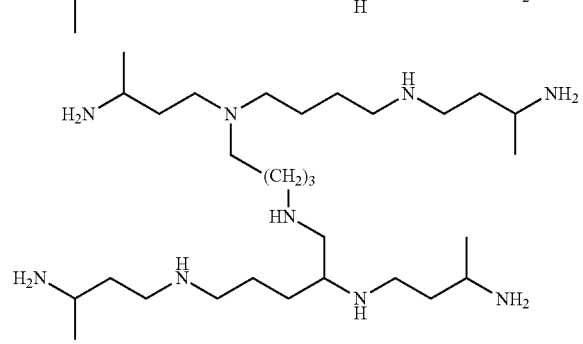
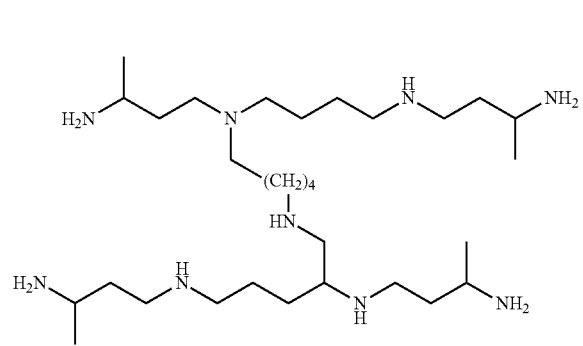

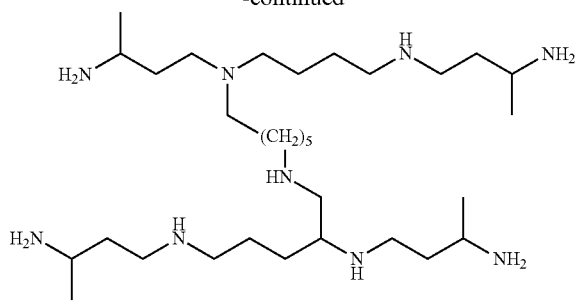

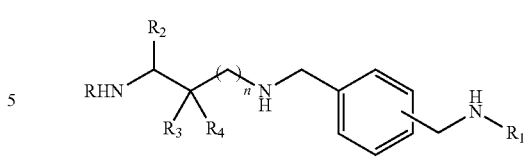

wherein n can be 0 to 8, R and $R_1$ are described as above, $R_2$ can be independently selected from hydrogen, —$CH_3$, —$CH_2CH_3$, and $R_3$ and $R_4$ may be the same or different and are independently selected from hydrogen, or fluorine.

In certain embodiments, compounds that can be used according to this disclosure are described in formula 12c:

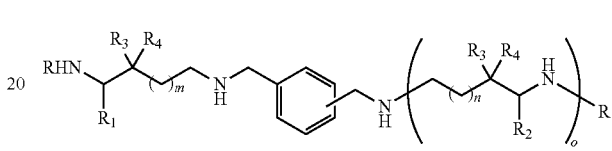

wherein, m and n can be 0 to 7 independently, but m cannot equal n when $R_1$ equals $R_2$ and $R_3$ equals $R_4$, o can be 2 to 4, R can be independently selected from H, —$CH_3$, —$CH_2CH_3$, $R_1$ and $R_2$ can be independently selected from hydrogen, —$CH_3$, —$CH_2CH_3$, and $R_3$ and $R_4$ may be the same or different and are independently selected from hydrogen or fluorine.

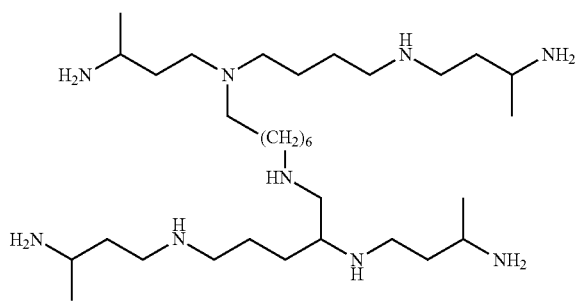

Additional disclosure may be found in WO98/17632, the disclosure of which is incorporated by reference as if written herein in its entirety.

Additional analogs and derivatives include those encompassed by the following formula 12a:

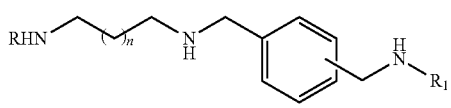

wherein, n can be 0 to 8 and the aminomethyl functionality can be ortho, meta or para substituted, R is hydrogen, —$CH_3$, —$CH_2CH_3$, 2-aminoethyl, 3-aminopropyl, 4-aminobutyl, 5-aminopentyl, 6-aminohexyl, 7-aminoheptyl, 8-aminooctyl, N-methyl-2-aminoethyl, N-methyl-3-aminopropyl, N-methyl-4-aminobutyl, N-methyl-5-aminopentanyl, N-methyl-6-aminohexyl, N-methyl-7-aminoheptyl, N-methyl-8-aminooctyl, N-ethyl-2-aminoethyl, N-ethyl-3-minopropyl, N-ethyl-4-aminobutyl, N-ethyl-5-aminopentyl, N-ethyl-6-aminohexyl, N-ethyl-7-aminoheptyl or N-ethyl-8-aminooctyl and $R_1$ is a moiety selected from the group consisting of a hydrogen or a straight or branched C1-20 saturated or unsaturated aliphatic; aliphatic amine but not propylamine when R=H, n=1 and the aminomethyl functionality is para substituted; an alicyclic; single or multi-ring aromatic; single or multi-ring aryl substituted aliphatic; aliphatic-substituted single or multi-ring aromatic; a single or multi-ring heterocyclic, a single or multi-ring heterocyclic-substituted aliphatic; an aliphatic-substituted aromatic; and halogenated forms thereof.

In certain embodiments, the analogs and derivatives that can be used according to this disclosure can be further modified as described in formula 12b:

In certain embodiments, compounds have formula 12d:

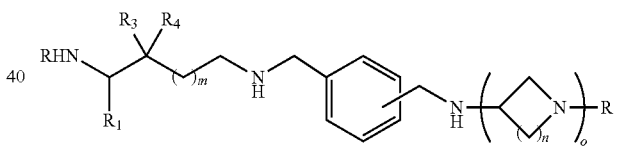

wherein, R is hydrogen, —$CH_3$, —$CH_2CH_3$, m and n can be 0 to 7 independently and o can be 2 to 4, $R_2$ can be independently selected from hydrogen, —$CH_3$, —$CH_2CH_3$, and $R_3$ and $R_4$ may be the same or different and are independently selected from hydrogen or fluorine.

In certain embodiments, compounds of the present invention are represented by formula 12e:

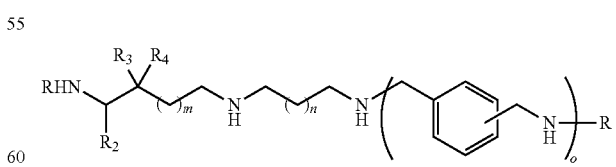

wherein, R is hydrogen, —$CH_3$, —$CH_2CH_3$, m can be 0 to 7, n can be 0 to 8 and o can be 2 to 4, $R_2$ can be independently selected from hydrogen, —$CH_3$, —$CH_2CH_3$, and $R_3$ and $R_4$ may be the same or different and are independently selected from hydrogen or fluorine.

Compounds include, but are not limited to:
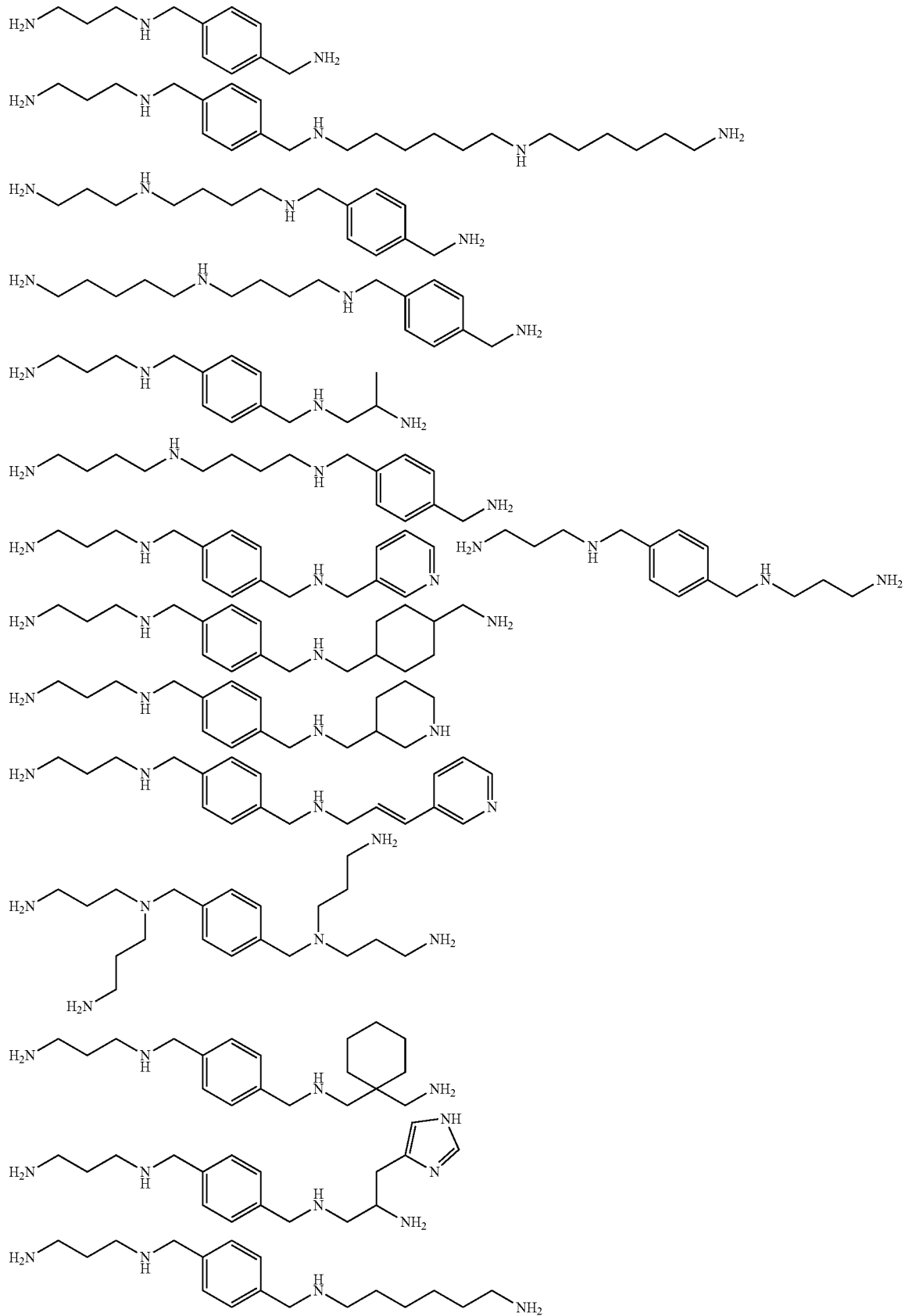

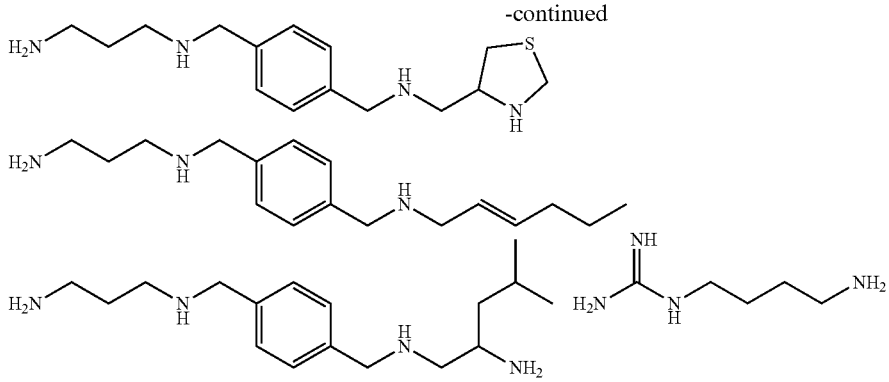

Additional disclosure may be found in WO05/105729, the disclosure of which is incorporated by reference as if written herein in its entirety.

Additional analogs and derivatives include compounds of the formulas 13a-d:

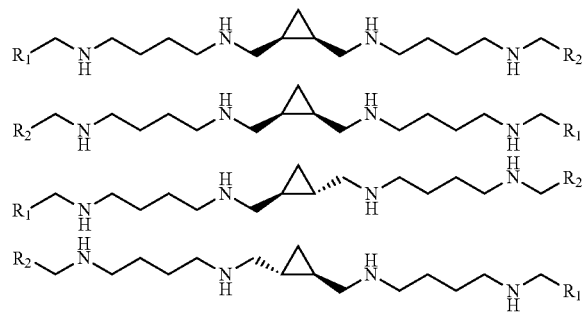

wherein $R_1$ and $R_2$ are independently selected from the group consisting of —$C_1$-$C_{10}$ alkyl, —$C_3$-$C_{10}$ cycloalkyl, —$C_1$-$C_{10}$ alkylene-cycloalkyl, —$C_6$-$C_{10}$ aryl, and —$C_1$-$C_{10}$ alkylene-aryl, wherein when both $R_1$ and $R_2$ are alkyl, at least one of $R_1$ and $R_2$ is —$C_2$-$C_{10}$ alkyl and wherein both $R_1$ and $R_2$ are not tert-butyl; and all salts, hydrates, solvates, and stereoisomers thereof; and all mixtures of stereo isomers thereof, including racemic mixtures. In one embodiment, the substituents on the cyclopropyl ring are trans to each other. In another embodiment, the substituents on the cyclopropyl ring are cis to each other.

In one embodiment, when both $R_1$ and $R_2$ are alkyl, at least one of $R_1$ and $R_2$ is straight-chain alkyl. In another embodiment, when both $R_1$ and $R_2$ are alkyl, both $R_1$ and $R_2$ are straight-chain alkyl. In one embodiment, one of $R_1$ and $R_2$ is —$C_1$-$C_{10}$ alkyl and the other is —$C_2$-$C_{10}$ alkyl. In one embodiment, one of $R_1$ and $R_2$ is —$C_1$-$C_{10}$, alkyl and the other is —$C_4$-$C_{10}$ alkyl. In one embodiment, both $R_1$ and $R_2$ are —$C_4$-$C_{10}$ alkyl. In one embodiment, one of $R_1$ and $R_2$ is —$C_6$-$C_{10}$ alkyl. In one embodiment, both $R_1$ and $R_2$ are —$C_6$-$C_{10}$ alkyl. In one embodiment, one of $R_1$ and $R_2$ is —$C_1$-$C_{10}$ alkyl and the other is selected from the group consisting of —$C_2$-$C_4$ straight-chain alkyl and —$C_4$-$C_{10}$ alkyl. In another embodiment, $R_1$ and $R_2$ are independently selected from the group consisting of —$CH_3$, —$(CH_2)_3CH_3$, and —$(CH_2)sCH_3$, provided that both $R_1$ and $R_2$ are not —$CH_3$.

In one embodiment, one of $R_1$ and $R_2$ is —$C_1$-$C_{10}$ alkyl and the other is —$C_3$-$C_{10}$ cycloalkyl, —$C_1$-$C_{10}$ alkylene-cycloalkyl, —$C_6$-$C_{10}$ aryl, or —$C_1$-$C_{10}$ alkylene-aryl. In one embodiment, one of $R_1$ and $R_2$ is —$C_1$-$C_{10}$ alkyl and the other is —$C_3$-$C_{10}$ cycloalkyl or —$C_1$-$C_{10}$ alkylene-cycloalkyl. In one embodiment, one of $R_1$ and $R_2$ is —$C_1$-$C_{10}$ alkyl and the other is —$C_3$-$C_{10}$ cycloalkyl. In one embodiment, one of $R_1$ and $R_2$ is —$C_1$-$C_{10}$ alkyl and the other is —$C_6$-$C_{10}$ aryl or —$C_1$-$C_{10}$ alkylene-aryl. In one embodiment, one of $R_1$ and $R_2$ is —$C_1$-$C_{10}$ alkyl and the other is —$C_6$-$C_{10}$ aryl. In another embodiment, both $R_1$ and $R_2$ are —$C_6$-$C_{10}$ aryl. In another embodiment, both $R_1$ and $R_2$ are —$C_3$-$C_{10}$ cycloalkyl. In one embodiment, the aryl group is benzene. In one embodiment, the cycloalkyl group is adamantyl. In one embodiment, the adamantyl group is 1-adamantyl. In another embodiment, the adamantyl group is 2-adamantyl. In another embodiment, $R_1$ and $R_2$ are independently selected from the group consisting of —$CH_3$, phenyl, and adamantyl, provided that both $R_1$ and $R_2$ are not —$CH_3$.

Compounds include, but are not limited to:

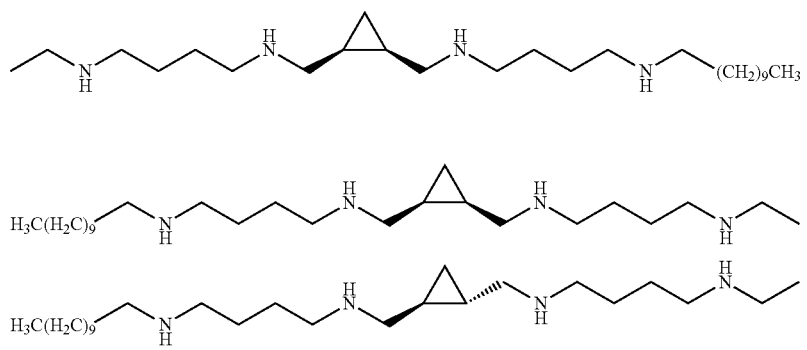

-continued
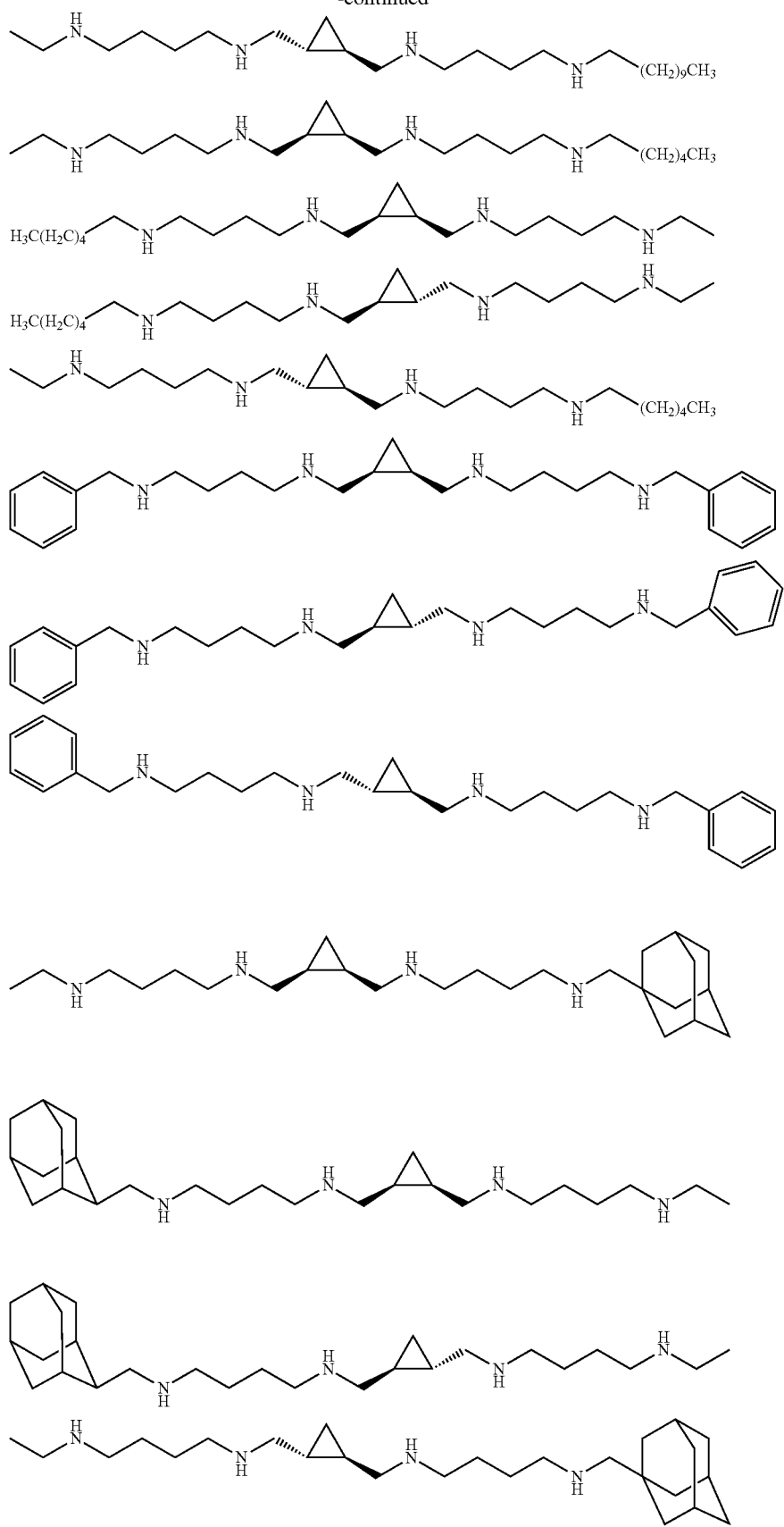

Additional disclosure may be found in WO2008/112251, the disclosure of which is incorporated by reference as if written herein in its entirety.

Additional analogs and derivatives include compounds of the formula 14a:

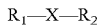

wherein $R_1$ is H, or is a head group selected from the group consisting of a straight or branched $C_{1-10}$ aliphatic, alicyclic, single or multi-ring aromatic, single or multiring aryl substituted aliphatic, aliphatic-substituted single or multiring aromatic, a single or multiring heterocyclic, a single or multiring heterocyclic-substituted aliphatic and an aliphatic-substituted aromatic;

$R_2$ is a polyamine; and

X is CO, NHCO, NHCS, or $SO_2$

In another embodiment of the above composition, $R_2$ has the formula

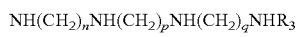

wherein n, p and q vary independently and n=p=q=1 to 12; and $R_3$ is H; $C_{1-10}$ alkyl; $C_{1-10}$ alkenyl; $C_{1-10}$ alkynyl; alicyclic; aryl; aryl-substituted alkyl, alkenyl or alkynyl; alkyl-, alkenyl-, or alkynyl-substituted aryl; guanidino; heterocyclic; heterocyclic-substituted alkyl, alkenyl or alkynyl; and alkyl-, alkenyl-, or alkynyl-substituted heterocyclic.

The above composition may further comprise, linked between X and $R_2$, a linker L and an additional group Y, such that said composition has the formula 14b:

wherein

L is a $C_{1-10}$ alkyl; $C_{1-10}$ alkenyl; $C_{1-10}$ alkynyl, alicyclic, or heterocyclic;

X is CO, $SO_2$, NHCO or NHCS; and

Y is CONH, $SO_2NH$, NHCO, NHCONH, NHCSNH, $NHSO_2$, $SO_2$, O, or S.

In the foregoing compositions $R_1$ can have the formula:

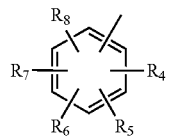

wherein $R_4$, $R_5$, $R_6$, $R_7$, and $R_8$ are, independently, H, OH, halogen, $NO_2$, $NH_2$, $NH(CH)_nCH_3$, $N((CH)_nCH_3)_2$, CN, $(CH)_nCH_3$, $O(CH)_nCH_3$, $S(CH2)_nCH_3$, $NCO(CH_2)_nCH_3$, $O(CF_2)_nCF_3$, or CO—$O(CH)_nCH_3$ where n=0 to 10.

Alternatively, $R_1$ has the formula:

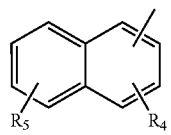

wherein $R_4$ and $R_5$ are, independently, H, OH, halogen, $NO_2$, $NH_2$, $NH(CH)_nCH_3$, $N((CH)_nCH_3)_2$, CN, $(CH)_nCH_3$, $O(CH)_n$ $CH_3$, $S(CH2)_nCH_3$, $NCO(CH_2)_nCH_3$, $O(CF_2)_nCF_3$, or CO—$O(CH)_nCH_3$ where n=0 to 10.

In yet another embodiment, $R_1$ has the formula:

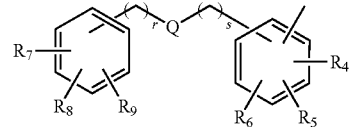

wherein r and s vary independently and r=s=0 to 6;

$R_4$, $R_5$, $R_6$, $R_7$, $R_8$, and $R_9$ are, independently, H, OH, halogen, $NO_2$, $NH_2$, $NH(CH)_nCH_3$, $N((CH)_nCH_3)_2$, CN, $(CH)_nCH_3$, $O(CH)_nCH_3$, $S(CH2)_nCH_3$, $NCO(CH_2)_nCH_3$, $O(CF_2)_nCF_3$, or CO—$O(CH)_nCH_3$ where n=0 to 10;

Q is CONH, $SO_2NH$, NHCO, NHCONH, NHCSNH, $NHSO_2$, $SO_2$, O, or S.

Furthermore, $R_1$ may have the formula:

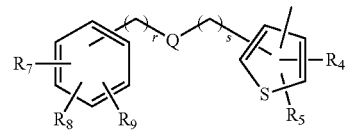

wherein r and s vary independently and are 0 to 6;

$R_4$, $R_5$, $R_6$, and $R_7$ are, independently, H, OH, $NO_2$, $NH_2$, $NH(CH)_nCH_3$, $N((CH)_nCH_3)_2$, CN, $(CH)_nCH_3$, $O(CH)_nCH_3$, $S(CH2)_nCH_3$, $NCO(CH_2)_nCH_3$, $O(CF_2)_nCF_3$, or CO—$O(CH)_nCH_3$ where n=0 to 10; and Q is CONH, $SO_2NH$, NHCO, NHCONH, NHCSNH, $NHSO_2$, $SO_2$, O, or S.

In the foregoing compositions, $R_1$ may be selected from the group consisting of naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, piperidine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H-1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chloropheny)-6-methyl-7-chloroquinoline, 6-chloroimidazo[2,1-β]thiazole, α-methylcinnamic acid, and 2-[1,2-dihydro-2H-1,4-benzodioxepinyl]thiazole.

R1 may also be a D- or L-amino acid.

Also provided is the above composition where R1 has a formula selected from the group consisting of

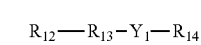  (A)

(B)

(C)

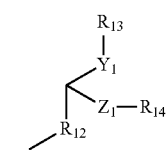

-continued

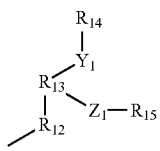
(D)

wherein $R_{12}$ and $R_{13}$, independently, are H, naphthalene, phenanthrene, anthracene, pyrene, dibenzofuran, acridine, 2,1,3-benzothiodiazole, quinoline, isoquinoline, benzofuran, indole, carbazole, fluorene, 1,3-benzodiazine, phenazine, phenoxazine, phenothiazine, adamantane, camphor, pipiridine, alkylpiperazine, morpholine, cyclopropyl, cyclobutyl, cyclopentyl, cyclohexyl, cycloheptyl, cyclooctyl, thiophene, furan, pyrrole, alkyl-1,2-diazole, alkylimidazole, alkyl-1H-1,2,3-triazol, alkyl-1H-1,2,3,4-tetrazole, thiazole, oxazole, 1,3,4-thiadiazole, pyridinyl, pyrimidine, 1,2-diazine, 1,4-diazine and 1,3,5-triazine, 4-dimethylaminoazobenzene, 3-phenyl-5-methylisooxazole, 3-(2-chlorophenyl)-5-methylisooxazole, 2-(4-chloropheny)-6-methyl-7-chloroquinoline, 6-chloroimidazo[2,1-β]thiazole, α-methylcinnamic acid, or 2-[1,2-dihydro-2H-1,4-benzodioxepinyl]thiazole;

and further, wherein a ring of $R_{12}$, $R_{13}$ or both in formulas (A), (B) and (D), is optionally substituted with one or more of OH, halogen, $NO_2$, $NH_2$, $NH(CH)_nCH_3$, $N((CH)_nCH_3)_2$, CN, $(CH)_nCH_3$, $O(CH)_nCH_3$, $S(CH2)_nCH_3$, $NCO(CH_2)_nCH_3$, $O(CF_2)_nCF_3$, or $CO—O(CH)_nCH_3$ where n=0 to 10

$R_{14}$ and $R_{15}$ and, in formula (C), $R_{13}$, independently, are $(CH_2)_n$, $(CH_2)_nCH=CH$, $(CH_2)_n(CH=CH)_mCO$, or $(CH_2)_nCO$ where n=0 to 5 and m=1 to 3;

$Y_1$, and $Z_1$, independently, are CONH, $SO_2NH$, NHCO, NHCONH, NHCSNH, $NHSO_2$, $SO_2$—$NHSO_2$, $SO_2$, O, S, or COO;

or when $R_1$ is of formula (A) or (B), Y1 represents a bond between a C or N atom of $R_{12}$, and a C or N atom of $R_{13}$, and $Z_1$ represents a bond between a C or N atom of $R_{13}$, and a C or N atom of $R_{14}$; or when $R_1$ is of formula (C) or $Y_1$ represents a bond between the C and a C or N atom of $R_{13}$ and $Z_1$ represents a bond between the C and a C or N atom of $R_{14}$; or when $R_1$ is of formula (D) $Y_1$ represents a bond between a C or N atom of $R_{12}$ and a C or N atom of $R_{14}$ and $Z_1$ represents a bond between a C or N atom of $R_{13}$ and a C or N atom of $R_{15}$.

In the above compositions, $R_2$ preferably has the formula $NHCH(Z_1)(CH_2)_nNH(CH_2)_pNH(CH_2)_qCH(Z1)NHR_3$ wherein n, p and q vary independently and n=p=q=1 to 12; and $R_3$ is H; $C_{1-10}$ alkyl; $C_{1-10}$ alkenyl; $C_{1-10}$ alkynyl; alicyclic; aryl; aryl-substituted alkyl, alkenyl or alkynyl; alkyl-, alkenyl-, or alkynyl-substituted aryl; guanidine or heterocyclic; and Z, is $CH_3$, $CH_2CH_3$ or cyclopropyl.

In another embodiment, $R_2$ has the formula:

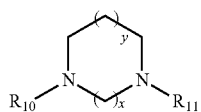

wherein x=1 to 4; y=1 to 3, $R_{10}$ and $R_{11}$ are, independently, H, $(CH_2)nNHR_{12}$ or $(CH_2)_kNH(CH_2)1 NHR_{12}$, where n=k=l=1 to 10, and $R_{12}$ is H or $C(N=H)NH_2$.

In the above compositions, $R_2$ is preferably selected from the group consisting of N1-acetylspermine, N1-acetylspermidine, N8-acetylspermidine, N'-guanidinospermine, cadaverine, aminopropylcadaverine, homo spermidine, caldine (horspermidine), 7-hydroxyspermidine, thermine (norspermine), thermospermine, canavalmine, aminopropylhomospermidine, N,N'-bis(3-aminopropyl)cadaverine, aminopentylnorspermidine, N4-aminopropylnorspermidine, N4-aminopropylspermidine, caldopentamine, homocaldopentamine, N4-bis(aminopropyl)norspermidine, thermopentamine, N4-bis(aminopropyl)spermidine, caldohexamine, homothermohexamine, homocaldohexamine, N-(3-aminopropyl)-1,3-propanediamine, N,N'-bis(3-aminopropyl)ethylendiamine, N,N'-bis(3-aminopropyl)-1,4-piperazine, N,N'-bis(3-aminopropyl)-1,3-piperazine, N,N'-bis(3-aminopropyl)-1,3-propanediamine, N,N'-bis(2-aminoethyl)-1,3-propanediamine, tris(3-aminopropyl)amine, and tris(aminoethyl)amine Compounds include, but are not limited to:

-continued
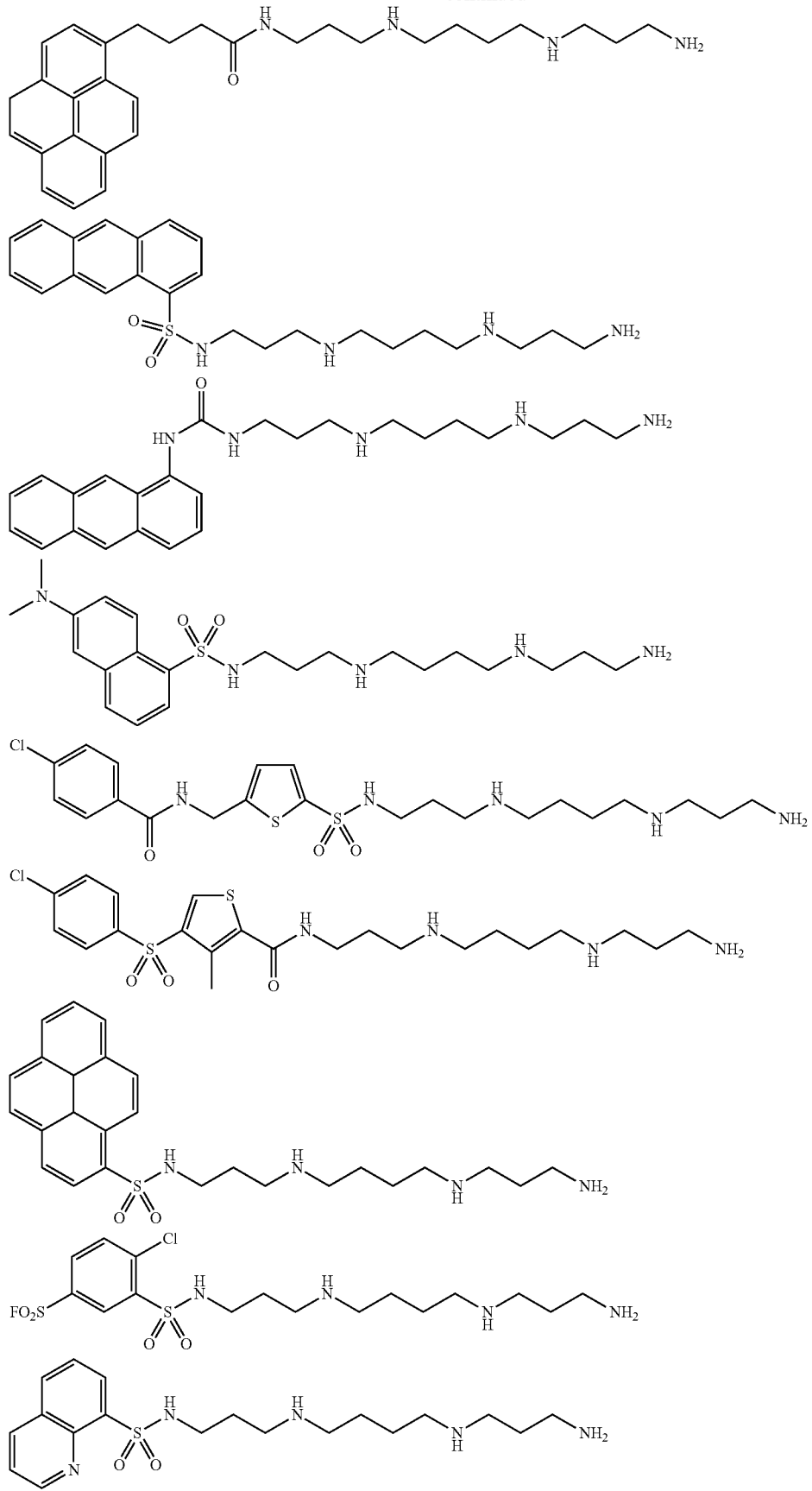

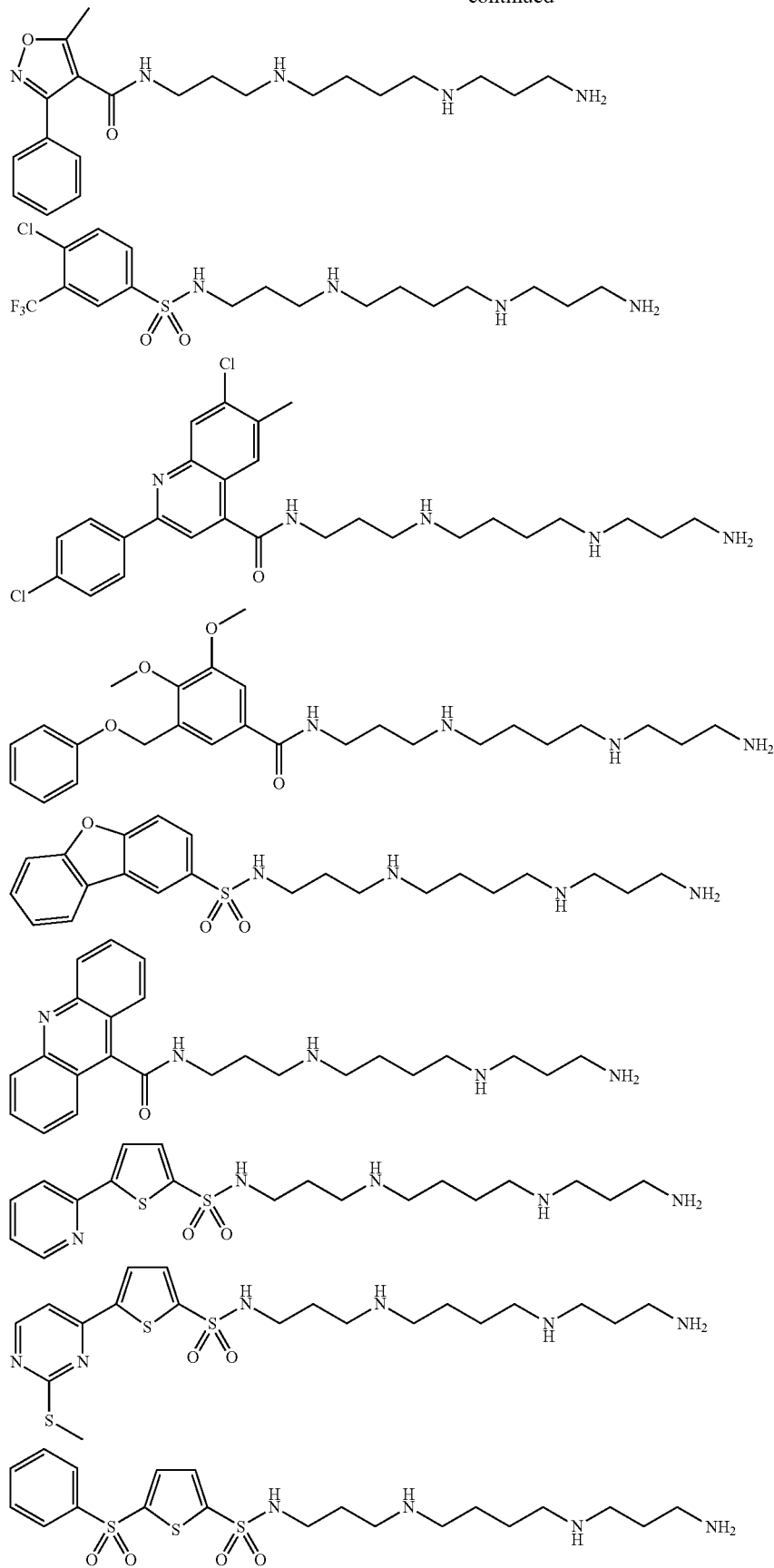

-continued
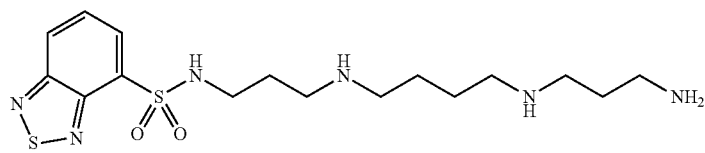
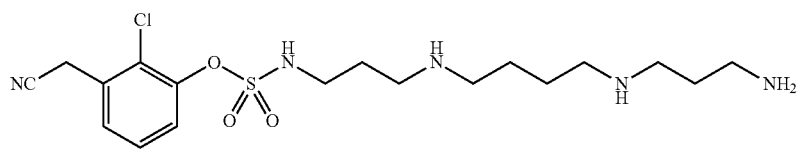
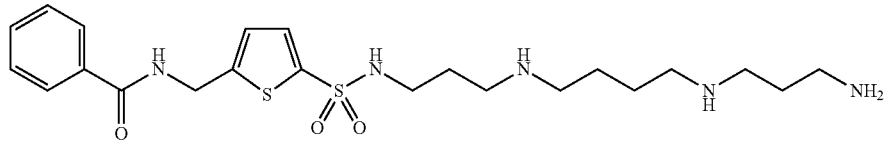
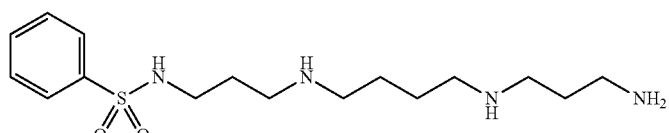
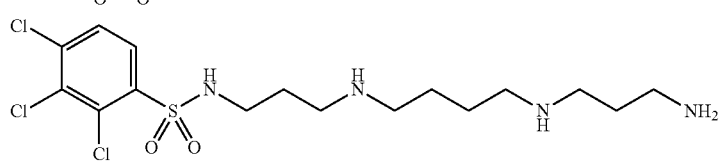
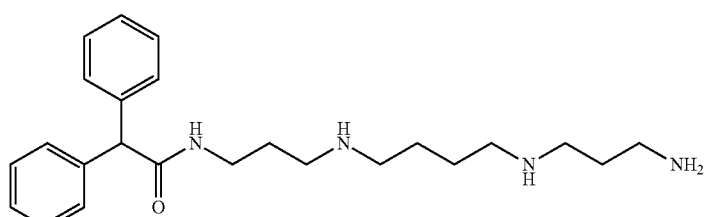
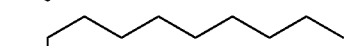
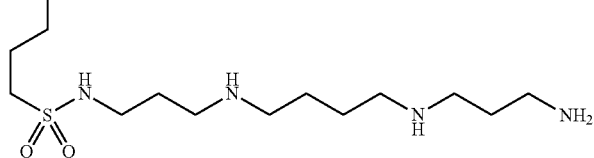
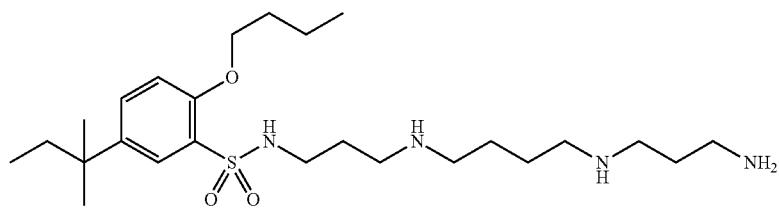
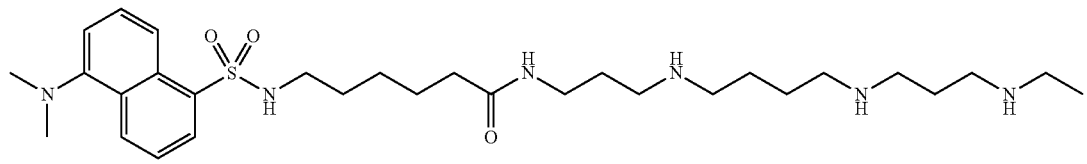
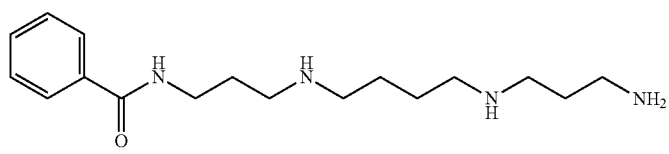

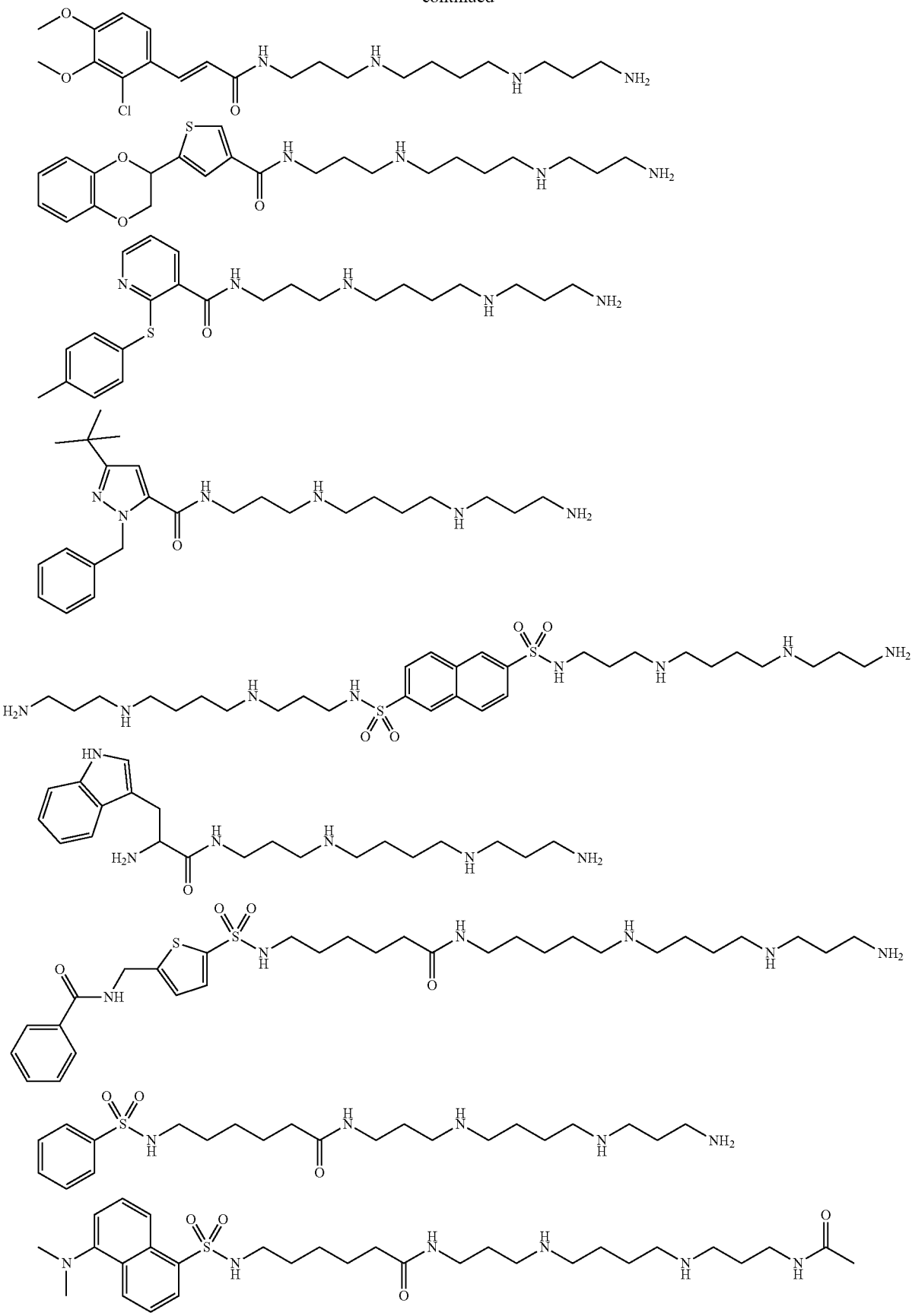

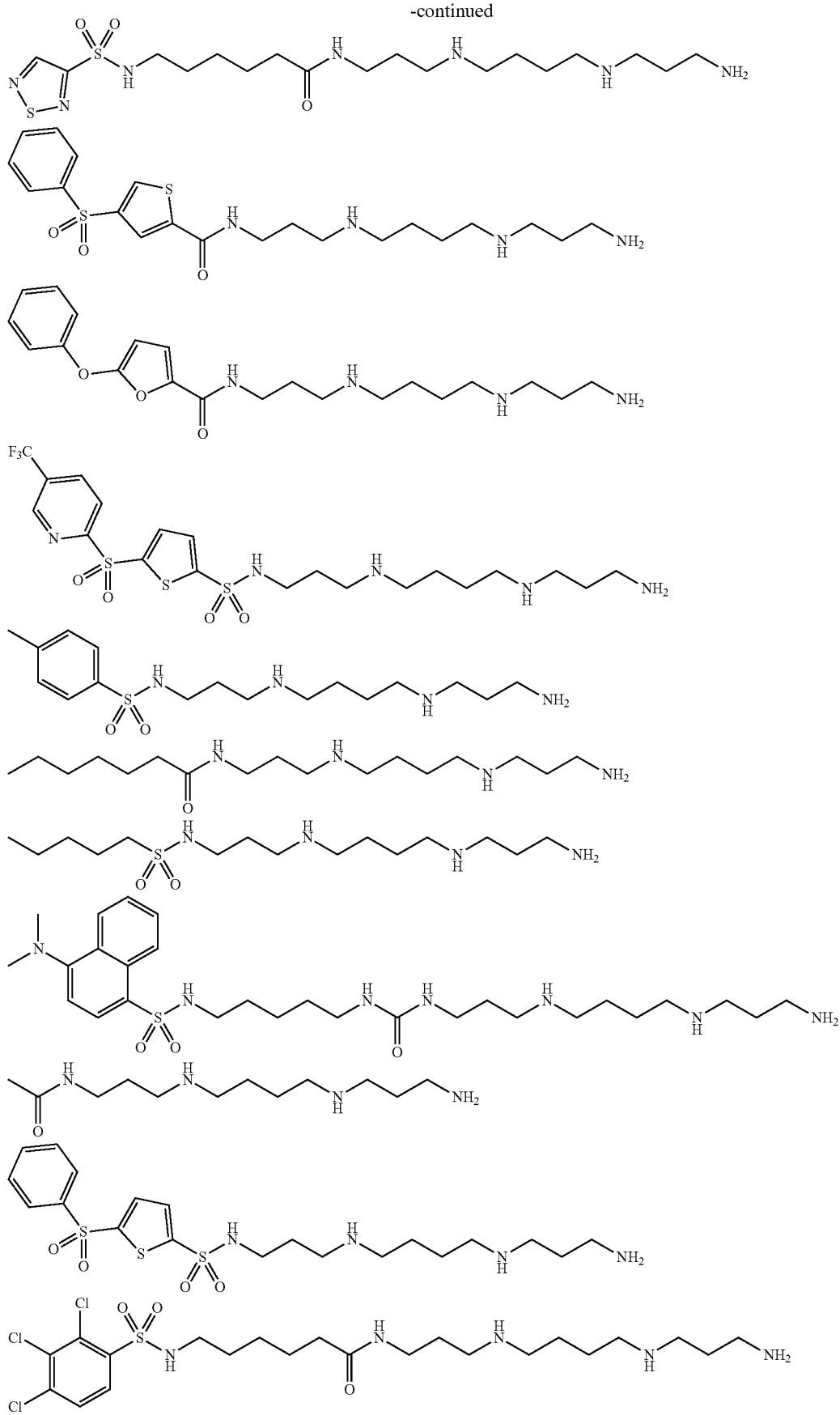

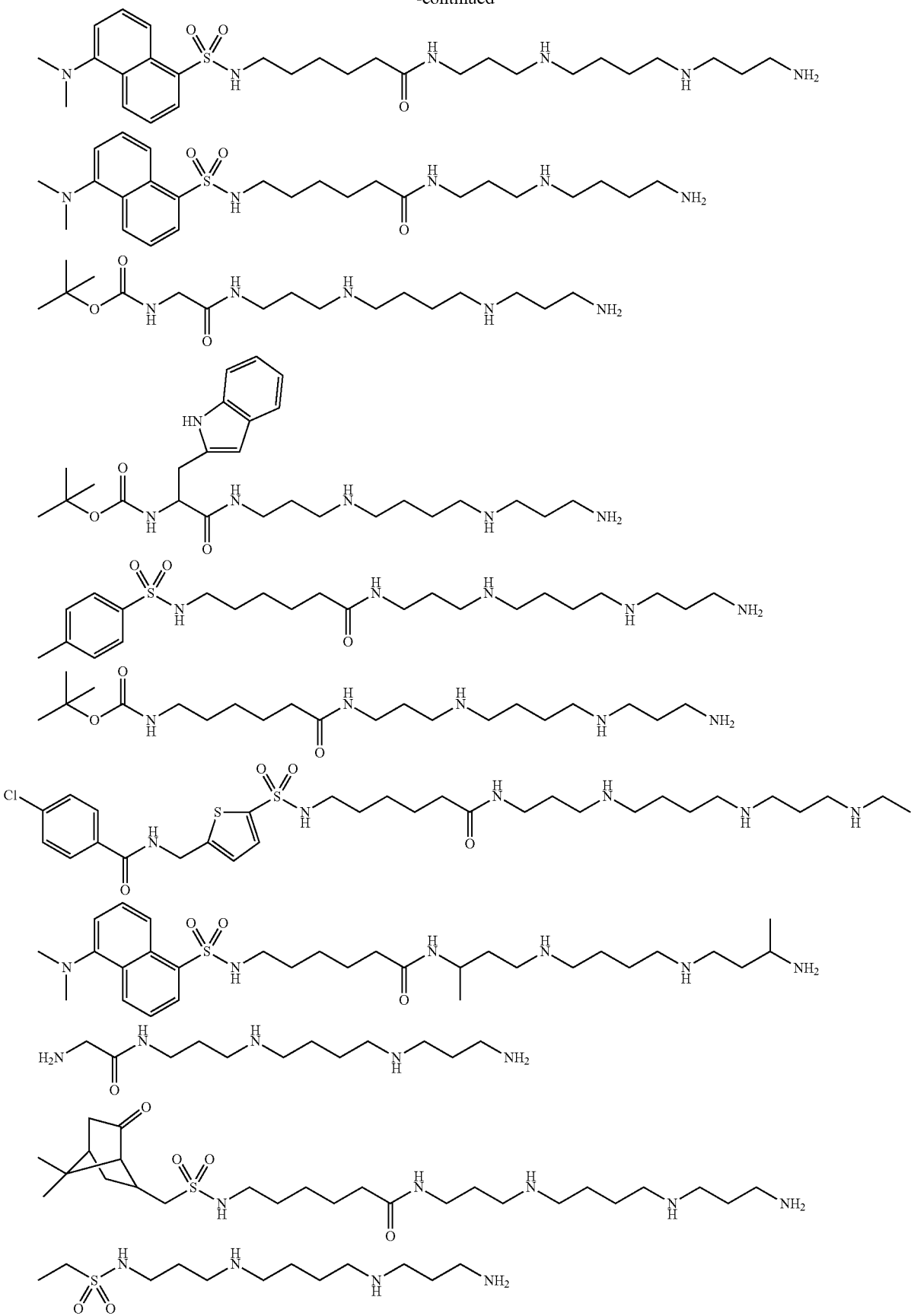

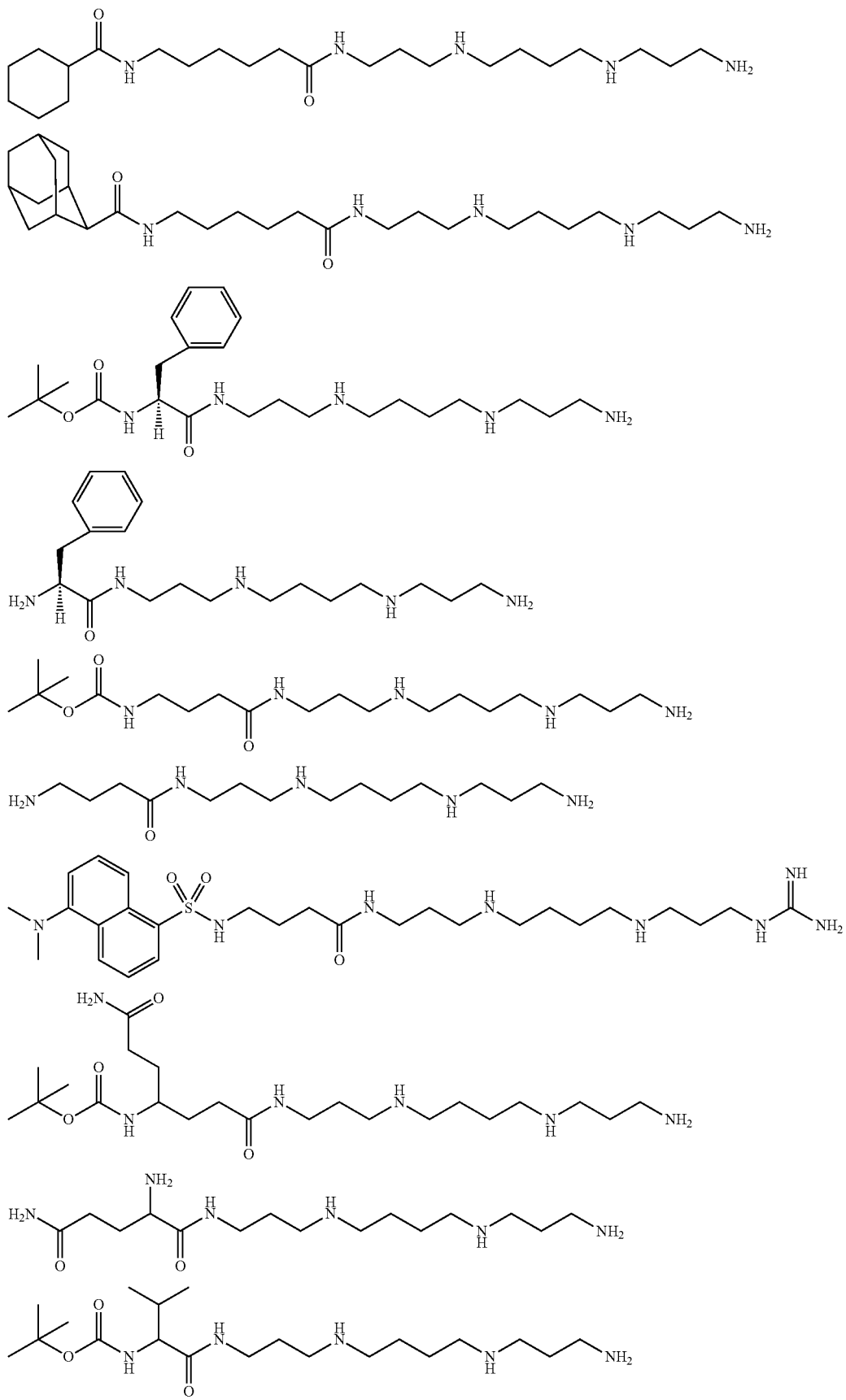

-continued
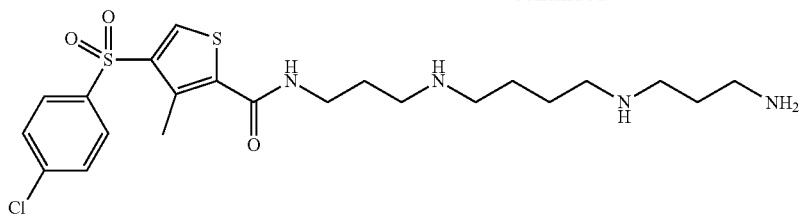
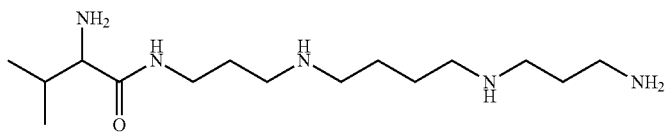
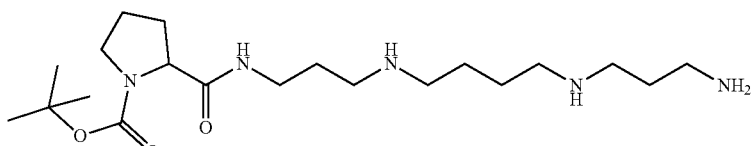
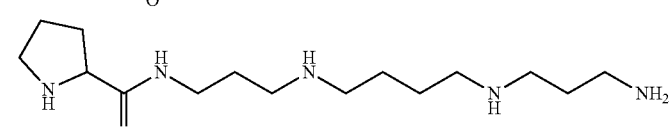
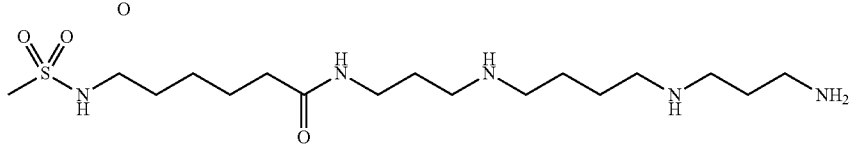
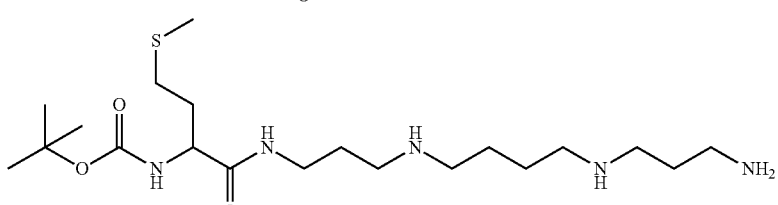
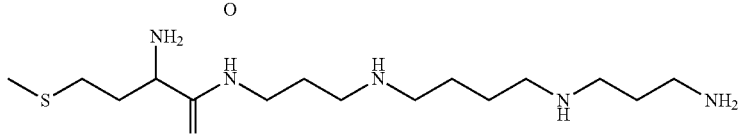
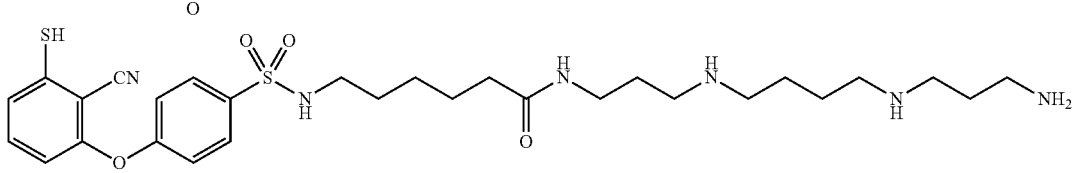
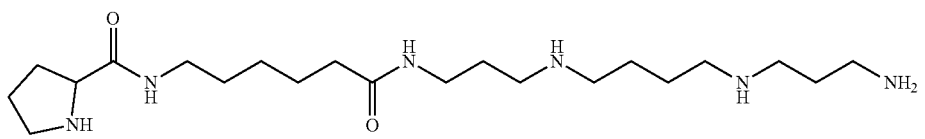
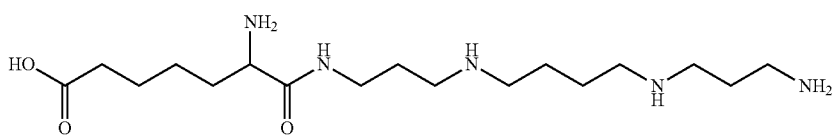

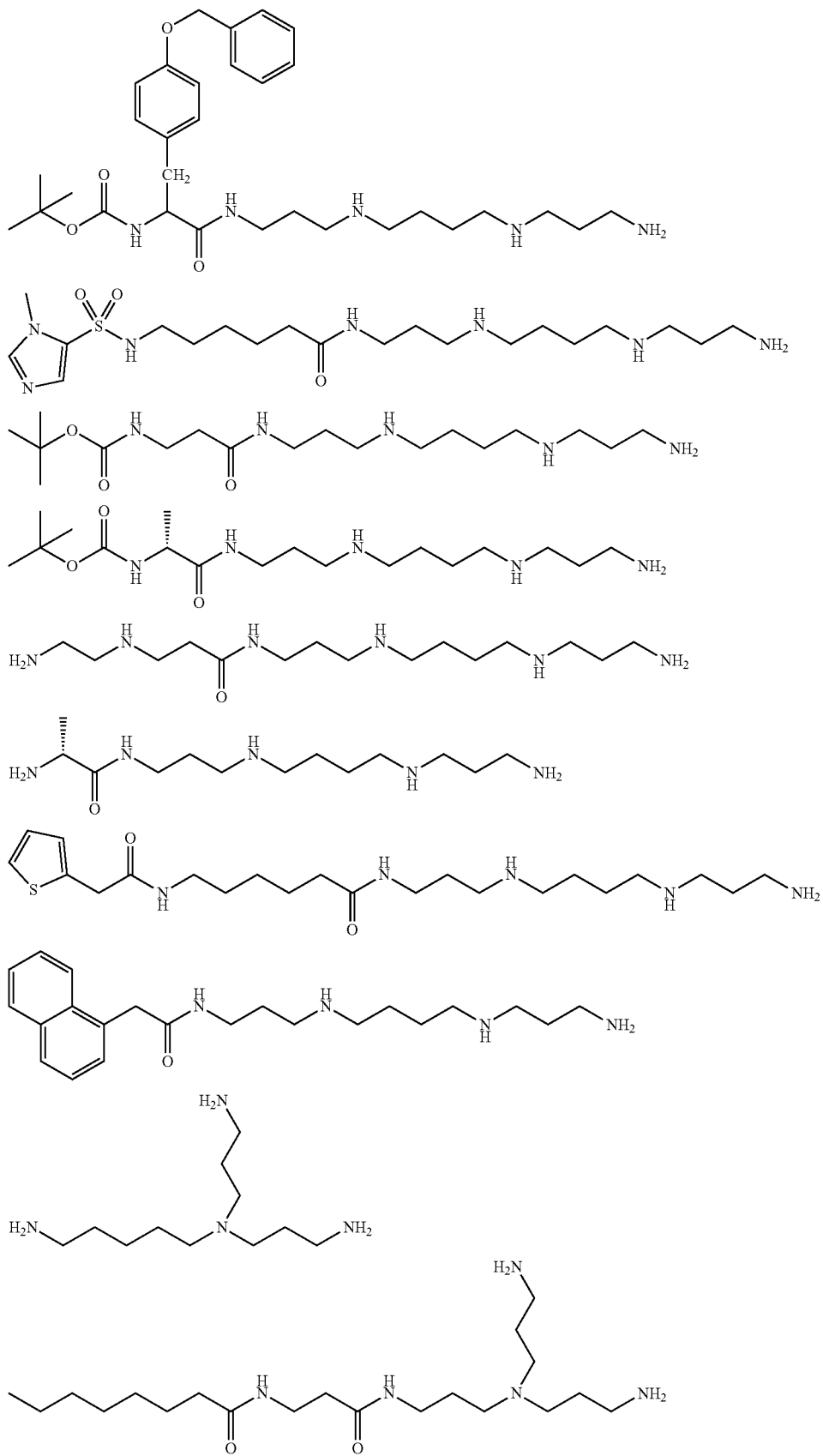

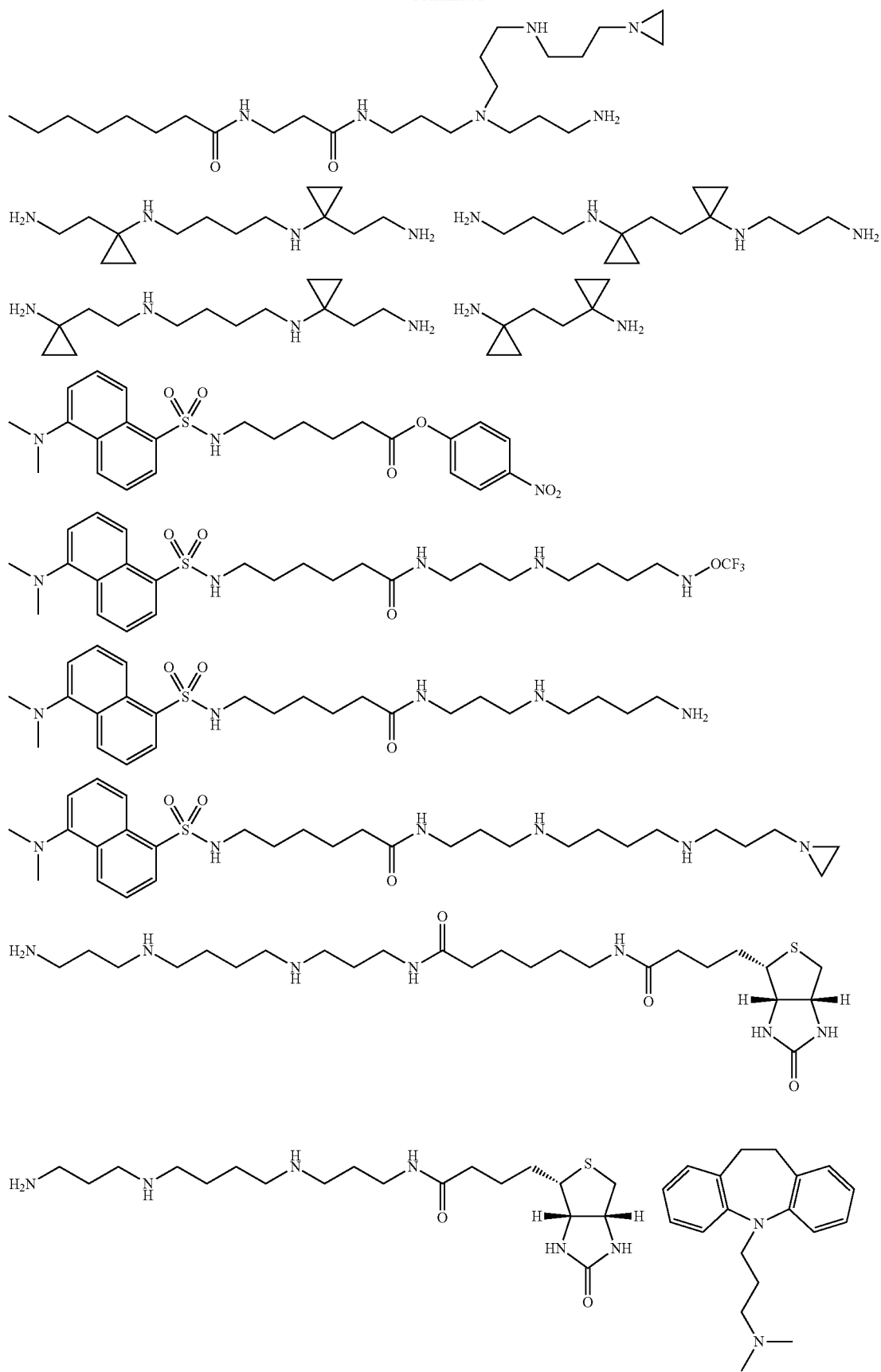

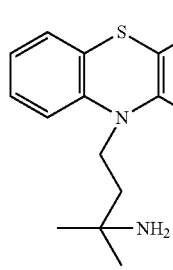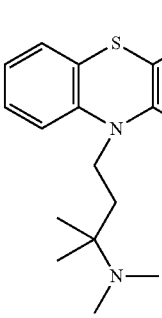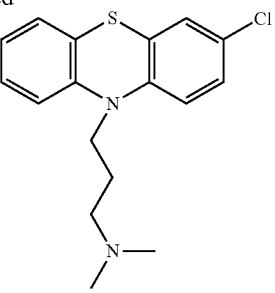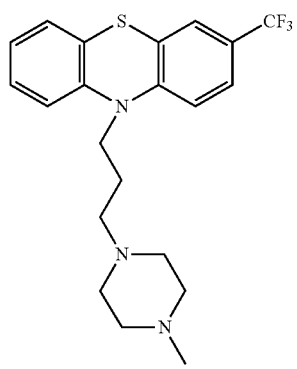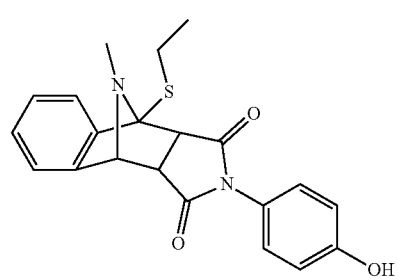

Additional disclosure may be found in WO99/03823, the disclosure of which is incorporated by reference as if written herein in its entirety.

Yet further compounds include, but are not limited to:

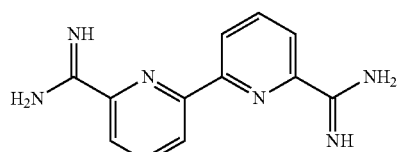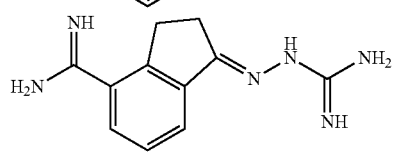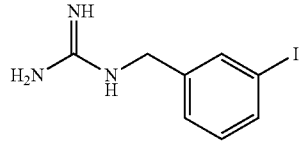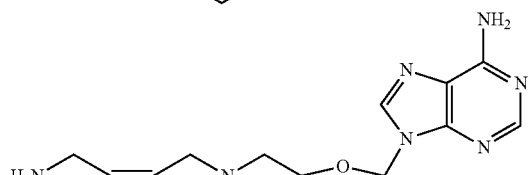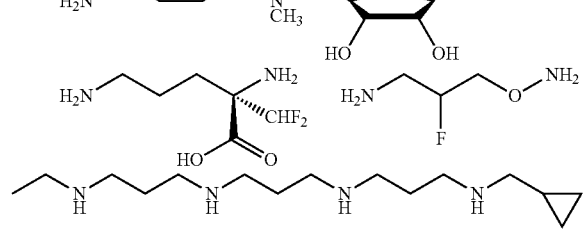

-continued

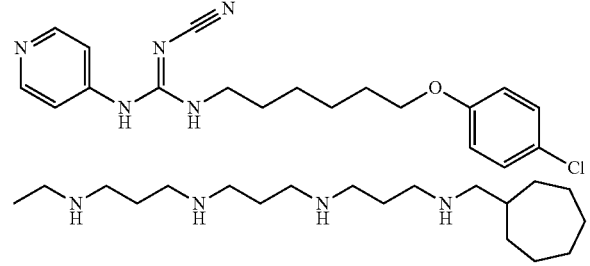

Additional disclosure may be found in: Ackermann, J M; Pegg, A E; McCloskey, D E; *Progress in Cell Cycle Research*, 2003, Vol. 5, 461-468; Ekelund, S; Nygren, P; Larsson, R; *Biochemical Pharmacology*, 2001, 61, 1183-1193; Huang, Y; Pledgie, A; Casero Jr, R A; Davidson, N E; *Anti-Cancer Drugs*, 2005, 16, 229-241; and Marton, J L; *Annu. Rev. Pharmacol Toxicol.* 1995, 35, 55-91; the disclosure of which is incorporated by reference as if written herein in their entireties.

Polyamine analogs depicted above may be prepared both as salts and as free bases. In certain embodiments, the salt is the hydrochloride salt. In certain embodiments, the number of coordinated ion pairs (for example $H^+Cl^-$) will be proportional to the number of amino groups in the polyamine Such coordination typically occurs at said amino groups, forming, for example, $NH_3^+Cl^-$ groups. However, not every amino group may be coordinated. For example, if the amino group is adjacent to an electron-withdrawing group such as carbonyl or sulfonyl, it may not retain sufficient electron density to coordinate an ion. In further embodiments, the number of coordinated ions will be proportional to the number of primary and/or secondary amino groups in the polyamine Additional compounds which may be used in the methods and compositions described herein include: naturally occurring polyamines found in prokaryotes and eukaryotic cells, polyamine analogs, polyamine biosynthesis inhibitors, and polyamine transport inhibitors.

Naturally occurring polyamines found in prokaryotes and eukaryotic cells include, but are not limited to: putrescine, spermidine, spermine, diaminopropane, cadaverine, norspermidine, aminopropylcadaverine, homospermine, norspermine, thermospermine, aminopentylnorspermidine, bis(aminopropyl)cadaverine, aminopropylhomospermine, canavalmine, homospermine, caldopentamine, aminopropylcanavaline, bis(aminopropyl)homospermidine, bis(aminobutyl)norspermidine, aminobutylcanavalmine, aminopropylhomospermine, homopentamine, N5-aminobutylhomospermine, caldohexamine, thermohexamine, homothermohexamine, agmatine and N6-methylagmatine. See, e.g., Morgan D. M. L., 1999, Molecular Biotechnology 11: 229.

Polyamine analogs include, but are not limited to, BE-4444 [1,19-bis(ethylamino)-5,10,15-triazanonadecane]; BE-3-3-3 [N1,N11-diethylnorspermine; DENSPM; 1,11-bis(ethylamino)-4,8-diazaundecane; thermine; Warner-Parke-Davis]; BE-3-3[N1,N7-bis(ethyl) norspermidine]; BE-3-4 [N1,N8-bis(ethyl) spermidine]; BE44 [N1,N9-bis(ethyl) homospermidine]; BE-343 [N1,N12-bis(ethyl) spermine; diethylspermine-N1-N12; DESPM]; BE-373 [N,N'-bis(3-ethylamino)propyl)-1,7-heptane diamine, Merrell-Dow]; BE-4-4-4 [N1,N14-bis(ethyl) homospermine; diethylhomospermine-N1-N1-1]; BE-3-4-4-3 [1,17-bis(ethylamino)-4,9, 14triazaheptadecane]; BE-4-3-3-4 [1,17-bis(ethylamino)-5, 9,13-triazaheptadecane]; and 1,12-Mez-SPM [1,12-dimethylspermine]. (WO02007/040535).

Polyamine synthesis inhibitors include but are not limited to: inhibitors of ornithine decarboxylase such as DFMO, aceylenic putrescine, 1-aminooxy-3-aminopropane, antizyme, 2-butylputrescine, cadaverine, L-canaline, 5'-deoxy-5'-[N-methyl-N-[3(aminooxy)ethyl]amino]adenosine, 5'-deoxy-5'-[N-methyl-N-[3-(hydrazinopropyl)amino]adenosine, diaminopropane, 1,3-diamino-2-propanol, 2-difluoromethyl putrescine, difluorophenylethyl(4-aminopropylamidinohydrazone), 2,3-dimethylputrescine, N-dimethylputrescine, 2-ethylputrescine, (+ or −)-alphafluoromethylornithine, 2-fluoro methylputrescine, 2-hexylputrescine, 2-hydrazinoornithine, ibuprofen, D-methyl acetylenic putrescine, methylglyoxal bis(3aminopropylamininohydrazone), 2-methylornithine, 2-methylputrescine, 2-monofluoromethyl-trans-dehydroornithine, 2-monofluoromethyl dehydroputrescine, monofluoromethylornithine, 2-monofluoromethyl putrescine, neomycin, D-ornithine, 2-pentylputrescine, p-phenylenediamine, phosphopeptide MG 25000, phosphothreonine, phosphotyrosine, 2-propylputrescine, putrescine, allo-S-adenosyl-L-methionine, S-ethylthioadenosine, methylthioadenosine, and 5'-methylthioadenosine as discussed in Zollner H. (1993) Handbook of Enzyme Inhibitors, 2nd Ed. Weinheim: Basel(Switzerland); inhibitors of S-adenosylmethionine decarboxylase, such as SAM486A (4-aminoindanon-1(2' amidino)hydrazone dihydrochloride monohydrate), S-adenosyl-1,8-diamino-3thiooctane, S-(5'-adenosyl)methylthio-2-aminooxyethan, S-adenosyl-3-methylthio-i-propylamine, 5'-{[(Z)-4-amino-2-butenyl]methylamino}-5'-deoxyadenosine, 5'-amino-5' deoxyadenosine, 5'-[(aminoiminomethyl) amino]-5']deoxyadenosine dihydrogensulphate, 1-aminooxy-3-aminopropane, [2-(aminooxy)ethyl](5'-deoxyadenosine-5'yl)(methyl)sulphonium, 5'-[(3-aminopropyl]-amino)-5'-deoxyadenosine, 5'-[(3aminopropyl]-methylamino)-5'-deoxyadenosine, 9-[6(RS)-amino-5,6,7-trideoxy-beta-D-ribo-octofuranosyl]-9H-purin-6-amine, borohydride, n-butylglyoxal bis(guanylhydrazone), 9-[6(RS)-c-carboxamido-5,6,7-trideoxy-beta-D-ribo-octofuranosyl]-9H-purin-6-amine, cyanide, cyanoborohydride, S-(5' deoxy-5'adenosyl)methionylethylhydroxylamine, S-(5' deoxy-5'adenosyl)methionylthiohydroxylamine, 5'-deoxy-5'-[N-methyl-N-[2(aminooxy)ethyl]amino]adenosine, 9-[6(5)-diamino-5,6,7,8,9-pentadeoxy-beta-D-ribo-nanofuranosyl]-9H-purin-6-amine, diethylglyoxal bis(guanylhydrazone), difluorophynylethyl (4-aminopropylamidinohydrazone), dimethyl(5'-adenosylj-sulfonium, dimethylglyoxal bis(guanylhydrazone), ethylglyoxal bis(guanylhydrazone), hydroxylamine, 4-hydroxypenenal, MDL 73811, 5'[[3-methylamino)propyl]amino]-5'-deoxyadenosine(1,1'-(methylethanediylidine) dinitro)bis(3-aminoguanididne), methylglyoxal bis(3-aminopropylamidinohydrazone), methylglyoxal bis(cyclohexylamidinohydrazone), pentanedialdehyde bis(guanylhydrazone), phenylhydrazine, propanedialdehyde bis(guanylhydrazone), semicarbazide, sodium borohydride, sodium cyanoborohydride, and spermine as discussed in Zollner H. (1993) Handbook of Enzyme Inhibitors, 2nd Ed. Additional disclosure may be found in WO2002/053519, the disclosure of which is incorporated by reference as if written herein in its entirety.

Additional spermine analogs include N-(2-mercaptoethyl)spermine-5-carboxamide (MESC), the disulfide from thereof, namely 2,2 1-dithiobis(N-ethyl-spermine-5-carboxamide) (DESC), and N-[2,2,1-dithio(ethyl 1,1-aminoethyl)]spermine-5-carboxamide (DEASC). (WO98/17623)

Polyamine effectors that are small molecule inhibitors or modulators of key enzymes in the polyamine biosynthetic pathway include, but are not limited to: ODC inhibitors such as difluoromethylornithine (DFMO), alpha-monofluoromethylornithine (MFMO), and methyl acetylenicputrescine (MAP); AdometDC inhibitors such as S-(5-deoxy-5adenoxyl)methylthioethylhydroxylamine (AMA), 5-deoxy-5-[(2aminooxyethyl)methyllamino]adenosine (MAOEA), and methylglyoxal bis(guanylhydrazone) (MGBG); spermidine synthase inhibitors such as S-adenosyl1,8-diamino-3-thiooctane (AdoDATO), cyclohexylamine, and butylamine; spermine synthase inhibitors such as S-adenosyl-1,12-diamino-3-thio-9-azadodecane (AdoDATAD) and N-(n-butyl)-1,3-diaminopropane (BDAP).

In certain embodiments, the polyamine effector is a polyamine or arginine analog that carries a functional group that confers a cellular or DNA protective effect to the molecule, or that modulates the polyamine biosynthetic or catabolic pathway. Compounds of this nature include, but are not limited to amifostine, NG-hydroxy-arginine (NORA), N1, N11-bis(ethyl) norspermine (BE-3-3-3), N12-bis(ethyl)spermine (BE-3-4-3), N,N-bis[3-(ethylamino)-propyl]-1,7heptanediamine (BE-3-7-3), BE-3-3-3, BE-3-4-3, BE-3-7-3,N1-ethyl-N11-propargyl 4,8-diazaundecane, and the analogs SL-11141 and SL-I1050 (structures set forth in one or more of U.S. Pat. No. 5,889,061, Valasinas et al., 2001, supra, WO 00/66587 and WO 02/38105). Additional disclosure may be found in WO03/013245, the disclosure of which is incorporated by reference as if written herein in its entirety.

As used herein, the terms below have the meanings indicated.

The term "cytokine," as used herein, alone or in combination, means signaling molecules secreted by cells of the immune system which have a local immunoregulatory effect. Cytokines may include, without limitation, IL-1, IL1-Ra, IL-2, IL-6, IL8, IFNγ, IP-10, IL-17, MCP-1, MMP-9, MIP-1β, TNF-α, TGFβ, CRP, OPN, and RANTES.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "substantially" as used herein is intended to mean predominantly or having the overriding characteristic of, such that any opposing or detracting characteristics reach a level of insignificance. By way of example, a composition "substantially" free of water might not be absolutely free of all traces of water, but would be sufficiently anhydrous that any remaining water would not influence the composition in any significant way. By way of further example, "substantially dose-limiting side effects" might be side effects which limited a dose to a level which was below that required for therapeutic efficacy.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "proliferative disorder" may be any disorder characterized by dysregulated cellular proliferation. Examples include cancers, psoriasis, and atopic dermatitis.

As used herein, "hyperalgesia" means a heightened sensitivity to pain, and can be considered a type of pain or a measure of pain-related behavior.

As used herein, "progressive" multiple sclerosis refers to forms of the disease which progress towards an ever-worsening disease state over a period of time. Progressive MS includes, for example, primary progressive MS, secondary progressive MS, and progressive relapsing MS. These subtypes may or may not feature episodic flare-ups of the disease, but are each associated with increased symptoms, such as increased demyelination or pain and reduced capacity for movement, over time.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and means an animal differing from a disease, disorder, or condition treatable in accordance with the methods disclosed herein, including all mammals and humans Examples of patients include humans, livestock such as cows, goats, sheep, pigs, and rabbits, and companion animals such as dogs, cats, rabbits, and horses. Preferably, the patient is a human.

An "effective amount" or a "therapeutically effective amount" is a quantity of a compound (e.g., MGBG, a polyamine analog, a polyamine biosynthesis inhibitor or any agent) that is sufficient to achieve a desired effect in a subject being treated. For instance, this can be the amount necessary to treat a disease, disorder, condition, or adverse state (such as pain or inflammation) or to otherwise measurably alter or alleviate the symptoms, markers, or mechanisms of the disease, disorder, condition, or adverse state. As just one example, an effective amount for the treatment of pain is an amount sufficient to prevent, delay the onset of, or reduce pain or one or more pain-related symptoms in a subject, as measured by methods known in the art. Similar methods of assessing response to treatment of a number of diseases are well-know in the art. The effective amount of a compound of the present invention may vary depending upon the route of administration and dosage form. In addition, specific dosages may be adjusted depending on conditions of disease, the age, body weight, general health conditions, sex, and diet of the subject, dose intervals, administration routes, excretion rate, and combinations of agents.

The term "low dose," in reference to a low dose formulation of a drug or a method of treatment specifically employing a "low dose" of a drug, means a dose which for at least one indication is subtherapeutic, or is a fraction of the dose typically given for at least one indication. Take for example the case of a drug for the treatment of proliferative disorders—a low dose formulation for the treatment of, say, multiple sclerosis, might be a fraction of the dose for the treatment of an aggressive cancer. In this way, the dose for one disease might be an amount which would be subtherapeutic for another disease. Alternatively, for a drug which is therapeutic in different individuals or populations at different doses, and is available in a range of doses, a low dose may be simply a dose toward the low end of recognized therapeutic efficacy. Chronic diseases represent an embodiment treatable by low dose formulations and methods. Additionally, a subtherapeutic amount of a drug might be used in combination with one or more other drugs (themselves in either therapeutic or subtherapeutic amounts) to yield a combination formulation or treatment which is potentiated, that is, more efficacious than the expected effects of the sum of the drugs given alone. A low dose for the treatment of one indication may be two-fold, three-fold, four-fold, five-fold, six-fold, seven-fold, eight-fold, nine-fold, ten-fold, fifteen-fold, twenty-fold, thirty-fold, forty-fold, fifty-fold, may be one hundred-fold less than the therapeutic dose for a different indication.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of subjects without undue toxicity, irritation, and allergic response, are commensurate with a reasonable benefit/risk ratio, and are effective for their intended use.

The term "drug" is used herein interchangeably with "compound" and "agent."

When a compound is referred to herein as "not a T-cell regulator," what is meant is that any direct activity against T-cells is negligible and/or secondary to activity attributable to another leukocyte subtype. In certain embodiments, a cell which is "not a T-cell regulator" will be a cell of myeloid lineage. In certain embodiments, such a cell will be a dendritic cell, a monocyte, or a macrophage.

The phrase "reduced incidence of at least one side effect" as used herein means reduced to a degree that is significant. Significance can be demonstrated by statistical methods (i.e., by non-overlapping standard deviations or appropriate confidence intervals). Significance of reduced incidence of side effects may also be demonstrated by reference to qualitative measures such as, for example, the ability to achieve or maintain a therapeutic dose without dose-limiting toxicity (in all patients or in a patient subpopulation), the ability to prevent or delay disease relapse or progression, or patient preference.

The phrase "approved for the treatment of a demyelinating disease," as used herein, means approved by a drug regulatory agency (in the United States, Europe or any EPO country, Japan, Canada, or Australia) for the treatment of a demyelinating disease. In any embodiment disclosed herein, the demyelinating disease may be, specifically, multiple sclerosis.

The term "SAMDC inhibitor" means an inhibitor of the enzyme S-adenosyl methionine decarboxylase. MGBG is believed to be one such SAMDC inhibitor, and other polyamines, polyamine analogs, and polyamine biosynthesis inhibitors may also be SAMDC inhibitors.

As used herein, a "polyamine" is any of a group of aliphatic, straight-chain amines derived biosynthetically from amino acids; polyamines are reviewed in Marton et al. (1995) *Ann. Rev. Pharm. Toxicol.* 35:55-91. By "polyamine" is generally meant a naturally-occurring polyamine or a polyamine which is naturally produced in eukaryotic cells. Examples of polyamines include putrescine, spermidine, spermine and cadaverine.

As used herein, a "polyamine analog" is an organic cation structurally similar but non-identical to naturally-occurring polyamines such as spermine and/or spermidine and their precursor, diamine putrescine. Polyamine analogs can be branched or un-branched, or incorporate cyclic moieties. Polyamines may comprise primary, secondary, tertiary, or quaternary amino groups. In one embodiment, all the nitrogen atoms of the polyamine analogs are independently secondary, tertiary, or quaternary amino groups, but are not so limited. Polyamine analogs may include imine, amidine and guanidine groups in place of amine groups. The term "polyamine analog" includes stereoisomers, salts and protected derivatives of polyamine analogs.

A "stereoisomer" is any optical isomer of a compound, including enantiomers and diastereomers. Unless otherwise indicated, structural formulae of compounds are intended to embrace all possible stereoisomers.

A "salt" or "pharmaceutically acceptable salt" is a compound formed by the replacement of one or more hydrogen atoms with elements or groups, which is composed of anions and cations, which usually ionizes in water; a salt is formed, for instance, by neutralization of an acid by a base. Examples of salts include, but are not limited to, halide, for example, chloride, bromide, or iodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl (MesSO$_2$), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkyl" or "aralkyl," as used herein, alone or in combination, refers to an aryl group attached to the parent molecular moiety through an alkyl group. The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle" or "alicyclic," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "halo," or "halogen," as used herein, alone or in combination, refers to fluorine, chlorine, bromine, or iodine.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3- to 15-membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "lower," as used herein, alone or in a combination, where not otherwise specifically defined, means containing from 1 to and including 6 carbon atoms.

The term "sulfonyl," as used herein, alone or in combination, refers to $-S(O)_2-$.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $-CH_2CH_3$), fully substituted (e.g., $-CF_2CF_3$), monosubstituted (e.g., $-CH_2CH_2F$) or substituted at a level anywhere in-between fully substituted and monosubstituted (e.g., $-CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as $-C(O)N(R)-$ may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds disclosed herein to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, drageemaking, levigating, emulsifying, encapsulating, entrapping or compression processes.

The agent—a polyamine analog, polyamine biosynthesis inhibitor, polyamine transport inhibitor, or agent that inhibits SAMDC—may also be administered in combination with one or more entities. In one embodiment, the entity is a therapeutic entity, including, but not limited to, an anti-viral or anti-retroviral agent, a steroid or other anti-inflammatory agent. In another embodiment, the entity is a pharmaceutically acceptable carrier.

The optimal dose, frequency of administration, and duration of treatment with the agent in a subject may vary from subject to subject, depending on the disease to be treated or clinical endpoint to be reached (for example, inhibition of infiltration of macrophages to a tissue, or mitigation of pain) the subject's condition, the subject's age, weight, response to the treatment, and the nature of the therapeutic entity. Determination of the optimal dose and duration of treatment is within the scope of one of skill in the art. The optimal dose and duration of treatment may be best determined by monitoring the subject's response during the course of the treatment. In some instances, the administration of higher doses may permit less frequent administration, and lower doses may require more frequent administration in order to achieve a clinically significant improvement in the subject's condition. The agent(s) of the invention may be administered as a single dose or in multiple doses.

Generally, a therapeutically effective dose of the agent in accordance with the present methods will be one or more doses of from about 10 to about 1100 mg/m$^2$. Lower dose regimens include doses of 10-200, 10-100, 10-50 and 20-200 mg/m$^2$. Higher dose regimens include 200-400, 250-500, 400-600, 500-800 600-1000 and 800-1100 mg/m$^2$. In one embodiment, the dose regimens range from 200-400 mg/m$^2$. In another embodiment, the dose regimens range from 250-500 mg/m$^2$. In yet another embodiment, the dose regimens range from 600-1000 mg/m$^2$. In some embodiments the agent is administered daily, once per week, once every other week, or once per month. In one embodiment, a dose regimen ranging from 200-400 mg/m$^2$ is administered once a week. In another embodiment, a dose regimen ranging from 250-500 mg/m$^2$ is administered once every other week.

The doses may be constant over the entire treatment period, or they may increase or decrease during the course of the treatment. In one embodiment, the agent is administered once a week and starts with the administration of 200 mg/m$^2$, and increases to 300 mg/m$^2$ and 400 mg/m$^2$ in the second and third weeks, respectively. In another embodiment, the agent is administered once every other week and is kept constant for the entire duration of treatment with the administration of 250 mg/m$^2$. The doses of the agent may be administered for at least one week, at least two weeks, at least three weeks, at least four weeks, at least 6 weeks, or even at least 8 weeks. Adjusting the dose of the agent within these ranges for a particular subject is well within the skill of the ordinary clinician.

The agent may be administered via any conventional route normally used to administer a medicament including, but not limited to, oral, parenteral (including subcutaneous, intradermal, intramuscular, intravenous, intraarticular, and intramedullary), intraperitoneal, transmucosal (including nasal), transdermal, rectal and topical (including dermal, buccal, sublingual and intraocular) routes. Intravenous delivery may take place via a bolus injection or via infusion; infusion may be done over a period ranging from less than a minute to several hours to continuously. In certain embodiments, a course of treatment will involve administration by a combination of routes.

For example, the agent may be administered via a combination of intravenous and oral routes for the treatment of pain or another disorder. In one embodiment, a "loading" dose may be administered IV in order to bring the concentration of drug to the desired therapeutic level, followed by one or more maintenance doses via the oral route to keep it there. In a further embodiment, a combination of oral and IV delivery may be used to mitigate pain in a surgery patient. The agent may be delivered pre-, peri-, and post-surgically by a combination of IV and oral routes. In one embodiment, the patient may be administered or may self-administer the drug orally prior to surgery, be administered the drug via IV infusion during surgery and just after, and may thereafter be administered or may self-administer the drug orally after surgery. In another embodiment, the patient may be administered the drug IV prior to surgery, be administered the drug via IV infusion during surgery and just after, and may thereafter be administered or may self-administer the drug orally after surgery.

The agent may be administered as a pharmaceutical composition in a variety of forms including, but not limited to, liquid, powder, suspensions, tablets, pills, capsules, sprays and aerosols. The pharmaceutical compositions may include various pharmaceutically acceptable additives including, but not limited to, carriers, excipients, binders, stabilizers, antimicrobial agents, antioxidants, diluents and/or supports. Examples of suitable excipients and carriers are described, for example, in "Remington's Pharmaceutical Sciences," Mack Pub. Co., New Jersey (1991). In some embodiments, the agent may be administered via an IV infusion in an aqueous sugar solution. The agent may also be associated with another substance that facilitates agent delivery. For example, the agent may be associated into liposomes. The liposomes, in turn, may be conjugated with targeting substance(s), such as IgGFc receptors.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Exemplary unit dosage formulations are those containing an effective dose, as herein below recited, or an appropriate fraction thereof, of the active ingredient.

Fillers to be used in the compositions herein include all those now known and in use, as well as those developed in the future. Examples of fillers, or diluents, include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV® is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. ProSolv comes in different grades based on particle size, and is a white or almost white, fine or granular powder, practically insoluble in water, acetone, ethanol, toluene and dilute acids and in a 50 g/l solution of sodium hydroxide.

Disintegrants to be used in the compositions herein include all those now known and in use, as well as those developed in the future. Examples of disintegrants include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Lubricants to be used in the compositions herein include all those now known and in use, as well as those developed in the future. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Glidants to be used in the compositions herein include all those now known and in use, as well as those developed in the future. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Tablet binders to be used in the compositions herein include all those now known and in use, as well as those developed in the future. Examples of tablet binders include, without limitation, acacia, alginic acid, carbomer, carboxymethyl cellulose sodium, dextrin, ethylcellulose, gelatin, guar gum, hydrogenated vegetable oil, hydroxyethylcellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

Examples of surfactants include, without limitation, fatty acid and alkyl sulfonates; commercial surfactants such as benzethanium chloride (HYAMINE® 1622, available from Lonza, Inc., Fairlawn, N.J.); DOCUSATE SODIUM® (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20, available from Lipochem Inc., Patterson N.J.; CAPMUL® POE-0, available from Abitec Corp., Janesville, Wis.), polyoxyethylene (20) sorbitan monooleate (TWEEN 80®, available from ICI Americas Inc., Wilmington, Del.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug Drug complexing agents and solubilizers to be used in the compositions herein include all those now known and in use, as well as those developed in the future. Examples of drug complexing agents or solubilizers include, without limitation, the polyethylene glycols, caffeine, xanthene, gentisic acid and cylodextrins.

The addition of pH modifiers such as acids, bases, or buffers may also be beneficial, retarding or enhancing the rate of dissolution of the composition, or, alternatively, helping to improve the chemical stability of the composition. Suitable pH modifiers to be used in the compositions herein include all those now known and in use, as well as those developed in the future.

It should be understood that in addition to the ingredients particularly mentioned above, the formulations provided herein may include other agents conventional in the art having regard to the type of formulation in question. Proper formulation is dependent upon the route of administration chosen. Any of the well-known techniques, carriers, and excipients may be used as suitable and as understood in the art; e.g., Remington, supra. The pharmaceutical compositions may be manufactured in a manner that is itself known, e.g., by means of conventional mixing, dissolving, granulating, dragee-making, levigating, emulsifying, encapsulating, entrapping or compression processes.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The precise amount of compound administered to a subject will be the responsibility of the attendant physician. The specific dose level for any particular subject will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity. Dosing frequency may also be selected or adjusted based on factors including those above as well as the formulation of the compound delivered. Dosing may occur, for example: once daily, twice daily, three or four times daily, every other day, weekly, bi-weekly, or monthly; or in cycles comprising a sustained dosing period followed by a non-dosing period; or on an as-needed basis.

In certain instances, it may be appropriate to administer at least one of the compounds described herein (or a pharmaceutically acceptable salt, ester, or prodrug thereof) in combination with another therapeutic agent. By way of example only, if one of the side effects experienced by a subject upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the subject is enhanced). Or, by way of example only, the benefit experienced by a subject may be increased by administering one of the compounds described herein with another therapeutic agent (which also includes a therapeutic regimen) that also has therapeutic benefit. By way of example only, in a treatment for neuropathy involving administration of one of the compounds described herein, increased therapeutic benefit may result by also providing the subject with another therapeutic agent for neuropathy. In any case, regardless of the disease, disorder or condition being treated, the overall benefit experienced by the subject may simply be additive of the two therapeutic agents or the subject may experience a synergistic benefit.

In certain embodiments, the other therapeutic agent is an agent for the treatment of multiple sclerosis such as interferon beta-1a, interferon beta-1b, glatiramer acetate, mitoxantrone, natalizumab, fingolimod, dimethyl fumarate (tecfidera) and teriflunomide, as well as other interferons and immunomodulatory, immunosuppressant, or anti-inflammatory drugs.

In other embodiments, the other therapeutic agent is a TNF inhibitor. The TNF inhibitor may be: a monoclonal antibody such as, for example, infliximab (Remicade), adalimumab (Humira), certolizumab pegol (Cimzia), or golimumab (Simponi); a circulating receptor fusion protein such as etanercept (Enbrel); or a small molecule, such as pentoxifylline or bupropion (Zyban, Wellbutrin).

In other embodiments, the other therapeutic agent is a disease-modifying anti-rheumatic drug (DMARD). Examples of DMARDs include azathioprine, ciclosporin (cyclosporine A), D-penicillamine, gold salts, hydroxychloroquine, leflunomide, methotrexate (MTX), minocycline, sulfasalazine (SSZ), and cyclophosphamide.

In further embodiments, the other therapeutic agent is methotrexate.

Other agents for used in combination include interleukin 1 (IL-1) blockers such as anakinra (Kineret), T-cell costimulation blockers such as abatacept (Orencia), interleukin 6 (IL-6) blockers such as tocilizumab (an anti-IL-6 receptor antibody; RoActemra, Actemra), monoclonal antibodies against B cells such as rituximab (Rituxan), and other biologics (eg. Ocrelizumab, Ofatumumab, Golimumab, and Certolizumab pegol).

In other embodiments, the other therapeutic agent is a glucocorticoid or a non-steroidal anti-inflammatory drug (NSAID). NSAIDS include propionic acid derivatives such as ibuprofen, naproxen, fenoprofen, ketoprofen, flurbiprofen, and oxaprozin; acetic acid derivatives such as indomethacin, sulindac, etodolac, and diclofenac; enolic acid (oxicam) derivatives such as piroxicam and meloxicam; fenamic acid derivatives such as mefenamic acid and meclofenamic acid; selective COX-2 inhibitors (Coxibs) such as celecoxib (Celebrex), rofecoxib, valdecoxib, parecoxib, lumiracoxib, and etoricoxib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the doses of the multiple therapeutic agents may be any duration of time ranging from a few minutes to four weeks.

Thus, in another aspect, certain embodiments provide methods for treating disorders in a human or animal subject in need of such treatment comprising administering to said subject an amount of a compound disclosed herein effective to reduce or prevent said disorder in the subject, optionally in combination with at least one additional agent for the treatment of said disorder that is known in the art. Specific diseases to be treated by the compounds, compositions, and methods disclosed herein, singly or in combination, include, without limitation: pain; neuropathy; inflammation and related disorders; arthritis; metabolic inflammatory disorders; respiratory disorders; autoimmune disorders; neurological disorders; and proliferative disorders, including cancer and non-cancerous diseases.

The compounds disclosed herein are useful to treat patients with pain, including neuropathy and/or neuropathic pain, and inflammatory pain. Pain indications include, but are not limited to, treatment or prophylaxis of surgical or post-surgical pain for various surgical procedures including amputation, post-cardiac surgery, dental pain/dental extraction, pain resulting from cancer, muscular pain, mastalgia, pain resulting from dermal injuries, lower back pain, headaches of various etiologies, including migraine, menstrual cramps, and the like. The compounds are also useful for the treatment of pain-related disorders such as tactile allodynia and hyperalgesia. The pain may be somatogenic (either nociceptive or neuropathic), acute and/or chronic.

Peripheral neuropathies which can be treated with the compounds disclosed herein include mono-neuropathies, mono-multiplex neuropathies, and poly-neuropathies, including axonal and demyelinating neuropathies. Both sensory and motor neuropathies are encompassed. The neuropathy or neuropathic pain may be associated with a number of peripheral neuropathies of varying etiologies, including but not limited to:

trauma-induced neuropathies, including those caused by physical injury (such as blunt trauma, abrasion, or burns) or disease state, physical damage to the brain, physical damage to the spinal cord, or stroke associated with brain damage; neurological disorders related to neurodegeneration; and post-surgical neuropathies and neuropathic pain (such as from tumor resection, mastectomy, and the like)

infectious and viral neuropathies, including those caused by leprosy, Lyme disease, a herpes virus (and more particularly by a herpes zoster virus, which may lead to post-herpetic neuralgia), human immunodeficiency virus (HIV, which may lead to HIV neuropathy), or a papilloma virus, or any other pathogen-induced nerve damage;

toxin-induced neuropathies (including but not limited to neuropathies induced by alcoholism, vitamin B6 intoxication, hexacarbon intoxication, amiodarone, chloramphenicol, disulfiram, isoniazide, gold, lithium, metronidazole, misonidazole, nitrofurantoin);

drug-induced neuropathies, including therapeutic-drug-induced neuropathy, particularly a) chemotherapy-induced neuropathies caused by anti-cancer agents such as taxol, taxotere, cisplatin, nocodazole, vincristine, vindesine and vinblastine, and b) anti-viral neuropathies caused by anti-viral agents such as ddI, DDC, d4T, foscarnet, dapsone, metronidazole, and isoniazid);

vitamin-deficiency-induced neuropathies including those resulting from vitamin B12 deficiency, vitamin B6 deficiency, and vitamin E deficiency);

hereditary neuropathy (including but not limited to Friedreich ataxia, familial amyloid polyneuropathy, Tangier disease, Fabry disease;

diabetic neuropathy and neuropathy caused by metabolic disorders such as renal insufficiency and hypothyroidism;

neuropathy secondary to tumor infiltration, auto-immune neuropathies, including those resulting from Guillain-Barre syndrome, chronic inflammatory de-myelinating polyneuropathy, monoclonal gammopathy of undetermined significance and polyneuropathy, and multiple sclerosis;

other neuropathies and neuropathic pain syndromes including inflammation-induced nerve damage, neurodegeneration, post-traumatic neuralgia, central neuropathic pain syndromes such as phantom limb pain, pain, complex regional pain syndromes (including but not limited to reflex sympathetic dystrophy, causalgia), neoplasia-associated pain, vasculitic/angiopathic neuropathy, and sciatica; and idiopathic neuropathies.

In certain embodiments, neuropathic pain may alternatively be manifested as allodynia, hyperalgesic pain, thermal hyperalgesia, or phantom pain. In another embodiment, neuropathy may instead lead to loss of pain sensitivity. Additional sub-categories of neuropathic pain are discussed in Dworkin, *Clin J Pain* (2002) vol. 18(6) pp. 343-9.

Compounds disclosed herein can also be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds disclosed herein are useful in the treatment or prevention of drug withdrawal symptoms, for example treatment or prevention of symptoms of withdrawal from opiate, alcohol, or tobacco addiction.

Compounds disclosed herein can also be used in the treatment or prevention of respiratory disease or conditions, including: asthmatic conditions including allergen-induced asthma, exercise-induced asthma, pollution-induced asthma, cold-induced asthma, and viral-induced-asthma; chronic obstructive pulmonary diseases including chronic bronchitis with normal airflow, chronic bronchitis with airway obstruction (chronic obstructive bronchitis), emphysema, asthmatic bronchitis, and bullous disease; and other pulmonary diseases involving inflammation including bronchioectasis cystic fibrosis, hypersensitivity pneumonitis, farmer's lung, acute respiratory distress syndrome, pneumonia, aspiration or inhalation injury, fat embolism in the lung, acidosis inflammation of the lung, acute pulmonary edema, acute mountain sickness, acute pulmonary hypertension, persistent pulmonary hypertension of the newborn, perinatal aspiration syndrome, hyaline membrane disease, acute pulmonary thromboembolism, heparin-protamine reactions, sepsis, status asthamticus, hypoxia, hyperoxic lung injuries, and injury induced by inhalation of certain injurious agents including cigarette smoking, leading up to complications thereof such as lung carcinoma.

Compounds disclosed herein can also be used in the treatment or prevention of inflammation and inflammatory conditions. Inflammatory conditions include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritis and vitiligo. In addition, compounds of invention are also useful in organ transplant patients either alone or in combination with conventional immunomodulators.

Compounds disclosed herein can also be used in the treatment or prevention of autoimmune disorders. Autoimmune disorders include Crohns disease, ulcerative colitis, dermatitis, dermatomyositis, diabetes mellitus type 1, Goodpasture's syndrome, Graves' disease, Guillain-Barrésyndrome (GBS), autoimmune encephalomyelitis, Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis. The compounds disclosed herein may regulate TH-17 (T-helper cells producing interleukin 17) cells or IL-17 levels.

Autoimmune disorders may affect the nervous system. Examples of autoimmune disorders affecting the nervous system include polymyalgia, myasthenia gravis, Guillain-Barré Syndrome, chronic inflammatory demyelinating polyneuropathy, transverse myelitis, Balo concentric sclerosis, pernicious anemia, acute disseminated encephalomyelitis (ADME), amyotrophic lateral sclerosis (ALS), autoimmune peripheral neuropathy, lupus erythematosus, psoriatic arthritis, rheumatoid arthritis, osteoarthritis, and rheumatic fever.

Compounds disclosed herein can also be used in the treatment or prevention of demyelinating diseases, including multiple sclerosis (MS), optic neuritis, idiopathic inflammatory demyelinating diseases, Guillain-BarréSyndrome (and sub-types), chronic inflammatory demyelinating polyneuropathy, transverse myelitis, Balo concentric sclerosis, pernicious anemia, central pontine myelinolysis, Tabes dorsalis, neuromyelitis optica (NMO), progressive multifocal leukoencephalopathy (PML), anti-MAG (myelin-associated glycoprotein) neuropathy, hereditary motor and sensory neuropathy (Chacot-Marie-Tooth disease), cerebrotendinious xanthanomatosis, and leukodystrophies including adrenoleukodystrophy, adrenomyeloneuropathy, metachromatic leukodystrophy, globoid cell leukodystrophy (Krabbe disease), Canavan disease, vanishing white matter disease, Alexander disease, Refsum disease, and Pelizaeus-Merzbacher disease.

Compounds disclosed herein can also be used in the treatment or prevention of certain diseases and disorders of the nervous system. Central nervous system disorders in which nitric oxide inhibition is useful include cortical dementias including Alzheimer's disease, central nervous system damage resulting from stroke, ischemias including cerebral ischemia (both focal ischemia, thrombotic stroke and global ischemia (for example, secondary to cardiac arrest), and trauma. Neurodegenerative disorders in which nitric oxide inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen-induced convulsions and toxicity, dementia e.g. pre-senile dementia, and AIDS-related dementia, cachexia, Sydenham's chorea, Huntington's disease, Parkinson's Disease, amyotrophic lateral sclerosis (ALS), Korsakoffs disease, cognitive disorders relating to a cerebral vessel disorder, hypersensitivity, sleeping disorders, schizophrenia, depression, depression or other symptoms associated with Premenstrual Syndrome (PMS), and anxiety.

Compounds disclosed herein can also be used in the treatment or prevention of metabolic disorders that are typically associated with an exaggerated inflammatory signaling, such as insulin resistance, diabetes (type I or type II), metabolic syndrome, nonalcoholic steatohepatitis, atherosclerosis, cardiovascular disease, congestive heart failure, myocarditis, atherosclerosis, and aortic aneurysm.

Compounds disclosed herein can also be used in the treatment or prevention of organ and tissue injury associated with severe burns, sepsis, trauma, wounds, and hemorrhage- or resuscitation-induced hypotension, and also in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, swelling occurring after injury, ischemias including myocardial ischemia, cardiovascular ischemia, and ischemia secondary to cardiac arrest, and the like.

Compounds disclosed herein can also be used in the treatment or prevention of (hyper) proliferative diseases, especially cancers, either alone or in combination of standards of care especially those agents that target tumor growth by re-instating the aberrant apoptotic machinery in the malignant cells. Hematological and non-hematological malignancies which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia(CLL), lymphomas, including Hodgkin's lymphoma and non-Hodgkin's lymphoma (low, intermediate, and high grade), as well as solid tumors and malignancies of the brain, head and neck, breast, lung, reproductive tract, upper digestive tract, pancreas, liver, renal, bladder, prostate and colorectal. The present compounds and methods can also be used to treat the fibrosis, such as that which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP. Non-cancerous proliferative disorders additionally include psoriasis, eczema, and dermatitis.

Compounds disclosed herein can also be used in the treatment or prevention of polycystic kidney disease, as well as other diseases of renal dysfunction.

Compounds disclosed herein can also be used in the treatment or prevention of ophthalmic diseases, such as glaucoma, retinal ganglion degeneration, ocular ischemia, corneal neovascularization, optic neuritis, retinitis, retinopathies such as glaucomatous retinopathy and/or diabetic retinopathy, uveitis, ocular photophobia, dry eye, Sjogren's syndrome, seasonal and chronic allergic conjunctivitis, and of inflammation and pain associated with chronic ocular disorders and acute injury to the eye tissue. The compounds can also be used to treat post-operative inflammation or pain as from ophthalmic surgery such as cataract surgery and refractive surgery.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds of the subject invention may also be used to prevent tissue damage when therapeutically combined with antibacterial or antiviral agents.

Exemplary embodiments of the present methods are provided in the following examples. The following examples are presented to illustrate the methods of the invention and to assist one of ordinary skill in using the same, and are not to be construed as limiting the scope of the invention.

MGBG Oral Activity Assays

The following standard abbreviations are used to represent the associated pharmacokinetic parameters.

AUC Area under the curve up to the last measurable concentration plus the AUC extrapolated from the last measurable concentration ($C_{last}$ at $t_{last}$) to infinity: $AUC_{INFobs}=AUC_{0-tlast}+C_{last}/\text{Lambda z}$ (where λz is the first order rate constant associated with the terminal (log-linear) portion of the curve)

$AUC_{0-12}$ Area under the curve between the time of dose and the 12 h time point $AUC_{0-24}$ Area under the curve between the time of dose and the 24 h time point F Fraction available (bioavailability):
$F=[AUC_{oral}\cdot\text{dose}_{iv}]/[AUC_{iv}]\cdot\text{dose}_{oral}$ $Cl_{obs}$ Observed clearance $Vss_{obs}$ Steady state volume of distribution $V_d$ Volume of distribution (often used with oral)

$Cl/F_{obs}$ Apparent total body clearance as a function of bioavailability $t_{1/2}$ Terminal half-life $(HL)_{\lambda z}$ $C_{max}$ The maximum observed concentration $T_{max}$ The time at which $C_{max}$ occurred Rhesus Macaque Single-Dose Two groups of three male rhesus monkeys were fasted overnight before being administered the test article, MGBG, as either a single bolus intravenous dose of 1 mg/kg (Group 1) or as a single oral gavage dose of 10 mg/kg (Group 2). Dose formulation analysis verified administered dose solutions as within 14% of targeted concentrations of 1 and 10 mg/kg for Groups 1 and 2, respectively.

Blood samples were collected into tubes containing lithium heparin from the femoral vein/artery (approximately 1.0 mL) for plasma MGBG concentration measurement from all intravenously dosed animals prior to dosing and at approximately T=0.083 (5 min), 0.25 (15 min), 0.5 (30 min), 1, 2, 4, 8, and 24 hours after dosing. Blood samples for plasma MGBG concentration measurement were collected from all orally dosed animals prior to dosing at approximately T=1, 2, 4, 8, 12, 24, and 36 hours after dosing. Food was also withheld through the first four hours of blood sample collection.

The samples were centrifuged under refrigerated conditions following completion of sample collection at each interval. The resulting plasma was separated and stored frozen at approximately −70° C. until analysis.

PK analysis was performed on the individual plasma concentration-time profiles for MGBG using the WinNonlin non-compartmental approach (linear trapezoidal rule for AUC calculations). Nominal dose values and sampling times were used for calculations. All MGBG plasma concentration measurements reported as BQL (<2.51 ng/mL) were set equal to zero for the purpose of analysis. Following IV and PO administration of MGBG, plasma PK disposition parameters were calculated using the WinNonlin default selection criteria for the selection of the Lambda Z.

Evidence of systemic plasma MGBG exposure was observed at all collected plasma time points following IV and PO administration of MGBG. Hemolysis was noted in one animal in Group 1 at a single time point, which may have negatively impacted the MGBG plasma concentration analysis for this animal. Consequently, a model-dependent two-compartmental analysis was used to calculate bioavailability.

Dog Single-Dose

Two groups of three male beagle dogs weighing 9.0-10.7 kg and aged 8-30 months were fasted overnight before being administered the test article, MGBG, as either a single bolus intravenous dose of 1 mg/kg (Group 1) or as a single oral gavage dose of 10 mg/kg (Group 2). Dose formulation analysis verified administered dose solutions as within 17% of targeted concentrations of 1 and 10 mg/kg for Groups 1 and 2, respectively.

Blood samples (approximately 2.0 mL) were collected for plasma MGBG concentration measurement from all intravenously dosed animals prior to dosing and at approximately T=0.083 (5 min), 0.25 (15 min), 0.5 (30 min), 1, 2, 4, 8, and 24 hours after dosing. A similar procedure was used with orally dosed animals was used, except that collection took place at T=1, 2, 4, 8, 12, 24, and 36 hours after dosing. The samples were centrifuged under refrigerated conditions following completion of sample collection at each interval. The resulting plasma was separated and stored frozen at approximately −70° C. until analysis.

Analysis was performed by LC/MS/MS, and plasma PK disposition parameters were calculated using the last five plasma concentrations for IV (1-24 h) and PO (4-36 h) administration for the selection of the Lambda Z. Due to inter-animal variability and limited terminal phase data, these results should be interpreted with caution.

No clinically abnormal findings followed IV or oral administration. Systemic exposure was observed at all time points.

Rat Single-Dose

Eighteen male Sprague Dawley rats (Charles River) weighing 217-263 g and aged 8-9 weeks were administered the test article, MGBG as either a single bolus intravenous dose of 1 mg/kg (Group 1) or as a single oral gavage dose of 10 mg/kg. A cohort of three animals was sacrificed via $CO_2$ inhalation anesthesia after final blood collection at each of T=2, 4, 12, 24, 36, and 48 hours post-dose. Dose formulation analysis verified administered dose solutions as within 17% of targeted concentration of 10 mg/kg.

Analysis was performed by LC/MS/MS. Pharmacokinetic analyses were performed on the mean MGBG plasma concentration versus time data using the non-compartmental approach (linear trapezoidal rule for AUC calculations). The WinNonlin sparse sampling tool was used for PK calculations. All samples reported as BLQ (Below the Limit of Quantitation, in plasma 2.50 ng/mL) were changed to 0.00 ng/mL for the purpose of analysis. Dose formulation analysis revealed that formulations were within 15% of the targeted dose concentration of 10 mg/kg.

Abnormal clinical findings were not noted following dosing. A single PO administration of 10 mg/kg of MGBG resulted in evidence of measurable MGBG levels in plasma through the 12 hour time point; beyond that point, certain samples began measure BLQ.

Figure 11:
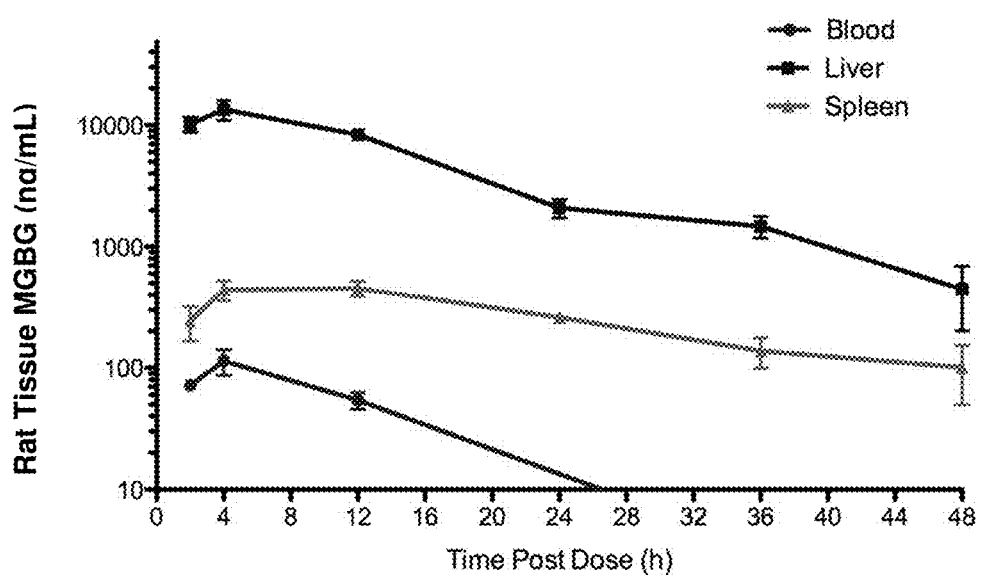
FIG. 11 shows that although plasma levels of MGBG are almost undetectable by 28 hours after a single dose in the rat, MGBG levels in the spleen and liver remain detectably higher even 48 hours post-dose. This is consistent with a selective uptake mechanism for MGBG.
Figure 12:
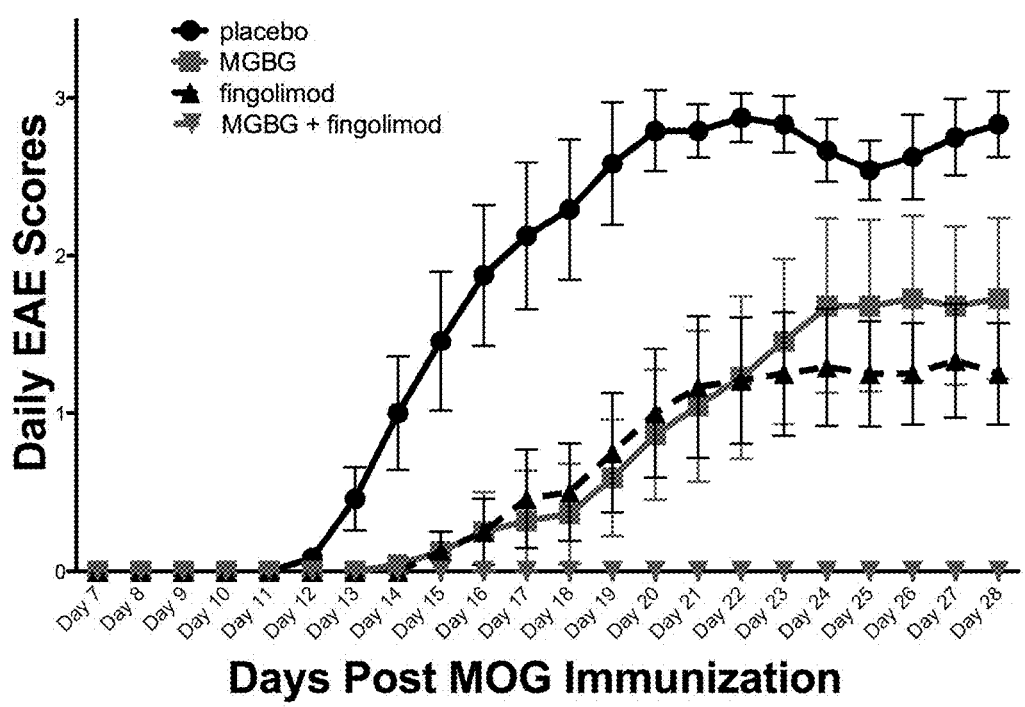
FIG. 12 shows the daily mean clinical scores of subjects in the third 28-day murine MOG EAE model, where fingolimod was dosed at 0.1 mpk (once-daily); MGBG dosed at 30 mpk (twice-daily) suppressed EAE comparably to 0.1 mpk fingolimod, and the combination of MGBG and fingolimod entirely suppressed development of EAE throughout the course of the study (no animals developed disease with the combination therapy).
Figure 13:
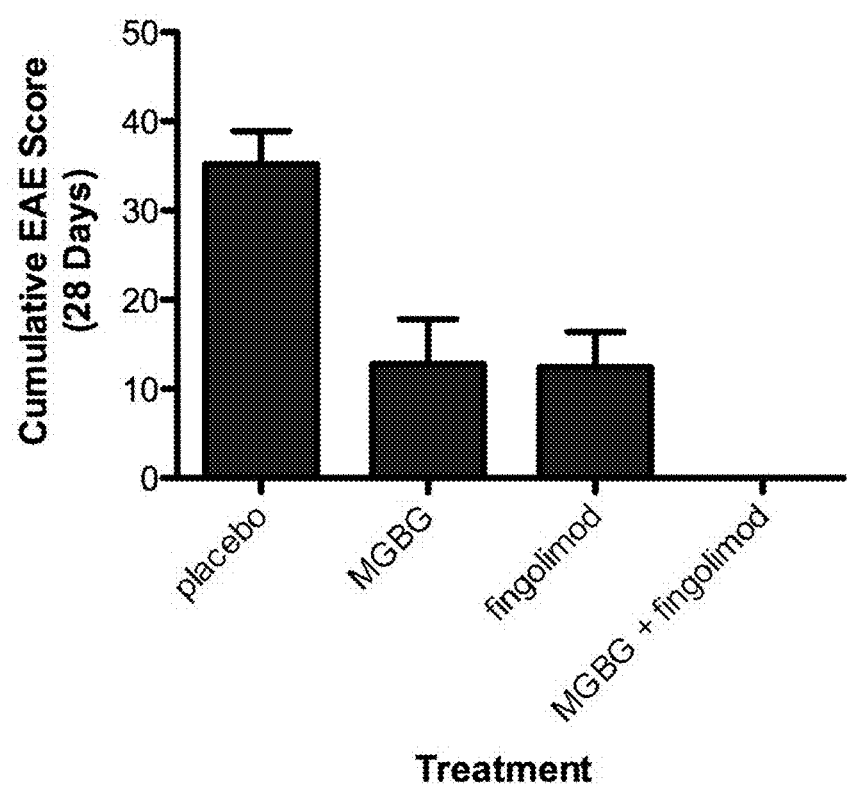
FIG. 13, showing the cumulative mean clinical scores of subjects in the third EAE study, further illustrates the significance of the above results. MGBG at 30 mpk (twice-daily) and fingolimod at 0.1 mpk (once-daily) were equivalently efficacious in preventing EAE development, and the combination of the two entirely suppressed development of EAE.
Figure 14:
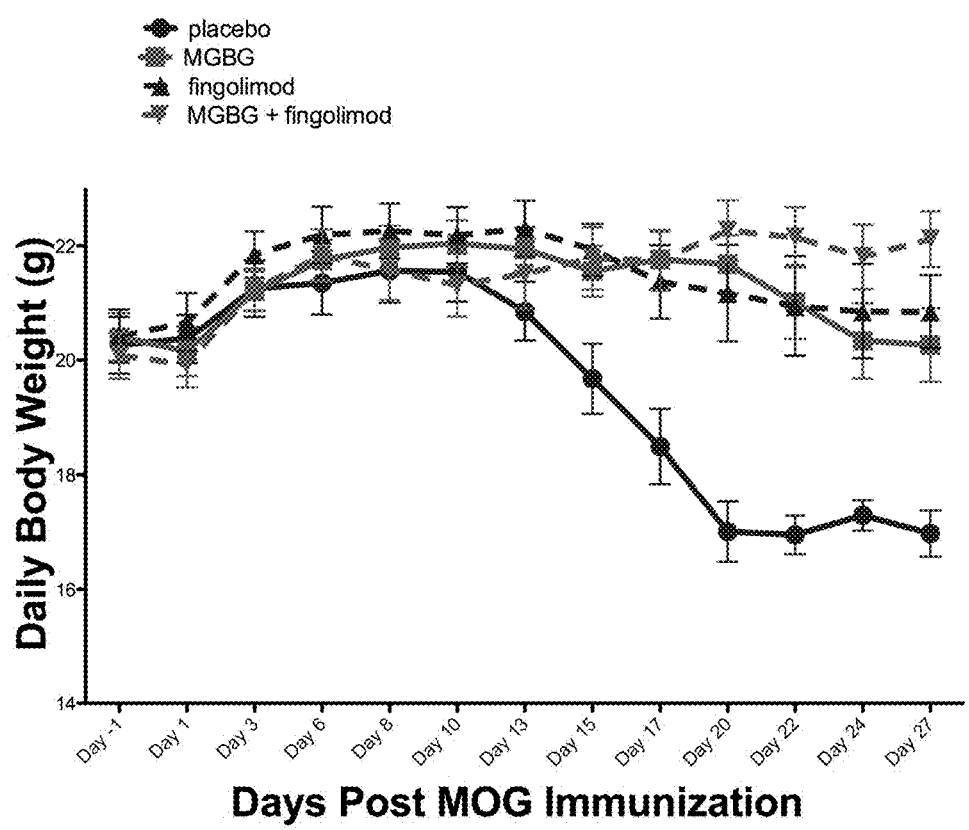
FIG. 14 shows the change in body weight (relative to study start) of subjects in the third 28-day EAE model, corroborating the results in FIG. 13.
Figure 15:
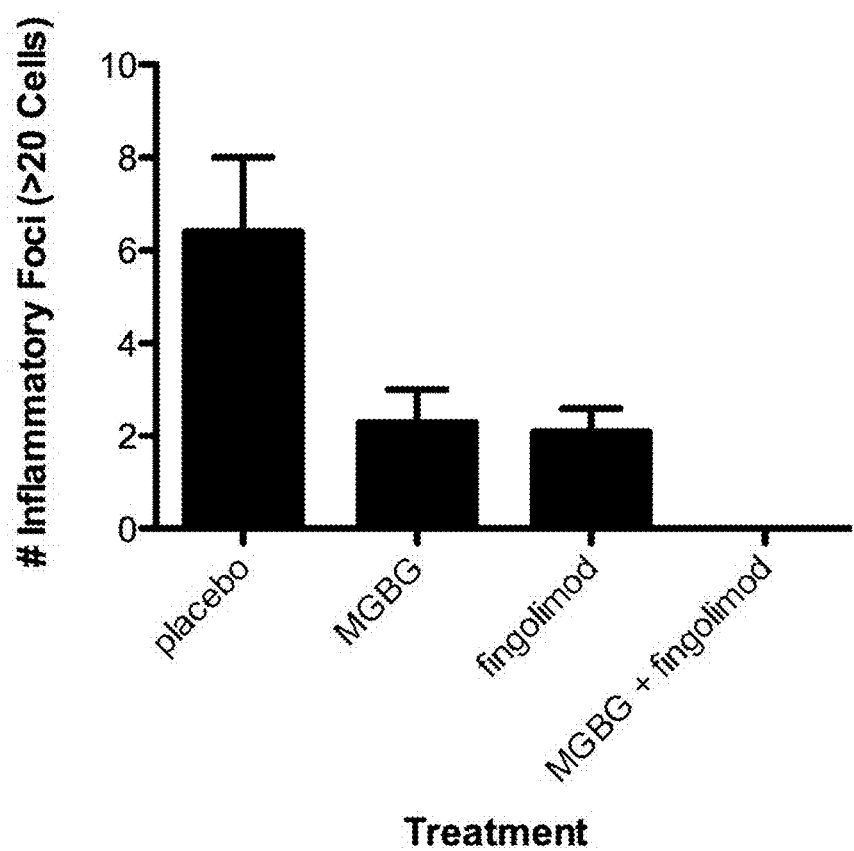
FIG. 15 shows the reduction in spinal cord inflammation as measured by the number of inflammatory foci in spinal cord histopathological samples, from the third EAE model. Again, MGBG at 30 mpk (twice-daily) and fingolimod at 0.1 mpk (once-daily) were equivalently efficacious in reducing the number of inflammatory foci, and the combination of the two apparently suppressed their development completely.
Figure 16:
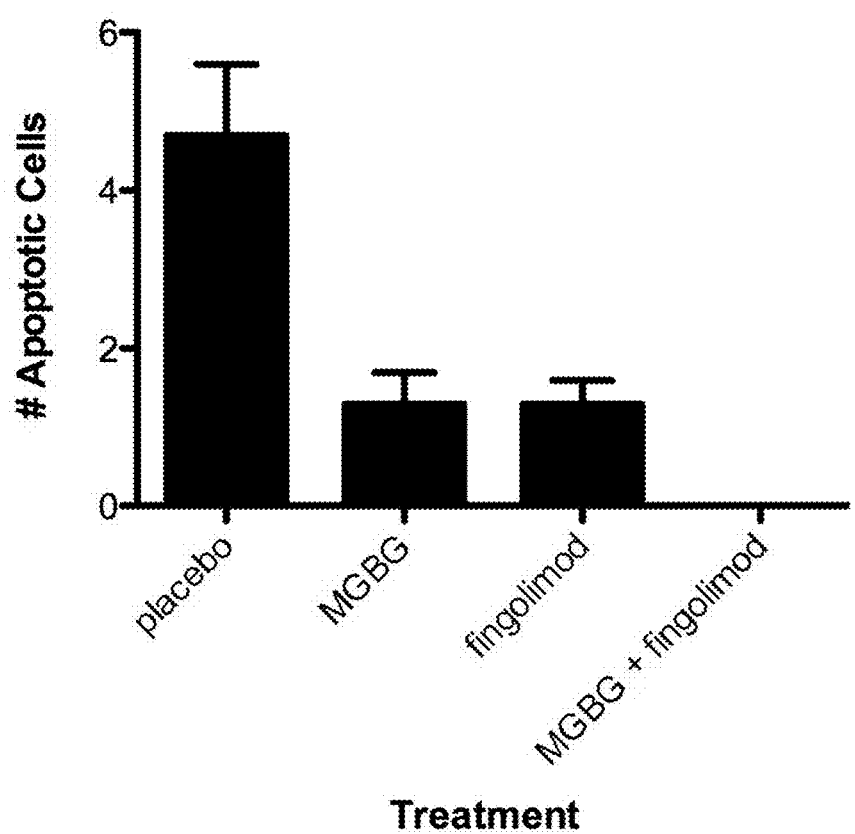
FIG. 16 shows the reduction in cellular apoptosis in spinal cord histopathological samples from the third EAE model. Again, MGBG at 30 mpk (twice-daily) and fingolimod at 0.1 mpk (once-daily) were equivalently efficacious in reducing apoptosis, and the combination of the two apparently suppressed apoptosis completely.
Figure 17:
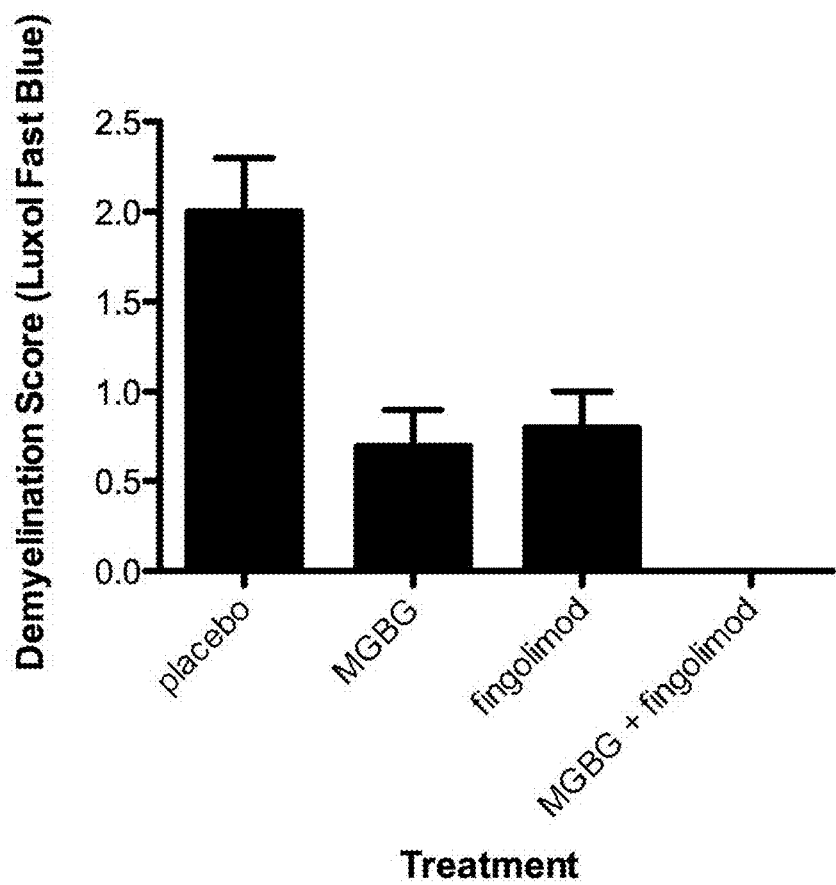
FIG. 17 shows reduction in spinal cord demyelination in histopathological samples from the third EAE model. Again, MGBG at 30 mpk (twice-daily) and fingolimod at 0.1 mpk (once-daily) were equivalently efficacious in reducing demyelination, and the combination of the two apparently prevented demyelination completely.

Additionally, in rats dosed as above with single oral administration of MGBG at 10 mg/kg, immediately following the plasma sample collection for each cohort (i.e., 2, 4, 12, 24, 36, and 48 hours after dosing), three rats were sacrificed, and spleen and liver tissues collected and flask frozen. As shown on FIG. 11, a single oral administration of MGBG at 10 mg/kg resulted in greater overall exposure (as assessed by $C_{max}$ and $AUC_{all}$) of MGBG to liver (120- and 160-fold, respectively) and spleen (4.0- and 9.3-fold, respectively) tissue compared to plasma. This is consistent with a selective uptake mechanism for MGBG. Without wishing to be bound by theory, other SAMDC inhibitors which are selectively uptaken by cells may, like MGBG, be useful in the methods and compositions disclosed herein.

Mouse Single-Dose

Twenty-four male DBA/1 mice weighing 19.5-24.7 g and aged 7-9 weeks administered the test article, MGBG, as either a single bolus intravenous dose via a lateral tail vein of 1 mg/kg (Group 1, n=12) or as a single oral gavage dose of 10 mg/kg (Group 2, n=12). Each dose group consisted of 4 cohorts of 3 animals each. Group 1 was sampled at 5, 15, and 30 minutes after dosing; and 1, 2, 4, 8, and 24 hours after dosing. Group 2 was sampled at 1, 2, 4, 8, 12, 24, and 36 hours after dosing. Starting with the first time point, a new cohort was sampled at each successive time point up to the 1-hour (Group 1) or 12-hour (Group 2) time point. The order of sampling among the cohorts was repeated for the subsequent time points (some cohorts may have been bled only once). The second bleed for each cohort was terminal. Animals were sacrificed via $CO_2$ inhalation anesthesia after final blood collection.

The samples were centrifuged under refrigerated conditions following completion of sample collection at each interval. The resulting plasma was separated and stored frozen at approximately −70° C. until analysis. Analysis was performed by LC/MS/MS. Pharmacokinetic analyses were performed on the mean MGBG plasma concentration versus time data using the non-compartmental approach (linear trapezoidal rule for AUC calculations). The WinNonlin sparse sampling tool was used for PK calculations. Dose formulation analysis revealed that the IV and PO formulations were within 15% of their targeted concentrations.

Abnormal clinical findings were not noted following dosing. Evidence of systemic plasma MGBG exposure was observed at all collected plasma time points following IV and PO administration of MGBG.

Results of the foregoing assays are shown below in Tables 2 and 3. Values reported are mean across treatment groups without standard deviation.

TABLE 2

| IV | $t_{1/2}$ (h) | $T_{max}$ (h) | $C_{max}$ (ng/mL) | $Cl_{obs}$ (mL/min/kg) | $V_{SSobs}$ (L/kg) | AUC (h * ng/mL) |
|---|---|---|---|---|---|---|
| rhesus | 30.8 | 0.139 | 757 | 13.7 | 13.2 | 1660 |
| rat | 17.4 | 0.083 | 684 | 13.4 | 15.4 | 1250 |
| mouse | 13 | 0.083 | 181 | 49.6 | 38.3 | 336 |
| dog | 15.8 | 0.083 | 1180 | 13.7 | 14.6 | 1410 |

TABLE 3

| ORAL | $t_{1/2}$ (h) | $T_{max}$ (h) | $C_{max}$ (ng/mL) | AUC (h * ng/mL) | $Cl_{obs}$ (mL/min/kg) | $V_d$ (L/kg) | F % |
|---|---|---|---|---|---|---|---|
| rhesus | 24.2 | 3.33 | 192 | 4240 | 6.63 | 13.2 | 35.0% |
| rat | 28.1 | 4.67 | 55.8 | 1280** | 3.18 | 15.4 | 11.6% |
| mouse | 11.8 | 1 | 106 | 1420 | 6.68 | 38.3 | 44.3% |
| dog | 15.5 | 1 | 616 | 6290 | 8.29 | 14.6 | 49.0% |

In Table 2 above, the double asterisk indicates that the rat AUC reported is the $AUC_{all}$, computed from time zero to the time of the last plasma concentration measurement. Each of these values carries the caveat that terminal measurements are subject to different methods of extrapolation.

Multi-Dose Rat Pharmacokinetic and Tolerability Study

The purpose of this study was to determine the pharmacokinetic (PK) properties and tolerability of MGBG in rats. Additionally, recovery from any toxic effects was assessed after a seven day non-dosing period. Tolerability was demonstrated in test article-treated animals by body weight changes similar to the control group and a lack of adverse clinical observations.

Three per group of male Sprague Dawley (CD® IGS, Charles River) aged 7-9 weeks and weighing 222.7-252.0 g were administered by oral (PO) gavage, twice daily, at 10, 20, or 30 mg/kg/dose (20, 40, or 60 mg/kg/day) for seven consecutive days. A washout period of seven days followed. Collection of approximately 200 µL of whole blood was collected from the tail vein of all animals in Groups 5, 6, and 7 were bled at six (Day 1), seven (Day 7), or one (Days 9 through 15) time point(s), respectively. Whole blood samples were collected in a lithium heparin microtainer and processed to plasma by centrifugation. Plasma was frozen at −70° C. Pharmacokinetic analyses were performed on the individual animal plasma concentration versus time data for MGBG using WinNonlin (linear trapezoidal rule for AUC calculations). Nominal dose values and sampling times were used for calculations. For Study Day 7, the reported values for MGBG concentrations at time zero were used in the calculations of AUC. Study Day 1 disposition parameters were not reported due to insufficient terminal phase data to adequately characterize these parameters. Following PO administration of MGBG on Study Day 7, plasma PK disposition parameters were calculated on plasma concentrations obtained following the second administered dose (T=12-192 h) using the WinNonlin default selection criteria for the selection of the Lambda Z, the elimination rate constant, upon which half-life, $AUC_{INFobs}$, and $Cl/F_{obs}$, were based; inter-animal variability was noted.

Plasma samples collected from test article-treated animals on Day 1 and Day 7 were subjected to bioanalysis and confirmed systemic exposure to the test article at all time points. Over the dose range evaluated, $T_{max}$ values were dose-dependent and ranged from 3.33 to 14.0 h, and indicated absorption was slightly delayed on Study Day 7 compared to Study Day 1. Systemic exposure (as assessed by $C_{max}$ and $AUC_{all}$) increased with increasing dose, and the increase in both parameters was slightly less than dose-proportional at each evaluation interval. Repeat, twice-daily PO dosing of MGBG was associated with 3.77-, 4.03-, and 3.68-fold increases in mean $AUC_{all}$ values compared to Study Day 1 for the 20, 40, and 60 mg/kg/day dose groups, respectively. On Study Day 7, evidence of dose-dependent dispositions for $Cl/F_{obs}$ and elimination half-life were observed as mean parameter values for $Cl/F_{obs}$ and elimination half-life increased and decreased, respectively, with increasing dose levels.

Differences between the control group and the 60 mg/kg/day dose group were noted for a few hematology parameters (lower reticulocyte count and percentage) and some serum chemistry parameters (e.g., osmolality and electrolyte changes consistent with slight dehydration). However, these changes were not thought to be adverse as they did not coincide with other signs of frank toxicity and the serum chemistry changes were demonstrated to be reversible. No gross or microscopic lesions were observed in test article-treated animals at terminal sacrifice, and no gross lesions were observed in test article-treated animals at recovery sacrifice.

Based on the findings of this exploratory study, the no observable adverse effect level (NOAEL) for MGBG administered by PO gavage twice daily for seven consecutive days to male Sprague Dawley rats is 30 mg/kg/dose (60 mg/kg/day).

TABLE 4

| PO Dose Day 1 (mg/kg/day) | $C_{max}$ (ng/mL) | $T_{max}$ (h) | AUC (h * ng/mL) | $AUC_{0-12}$ (h * ng/mL) | $AUC_{0-24}$ (h * ng/mL) | $Cl/F_{obs}$ |
|---|---|---|---|---|---|---|
| 20 | 124 | 10 | NC | 773 | 1750 | NC |
| 40 | 175 | 7.33 | NC | 1380 | 2980 | NC |
| 60 | 296 | 3.33 | NC | 2170 | 4380 | NC |

TABLE 5

| PO Dose Day 7 (mg/kg/day) | $C_{max}$ (ng/mL) | $T_{max}$ (h) | AUC (h * ng/mL) | $AUC_{0-12}$ (h * ng/mL) | $AUC_{0-24}$ (h * ng/mL) | $Cl/F_{obs}$ |
|---|---|---|---|---|---|---|
| 20 | 117 | 14 | 7930 | 1030 | 2190 | 24.3 |
| 40 | 194 | 9.33 | 13700 | 1800 | 3690 | 28.2 |
| 60 | 337 | 7.33 | 17100 | 3130 | 6040 | 35.8 |

Allometric Scaling and Predicted Human Efficacy

Multi-species allometric scaling based on pharmacokinetic parameters disclosed in Tables 2 and 3 was employed to calculate predicted pharmacokinetic parameters in humans according to methods known in the art. See, e.g., Ings R M, "Interspecies scaling and comparisons in drug development and toxicokinetics," Xenobiotica, 1990 November; 20(11):1201-31 and Khor, S P et al., "Dihydropyrimidine dehydrogenase inactivation and 5-fluorouracil pharmacokinetics: allometric scaling of animal data, pharmacokinetics and toxicodynamics of 5-fluorouracil in humans," Cancer Chemother Pharmacol (1997) 39(3): 833-38. Expected values are given below in Tables 6 and 7.

TABLE 6

| IV | $t_{1/2}$ (h) | CL (mL/min/kg) | Vss (L/kg) |
|---|---|---|---|
| Based on Mouse, Rat, Dog, Rhesus | 13.4 | 7.7 | 9.0 |
| Based on Mouse, Dog, Rhesus | 13.3 | 7.9 | 9.1 |

TABLE 7

| ORAL | $t_{1/2}$ (h) | CL (mL/min/kg) | Vss (L/kg) |
|---|---|---|---|
| Based on Mouse, Rat, Dog, Rhesus | 23.3 | 21.0 | 42.4 |
| Based on Mouse, Dog, Rhesus | 23.0 | 20.9 | 41.6 |

In both the murine carrageenan-induced paw edema and hyperalgesia models, the top efficacious dose of MGBG is 30 mg/kg PO BID (totaling 60 mg/kg/day). Based upon this dosing paradigm in mice, at least two methods to estimate the equivalent dosing in humans may be used.

The first method is based upon body surface area (BSA) normalization (described in Reagen-Shaw et al. (2007) FASEB J. 22, 659-661), as the authors note that BSA correlates well across species for various biological parameters, including basal metabolic rate, blood volume, caloric expenditure, plasma protein levels, and renal function. Using this method, a 60 mg/kg/day dose in mice would convert to about 4.9 mg/kg/day in humans.

The second method used to convert the efficacious 60 mg/kg/day dose in mice to an equivalent dose in humans was based more directly on allometric scaling. Data from an MGBG pharmacokinetic study consisting of a 10 mg/kg oral dose in mice was modeled in a simulation to determine the theoretical AUCINF value for a dosing regimen of 30 mg/kg PO BID, which was 9050 h*ng/mL. Next, predicted human clearance values as determined by single- and multi-species allometric scaling were used to estimate doses likely to produce an exposure in humans (AUCINF) similar to that of the 60 mg/kg/day in mice. Using single-species allometric scaling and a range of predicted human clearance values, a human equivalent dose would be in the range of 1.73 mg/kg/day to 4.51 mg/kg/day. Using multi-species allometric scaling, the predicted human equivalent dose is about 4.2 mg/kg/day.

In the murine carrageenan models, we also observed efficacy of MGBG at lower doses, including 3 mg/kg PO BID and 10 mg/kg PO BID, which would proportionally convert to human doses of ~0.49 mg/kg/day and ~1.6 mg/kg/day.

The average body weight of a normal male human is often presumed to be 70 kg. Thus, daily doses based on the predictions above could be estimated to range from about 25 mg/day to about 350 mg/day.

The proper dose depends, of course, on a number of factors. The patient may weigh much more or much less, or be female, elderly, or juvenile, requiring a lower or higher dose. The patient may exhibit a drug metabolic profile which might counsel for a lower or higher dose, such as a low expression level or activity of metabolizing enzymes such as cytochromes P450 (CYPs). This low expression or activity level may be due to a number of factors. Polymorphic expression of one or more CYPs (for example CYP2C19 and CYP2D6, though polymorphisms have been described for nearly all the CYPs) is known to be responsible for some populations to be "deficient" as compared to the population at large, leading to a "poor metabolizer" phenotype, requiring a lower dose. Additionally, exposure to an infectious agent or xenobiotic may cause repression of CYP expression or inhibition of existing CYPs. Alternatively, the patient may be physically weak, injured, or immunocompromised, all of which might counsel a lower dose. The patient may be taking a number of other drugs which compete with metabolic systems (including CYPs as discussed above) for disposal; this well-know polypharmaceutical effect may call for a lower dose. The dose also depends, as discussed above, on the condition and its severity. The efficacious dose for one disease or clinical endpoint will not necessarily be the same as the dose for another, and a severe, chronic, or otherwise serious case may call for a higher dose. However, a chronic case may also call for a lower dose administered over a longer or even indefinite period of time. All of these are discussed by way of example to illustrate the variability of ideal dosing; it is within the capacity of the skilled artisan to select an appropriate dosing range for a disease, population, or individual.

With these factors in mind, it should be clear that it is possible that the daily human dose may be as low as 1 mg/day, and as high as a 1 g/day. In certain embodiments, the human dose may range: from 10 mg/day to 500 mg/day, from 20 mg/day to 400 mg/day, or from 25 mg/day to 350 mg/day. In further embodiments, the human dose may range: from 120 mg/day to 350 mg/day, from 150 mg/day to 350 mg/day, from 200 mg/day to 350 mg/day, or from 250 mg/day to 350 mg/day. In certain embodiments, the human dose may be any one of 1, 2, 3, 4, 5, 6, 7, 8, 9, 10, 12, 15, 20, 25, 30, 35, 40, 45, 50, 55, 60, 65, 70 75, 80, 85, 90, 95, 100, 110, 120, 125, 130, 140, 150, 160, 170, 175, 180, 190, 200, 210, 220, 225, 230, 240, 250, 260, 270, 275, 280, 290, 300, 310, 320, 325, 330, 240 or 350 mg/day.

In certain embodiments, the human dose may be any one of 275, 280, 285, 290, 295, 300, 305, 310, 315, 320, 325, 330, 335, 340, 350, 355, 360, 365, 370, or 375 mg/day. In one embodiment, the dose may be 275 mg/day. In another embodiment, the dose may be 300 mg/day. In another embodiment, the dose may be 305 mg/day. In another embodiment, the dose may be 310 mg/day. In another embodiment, the dose may be 315 mg/day. In another embodiment, the dose may be 320 mg/day. In another embodiment, the dose may be 325 mg/day. In another embodiment, the dose may be 330 mg/day. In another embodiment, the dose may be 335 mg/day. In another embodiment, the dose may be 340 mg/day. In another embodiment, the dose may be 345 mg/day. In another embodiment, the dose may be 350 mg/day.

In certain embodiments, the human dose may be any one of 350, 375, 400, 425, 450, 475, 500, 525, 550 or 600 mg/day. In one embodiment, the dose may be 375 mg/day. In another embodiment, the dose may be 400 mg/day. In another embodiment, the dose may be 450 mg/day. In another embodiment, the dose may be 500 mg/day.

In certain embodiments, the human dose may be any one of 25, 50, 75, 100, or 125 mg/day. In one embodiment, the dose may be 375 mg/day. In another embodiment, the dose may be 25 mg/day. In another embodiment, the dose may be 50 mg/day. In another embodiment, the dose may be 75 mg/day. In another embodiment, the dose may be 100 mg/day. In another embodiment, the dose may be 125 mg/day.

In Vivo Carrageenan Tests

Carrageenan Paw Test for Edema and Hyperalgesia

Injection of carrageenan subcutaneously into the hind foot (paw) of a rat or mouse induces robust inflammation and pain. The inflammatory response begins 1-2 hrs post-carrageenan injection and persists for at least five hours following inoculation. In addition, the animal's inflamed hind paw is sensitive to noxious (hyperalgesia) or innocuous (allodynia) stimuli, compared to the contralateral hind paw. Compounds can be evaluated in this model for anti-hyperalgesia and anti-inflammatory activity. A general increase in threshold or time to respond following drug administration suggests analgesic efficacy. A general decrease in paw swelling following drug administration suggests anti-inflammatory efficacy. It is possible that some compounds will affect the inflamed paw and not affect the responses of the contralateral paw.

Embodiments of the carrageenan foot edema test are performed with materials, reagents and procedures essentially as described by Winter, et al., (Proc. Soc. Exp. Biol. Med., 111, 544 (1962)). Prophylactic and therapeutic embodiments have been developed, and are known in the art. The animals are evaluated for their responsiveness to noxious (paw pinch, plantar test) or innocuous (cold plate, von Frey filaments) stimuli. In the following protocol, mice were used.

Animals, compounds, and dosing. Healthy young male Swiss Webster mice in which weight variation of the mice will not exceed ±20% of the mean were used for the study. Animals were divided into four groups of forty, and each group was dosed by oral gavage with either MGBG (BID, 12 hours apart at 30 mg/kg in 5 mL/kg normal saline), dexamethasone as positive control (QD, 1 mg/kg in 5 mL/kg 0.5% methylcellulose), or saline vehicle (BID, 5 mL/kg). A fourth group served as naïve control (no carrageenan, no treatment). Treatment with MGBG took place on each of three days prior to carrageenan, one hour prior to carrageenan, and 11 hours post-carrageenan. Paw edema is developed by injecting carrageenan (Sigma: λ-carrageenan) subcutaneously in the subplantar region of the right paw of the mouse at a volume of 50 μL of 1% carrageenan (w/v) in saline. The contra-lateral paw (left paw) received the same volume (50 μL) of saline and serve as control. Mice will be anesthetized using light dose of ketamine before carrageenan injection.

Paw Edema. Immediately before sub-plantar administration of carrageenan and after 2, 3, 5 and 24 hours post carrageenan, mouse paw volume was measured using the plethysmometer (Ugo Basile). The assessment of edema was expressed as the mean increase in paw volume relative to control.

Assessment of Paw Withdrawal Latency. Prior to subplantar administration of carrageenan and after 0.5, 2, 3, 5, and 24 hours post-carrageenan, the latency of withdrawal response was determined by placing mice on a hot plate analgesia meter with surface temperature maintained at 51° C. A cut-off period of 30s was maintained to avoid any thermal injury to paw Immediately after testing, all paws were immersed in ice-cold water before returning to the cage. Paw withdrawal latency is calculated as Δt=right paw withdrawal−left paw withdrawal.

Serum, Plasma, and Histological Collection. Prior to first drug dose on day 0 and at peak disease times (5 and 24 hours post-carrageenan challenge for serum, prior to first drug dose on day 0 and at conclusion of study), serum or plasma was collected from eight mice per group (each) and stored at −70° C. until cytokine level determination or MGBG drug level determination. For serum collection, whole blood samples are collected in a serum separator tube, processed by centrifugation and frozen at −70° C. For drug level determination, whole blood samples are collected in a lithium heparin microtainer, processed to plasma by centrifugation and plasma frozen at −70° C. Additionally, paws are collected and preserved in 10% formalin for histology.

Alternative Protocol. In an alternative embodiment of this assay, MGBG was dosed PO, BID at 3, 10, and 30 mg/kg (with dexamethasone as positive control, saline as negative, and a treatment/carrageenan-naïve group, n=16 each).

Results. MGBG was efficacious in reducing edema and hyperalgesia in the above assay.

Carrageenan Air Pouch Model

Injection of air subcutaneously will induce the formation of a connective tissue cavity lined with cells that resemble and function like a synovial lining. This method is commonly known as the Air Pouch Model and is a useful animal model of inflammation that can be generated in a relatively short period of time. The air pouch may be created by subcutaneous (SQ) injection of a volume of sterile air in the dorsal neck region. The model may be used to test the efficacy and potency of compounds such as polyamine analogues and polyamine biosynthesis inhibitors such as MGBG in reducing various cellular and biochemical indicators of inflammation when administered as an oral (PO) gavage administration.

Animals, compounds, and dosing. Healthy Male Lewis rats (Charles River Laboratories, Wilmington, Mass.) weighing between 175-200 g were used. MGBG at doses between 1 and 60 mg/kg or vehicle (0.5% methylcellulose, 0.025% Tween-80) were administered by oral gavage (once daily at a volume of 10 mL/kg) for 6 days. A correction factor of 1.49 was used to account for the dihydrochloride salt/monohydrate form of MGBG. Naproxen and dexamethasone at doses of 10 and 1 mg/kg, respectively, were dosed 1 day prior to, as well as the morning of, carrageenan injection.

Air pouches were formed on the dorsum of the rats during the last 4 days of MGBG or vehicle administration prior to carrageenan injection. Briefly, rats were anesthetized with isoflurane, during which dorsal hair was removed and 20 mL of sterile air was injected subcutaneously into the intrascapular region. Pouches were allowed to develop for the next 4 days, with re-inflation (to maintain pouch volume) of pouches 1 day prior to carrageenan injection.

One hour prior to carrageenan injection, animals were given their last dose of drug (MGBG, vehicle, naproxen, or dexamethasone). A 1% suspension of carrageenan (2 mL; FMC BioPolyer, Philadelphia, Pa.) suspended in saline was injected into the pouch cavity. At either 3 hours or 24 hours post-carrageenan injection, rats were euthanized by $CO_2$ asphyxiation and 2.5 mL of PBS (Sigma Chemical, St. Louis, Mo.) was injected directly into the pouch. The pouch was opened with surgical scissors and the pouch fluid was collected using a transfer pipette. One aliquot was collected for measurement of total cell count with differential, and the other aliquot for $PGE_2$ determination. In the latter case, the aliquot was centrifuged at 1200 g for 10 minutes at 4° C. and the supernatant was collected for analysis of $PGE_2$ via ELISA (Cayman Chemical Company, Ann Arbor, Mich.).

Samples for the 3- and 24-hour groups were collected as previously described at either 3 or 24 hours post carrageenan injection.

The protocol may be varied according to methods known in the art. Additional tissue may be collected and/or weighed, and additional sectioning, staining, and microscopic examination may be conducted.

Results.

MGBG was efficacious in this model, as shown by changes relative to control indicative of reduced inflammation. Fundamentally, MGBG selectively inhibited peak inflammatory production of PGE2, without affecting basal levels of this mediator. By contrast, both naproxen and dexamethasone inhibited production of both inflammatory and basal levels of this mediator.

In Vivo Murine Collagen-Induced Arthritis

Collagen-Induced Arthritis Models of Arthritis and Rheumatoid Arthritis

The collagen-induced arthritis (CIA) model is considered a suitable model for studying potential drugs active in human arthritis because of the many immunological and pathological similarities to human rheumatoid arthritis (RA), the involvement of localized major histocompatibility, complete class-II-restricted T helper lymphocyte activation, and the similarity of histological lesions. See, e.g., Rosloniec E F et al., "Collagen-Induced Arthritis," *Current Protocols in Immunology*, Unit 15.5 (1993). See also the model using a monoclonal antibody to CD18 and VLA-4 integrins described in Issekutz, A. C. et al., *Immunology* (1996) 88:569. Features of this CIA model that are similar to that found in RA patients include, without limitation: erosion of cartilage and bone at joint margins (as can be seen in radiographs), proliferative synovitis, symmetrical involvement of small and medium-sized peripheral joints in the appendicular, but not the axial, skeleton. The following procedure was followed to assess the efficacy of MGBG in the treatment of arthritic diseases.

Animals and dosing. Inbred male DBA/1 mice (DBA/1O1aHsd, Harlan Laboratories), at least 7 weeks old, may be used in the following collagen-induced arthritis model. Twenty animals per compound or vehicle are assigned to the arthritis and saline groups, 4 to the control group. To induce an arthritic state, mice are anesthetized with isoflurane and given 1501 μL of bovine type II collagen in Freund's complete adjuvant injections (day 0 and day 21). Mice are randomized by body weight into treatment groups on study day 7. Treatment consists of 25 mg/kg MGBG, 0.2 mg/kg dexamethasone as positive control, or saline as vehicle control, all given as oral gavage beginning on study day 0 and continuing daily (PO, BID twice daily/12 hours apart). Twenty mice per group may be used, in which serum is collected from 15 animals, and plasma from five. Four additional animals serve as normal (untreated, non-arthritic) control group. The in-life portion of the study may proceed for 35 days.

Compounds. MGBG solution may be made from the hydrated dihydrochloride salt; other salts could be used, and in any case a salt/hydrate correction factor should be implemented. Solid MGBG can be stored at room temperature, but dose formulations should be made fresh for each administration. Dexamethasone is commercially available.

Data. On days 21-35, onset of arthritis typically occurs. During this time clinical scores for paw edema and swelling were given for each of the paws (right front, left front, right rear, left rear). Plasma draws are taken on days 0, 14, and 25 to assess pharmacokinetics, and blood draws taken on days 0 and 28 for disease analysis. Edema is measured on days 18-20, 22-27, and 29-34. Inflammation is assessed by infiltration of inflammatory cells and edema. Post-euthanasia, terminal blood draws are collected, heparinized, and frozen at −70° C. until analyzed for cytokines such as osteopontin, TNFalpha, IL-1, CRP, MCP1, MIP-1beta, RANTES, IFNgamma, TGFbeta, IP-10, IL-17, and MMP9. Fore and hind paws and knees are collected, and following 1-2 days in fixative and then 4-5 days in decalcifier, processed, embedded, sectioned and stained with toluidine blue for histological analysis. Bone resorption is quantified by presence of osteoclasts, defects in or loss of medullary trabecular or cortical bone. Cartilage damage is assessed by examining the severity and spread of chondrocyte loss and collagen disruption. Pannus tissue formation and the severity and spread of other evidence of destruction of joint architecture are followed.

Statistical Analysis. Clinical data for paw scores (means for animal) are analyzed by determining the area under the dosing curve (AUC) for days 1-15. For calculation of AUC, the daily mean scores for each mouse are entered into Microsoft Excel and the area between the treatment days after the onset of disease to the termination day is computed. Means for each group are determined and % inhibition from arthritis controls calculated by comparing values for treated and normal animals. Paw scores and histologic parameters (mean±SE) for each group are analyzed for differences using a Student's t-test with significance set at p 0.05. Percent inhibition of histologic parameters and AUC is calculated as [(mean disease control−mean normal)−(mean treated−mean normal)]/[[(mean disease control−mean normal)·(mean treated−mean normal)]·100.

MGBG was not efficacious in this model as a disease-modifying anti-rheumatic drug (DMARD), but did affect the early phase of paw swelling/inflammation. The protocols above may be varied according to methods known in the art.

In Vivo Murine MOG-EAE Multiple Sclerosis Model

An experimental murine model of multiple sclerosis employing a myelin oligodendrocyte glycoprotein (MOG) peptide to induce experimental autoimmune encephalomyelitis (EAE) was employed to determine the efficacy of MGBG in preventing and treating that disease. Because of its many similarities to MS, EAE is commonly used to study pathogenesis of autoimmunity, CNS inflammation, demyelination, cell trafficking, and tolerance induction. EAE is characterized by paralysis (in some models the paralysis is remitting-relapsing), CNS inflammation and demyelination. EAE is mediated primarily by dendritic cells, myelin-specific T cells (e.g. Th1 and Th17), and M1 macrophages. B cells may also play a role in some models of EAE. Body weight also tracks disease progression. EAE is induced in C57BL/6 mice by immunization with $MOG_{35-55}$ or $MOG_{1-125}$ in CFA emulsion followed by administration of pertussis toxin (PTX) in PBS. The emulsion provides antigen which initiates expansion and differentiation of MOG-specific autoimmune T cells. PTX enhances EAE development by providing additional adjuvant and facilitating entrance of autoimmune T cells into the CNS.

EAE induction. Chronic EAE develops in C57BL/6 mice after immunization with an emulsion of $MOG_{35-55}$/CFA or $MOG_{1-125}$/CFA followed by injection of pertussis toxin. This model is used to test the potential of compounds to prevent or mitigate EAE disease. It can be run with the compound dosed from the time of immunization (prophylactic treatment), or with the aim of reversing the course of disease and facilitating recovery by dosing the compound from the time of EAE onset (therapeutic treatment). The model uses female $C_{57}BL/6$ mice of age 10 to 14 weeks at the start of the study. Typically, EAE develops 8-18 days after immunization. EAE development is usually followed for 4 weeks (28 days) after immunization.

Stress reduces mouse susceptibility to EAE. Aside from any compound effects, the administration of treatment during the disease induction period (~0-10 days after immunization) postpones disease onset and reduces disease severity. This is due to the stress of compound administration and the effects of the vehicle on the mice. The more frequent the administration and the less tolerated the vehicle, the greater the impact on disease development. The stress of treatment and administration of vehicle has much less effect on disease development after clinical signs of EAE have appeared.

Prophylactic treatment. In prophylactic studies, treatment begins before disease onset, at the time of immunization and group assignment. Mice are assigned to treatment groups in a balanced manner to achieve groups with similar distributions of body weights. Prophylactic studies assess if treatment will affect the course of disease both before and after the first clinical signs of EAE. To compensate for the stress of treatment in prophylactic treatment studies and achieve the target disease severity, EAE may be induced with a higher dose of pertussis toxin than used in therapeutic studies. The dose of pertussis toxin is based on expected stress due to dosing (route, frequency, and formulation of vehicle).

In prophylactic studies, median time to disease onset is a sensitive measure of compound efficacy. Small changes in the immune response can result in postponed disease onset—suppression of T cell activation and proliferation, antigen presentation, differentiation into Th1 and/or Th17 cells will all result in postponed onset of EAE. Delayed onset of EAE accompanied with lower maximum severity indicates overall efficacy of treatment compared to the negative control group.

Some studies will show postponed EAE onset without other significant compound effects. In these cases the compound may affect an early pathway in immune response development, but eventually redundant processes compensate for the loss of the blocked pathway. Another possible explanation is that the drug was not able to maintain the blockade of the pathway for the duration of the study.

In other studies EAE is postponed but mice have higher end EAE scores than the vehicle-treated mice. Usually this is not caused by the compound making EAE worse but by the peak of disease in the compound-treated mice being postponed and coinciding with the period of recovery for the vehicle-treated mice.

When a compound is dosed prophylactically, one important readout of efficacy is reduction in maximum disease severity (mean maximum score, MMS). Reduced MMS indicates an overall reduction in EAE severity.

Scoring. Clinically, EAE progression is scored on a scale of 0 to 5, wherein each score represents the following clinical observations:
  0: no change in function;
  1—limp tail;
  2—limp tail and weakness of hind legs;
  3: one of the following:
    limp tail and complete paralysis of hind legs; or
    limp tail and complete paralysis of one front and one hind leg; or severe head tilting, walking along edges of cage, pushing against cage wall, and spinning when picked up by tail;

4—limp tail and complete hind leg and partial front leg paralysis;

5: one of the following:
  complete front/hind leg paralysis; or
  spontaneous rolling in cage; or
  death secondary to paralysis.

Course of EAE development in untreated mice. Individual mice will have somewhat differing courses of disease. Most mice show initial signs of EAE between 9 and 14 days after immunization. Once EAE starts, the peak of disease almost always occurs 3-4 days later. The maximum score continues for several days and then mice partially recover. In some mice, disease will stay at maximum severity until the end of the study. Less often, a mouse will stay at the peak severity for only one day and then start recovering. The extent of recovery largely depends on the maximum severity reached by the mouse. Most untreated or vehicle-treated mice will not fully recover, but their end score will usually be 0.5 to 1.5 points lower than their maximum score. About 25% of untreated or vehicle-treated mice show worsening EAE between 24 and 28 days after immunization, resembling a relapse. Spinal cords of these mice at the time of EAE worsening have a large number of inflammatory foci (≥7 foci per section), similar to histological findings at the time of EAE onset and peak, suggesting that these are true relapses with a new wave of inflammation in the spinal cords. When mice are followed for a longer period of time, disease slowly increases in severity, resembling the chronic progressive course of disease observed in human MS patients.

During the course of EAE, changes in body weight reflect disease severity. Mice often lose a small amount of weight on the day following immunization. This appears to be due to effects of the administered adjuvant and pertussis toxin. Mice then steadily increase their body weight until disease onset. On the day of EAE onset, mice consistently lose 1-2 g of their body weight (5-10% of body weight). The weight loss continues with the progression of EAE severity, with the loss reaching around 20% of their pre-onset body weight at the peak of disease. The weight loss is most likely due to both paralysis and reduced food intake as well as high production of pro-inflammatory cytokines such as TNF during the acute phase of inflammation. After the peak of disease is reached, mice slowly gain weight, even if their clinical score does not improve. This increase in weight may be due to down regulation of inflammation which results in lower levels of pro-inflammatory cytokines in blood. Untreated or vehicle-treated mice usually have around 90% of their pre-immunization body weight 28 days after immunization.

Histology. Typically, histological analysis is performed either at the end of the study (usually around 28 days after immunization) or at the time when the vehicle group reaches peak of disease (usually 14-18 days after immunization), and focuses on inflammatory foci, apoptosis, and demyelination, each of which is addressed below. Inflammation in EAE normally starts in the lumbar region of the spinal cord, spreading to the entire spinal cord by the peak of disease.

Apoptosis. Apoptotic cells are identified in H&E sections, and are usually not found during the first two days of disease development. They are found at the peak and during the chronic stage of EAE. The average number of apoptotic cells is usually between 2 and 4 per section. The apoptotic cells are neurons and their number correlates with disease stages. Apoptotic cells appear soon after disease onset, so at EAE onset there will be many inflammatory foci, but few apoptotic cells. Then, the number of apoptotic cells increases until the peak of disease, then remains elevated.

Inflammation. At onset of disease the number of inflammatory foci correlates strongly with disease severity. The number of foci increases somewhat until the peak of disease, when 6-15 inflammatory foci/section are typically found throughout the spinal cord. In the chronic stage of EAE (starting several days after the peak of disease), many inflammatory foci resolve, typically resulting in 3-4 inflammatory foci in each spinal cord section by approximately 28 days after immunization.

Because the largest numbers of inflammatory foci are present early in the course of disease, if histological analysis is performed at the end of the study, mice which have late EAE onset often have more inflammatory foci in their spinal cords than might be expected from their clinical score. For example, in a 28 day study a mouse with EAE onset on 27 days after immunization and an end clinical score of 2 will likely have more inflammatory foci than a mouse with EAE onset 9 days after immunization and an end score of 3.5. Similarly, a mouse which relapses shortly before the end of the study (relapse is defined as 1 or more points of increase in clinical score) will usually have more inflammatory foci at the end of the study than a mouse with stable chronic disease, even if the two have the same clinical score at the end of the study.

Inflammatory foci of approximately 20 cells were counted in each H&E stained section. When inflammatory infiltrates consisted of more than 20 cells, an estimate was made of how many foci of 20 cells were present.

Demyelination. Demyelination is usually not found during the first two days after disease onset, but is found at the peak of disease (4-5 days after EAE onset) and continues during the chronic phase of EAE. Demyelination scores do not change much between the peak and 28 days after immunization and usually average between 1.2 and 2.5. Demyelination is scored in both Luxol fast blue stained sections (LFB) and in H&E sections. In LFB sections, spinal cord white matter stains dark blue and demyelinated areas are a lighter blue color, and are associated with large vacuoles. In H&E stained sections disruption of normal structure with large vacuoles is indicative of demyelination.

The demyelination score represents an estimate of demyelinated area for each section as follows:
  0—no demyelination (less than 5% demyelinated area)
  1—5 to 20% demyelinated area
  2—20 to 40% demyelinated area
  3—40 to 60% demyelinated area
  4—60 to 80% demyelinated area
  5—80 to 100% demyelinated area For Luxol fast blue stained slides, the size of the demyelinated area was estimated based on less intense blue staining of myelin. For H&E stained sections, the demyelinated area was estimated by looking for interruption of normal structure—pallor and vacuolation consistent with edema and demyelination, and dilated axons.

Statistical analysis. Unless otherwise noted, statistical analysis was performed as follows: disease incidence compared using chi-square test; mean day of EAE onset, change in body weight, and number of apoptotic cells compared using 2-tailed Student's t-test; median day of EAE onset compared using Wilcoxon's survival test; mean maximum score (MMS), end score, and demyelination scores (LFB and H&E) compared using Wilcoxon's non-parametric test.

First MOG EAE Protocol.

Materials and Methods. Ten week old female C57BL/6 mice weighing 18-23 g (Taconic Farms) were divided into four groups: mock immunized (n=3) and three MOG-immunized groups receiving MGBG at 30 mpk BID (as the di-HCl monohydrate with a correction factor of 1.49), fingolimod (FTY720) at 3 mpk QD with a second mock vehicle dose, or 0.9% saline vehicle BID (n=12 each). $MOG_{35-55}$ peptide was administered by subcutaneous injection at two sites in the back with the emulsion component (containing $MOG_{35-55}$ for test article or positive control, or PBS for negative control) of Hooke Kit™ $MOG_{35-55}$/CFA Emulsion PTX, catalog number EK-2110 (Hooke Laboratories, Lawrence Mass.). One site of injection was in the area of upper back, approximately 1 cm caudal of the neck line. The second site was in the area of lower back, approximately 2 cm cranial of the base of the tail. The injection volume was 0.1 mL at each site. Within 2 hours of the injection of emulsion, and then again 24 hours after the injection of emulsion, the pertussis toxin component of the kit (diluted with PBS to achieve 176 ng/dose for the first injection and 165 ng/dose for the second injection) was administered intraperitoneally. The volume of each injection was 0.1 mL.

Inoculated, untreated mice develop EAE 8-14 days after immunization with $MOG_{35-55}$/CFA and stay chronically paralyzed for the 28-day duration of the experiment. Clinical scores, body weights, and histopathology of spinal cord (e.g., demyelination, inflammatory infiltrates, and/or apoptosis) may be measured and recorded as set forth above.

Results. Clinical scores, given as mean score+/−the standard error of the mean (SEM), are shown in FIG. 1. As can be seen in FIG. 1, vehicle-treated animals developed EAE clinical signs beginning on day 10 as expected, with mean clinical signs increasing until day 16, when scores surpassed 2 and thereafter remained between 2 and 3. Fingolimod was the most efficacious at the high dose tested, yielding mean clinical scores of 0 throughout the experiment, a level almost indistinguishable from the mock-immunized group. MGBG also prevented onset and progression of EAE, with the first clinical signs becoming evident on day 15 and slowly increasing thereafter to a level still below 1 on day 21, and remaining below 1 for the duration of the experiment. Results demonstrate that MGBG, like fingolimod, is efficacious in preventing and treating neurological symptoms of MS in an accepted model of the disease.

Figure 2:
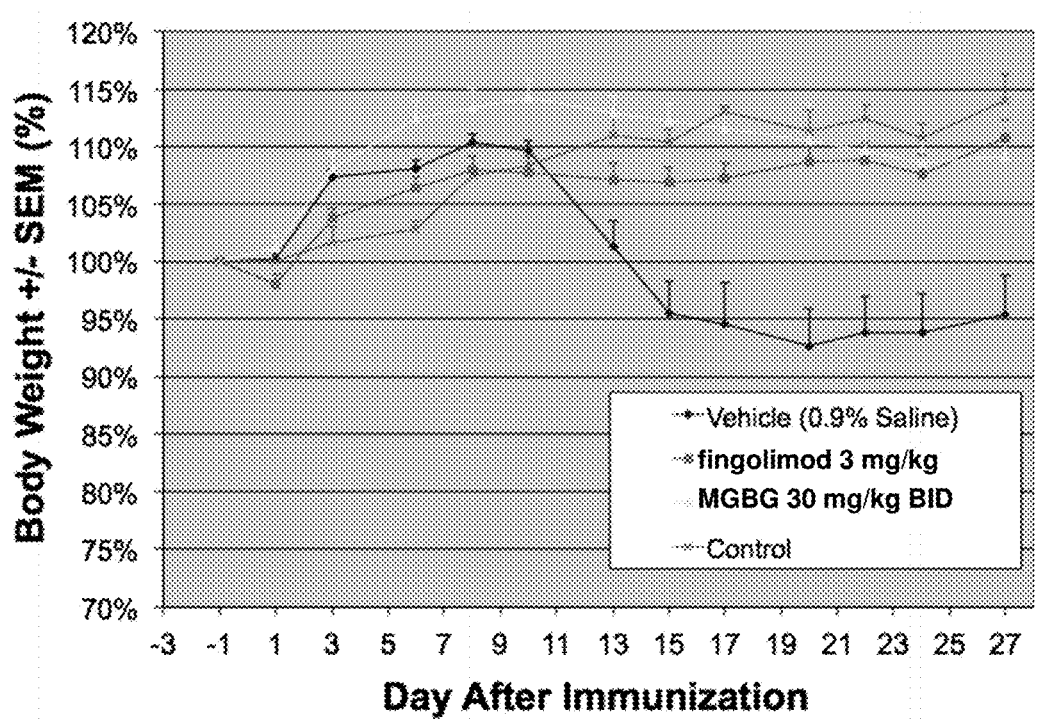
FIG. 2 shows the mean percentage change in body weight (relative to study start) of subjects in the first 28-day MOG EAE model, wherein test subjects were dosed with vehicle, 30 mpk MGBG (twice-daily), or 3 mpk fingolimod (once-daily), and compared with mock-immunized subjects.

Additionally, as shown in FIG. 2, treatment with either fingolimod or MGBG prevented loss of body weight in the EAE model. Results in FIG. 2, given as the mean percent change from baseline (study start)+/−SEM, show that all groups continued to gain weight until approximately day 8 when body weights of approximately 107-113% were seen. Thereafter, the vehicle-treated group began to lose weight, with rapid loss to 95% on day 15, and reaching a low of about 93% on day 20 before recovering slightly by the end of the study to about 95%. The sham-immunized and MGBG- and fingolimod-treated groups, generally speaking, each retained weight gained throughout the study, hovering between about 108% and about 114%. Fingolimod and vehicle groups demonstrated a slight trend of gradual and continued weight gain over the course of the study. MGBG-treated subjects showed the most substantial gains initially, nearing 115% on day 11, but showed gradual loss to about 108% on day 24, before rising slightly again. These results further demonstrate that MGBG, like fingolimod, is efficacious in preventing and treating symptoms of MS.

Histopathology. On day 28 (end of the study) all mice were sacrificed for histological analysis and perfused with PBS, and spines were collected in 10% buffered formalin. For each mouse, 3 Luxol fast blue stained sections and 3 H&E sections, from lumbar, thoracic, and cervical spinal cord, were prepared and analyzed by a pathologist blinded to the experimental groups and all clinical readouts. The number of inflammatory foci, apoptotic cells, and demyelinated regions in each of the three H&E sections was determined.

Figure 3:
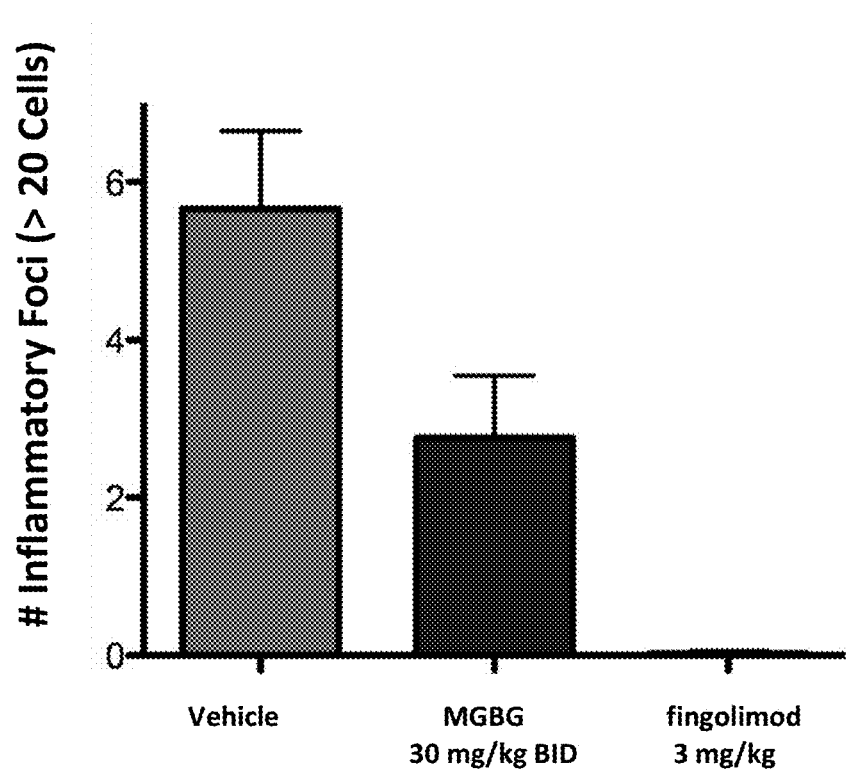
FIG. 3 shows the reduction in spinal cord inflammation as measured by the number of inflammatory foci in spinal cord histopathological samples, from the 28-day MOG EAE model, wherein test subjects were dosed with vehicle, 30 mpk MGBG (twice-daily), or 3 mpk fingolimod (once-daily), and compared with mock-immunized subjects.
Figure 4:
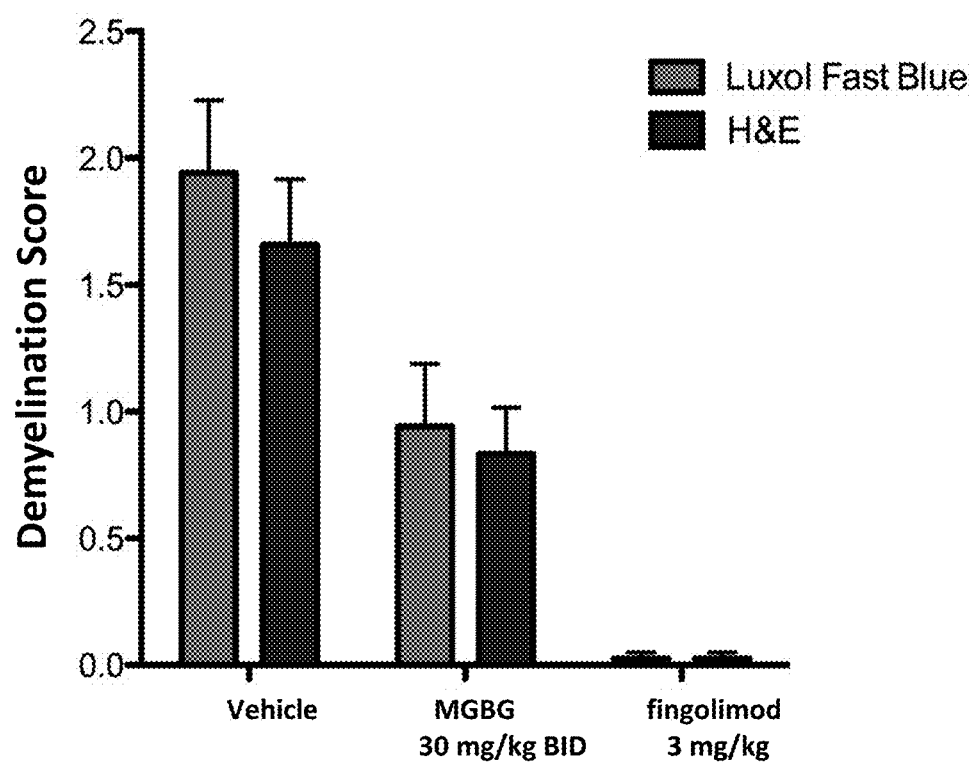
FIG. 4 shows reduction in spinal cord demyelination in histopathological samples from the 28-day MOG EAE model, wherein test subjects were dosed with vehicle, 30 mpk MGBG (twice-daily), or 3 mpk fingolimod (once-daily), and compared with mock-immunized subjects.
Figure 5:
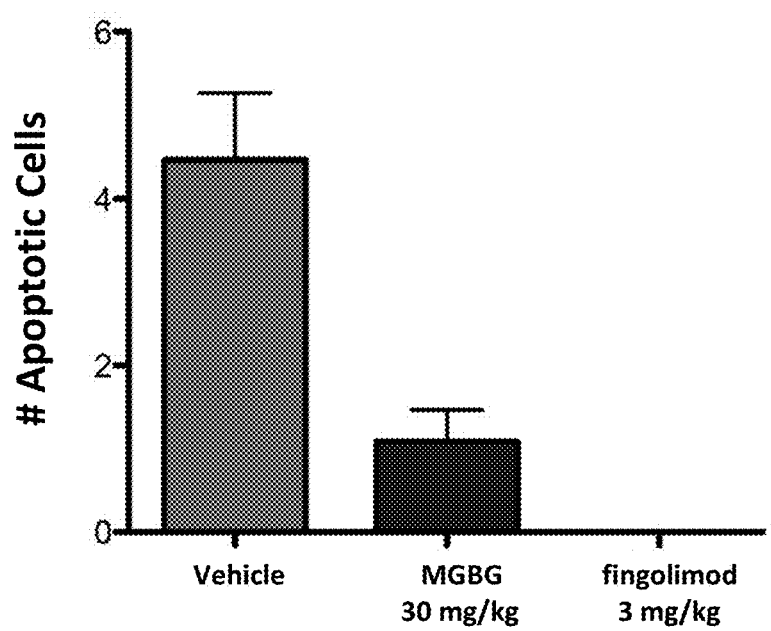
FIG. 5 shows reduction in cellular apoptosis in spinal cord histopathological samples from the 28-day MOG EAE model, wherein test subjects were dosed with vehicle, 30 mpk MGBG (twice-daily), or 3 mpk fingolimod (once-daily), and compared with mock-immunized subjects.
Figure 6:
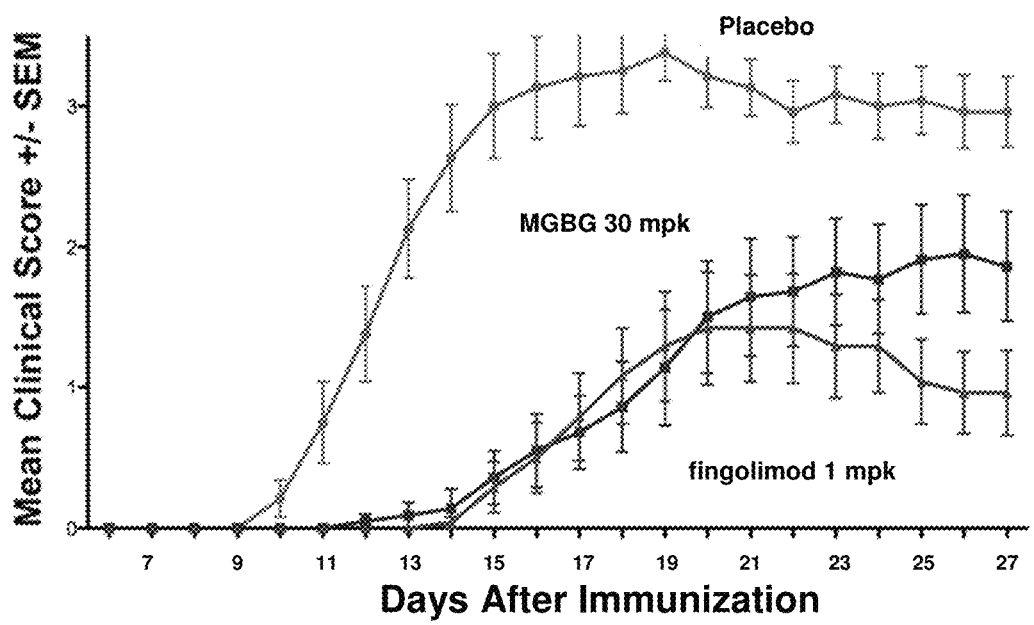
FIG. 6 shows the mean clinical scores of subjects in the second 28-day murine MOG EAE model, wherein test subjects were dosed with vehicle, 30 mpk MGBG (twice-daily), or 1 mpk fingolimod (once-daily), and compared with mock-immunized subjects; MGBG suppressed EAE comparably to 1 mpk fingolimod.
Figure 7:
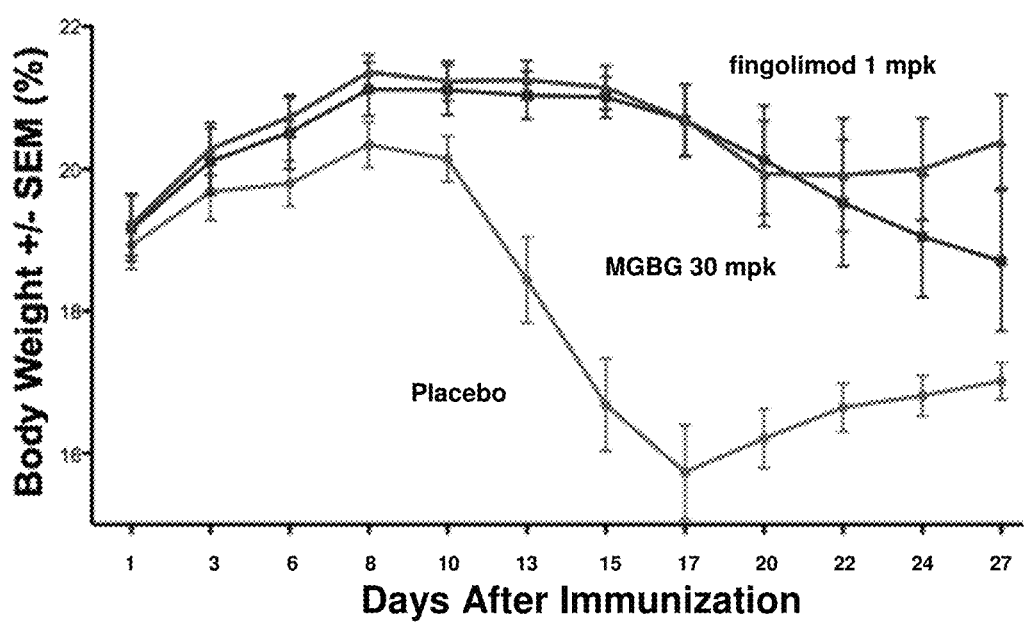
FIG. 7 shows the mean percentage change in body weight (relative to study start) of subjects in the second 28-day MOG EAE model, wherein test subjects were dosed with vehicle, 30 mpk MGBG (twice-daily), or 1 mpk fingolimod (once-daily), and compared with mock-immunized subjects.
Figure 8:
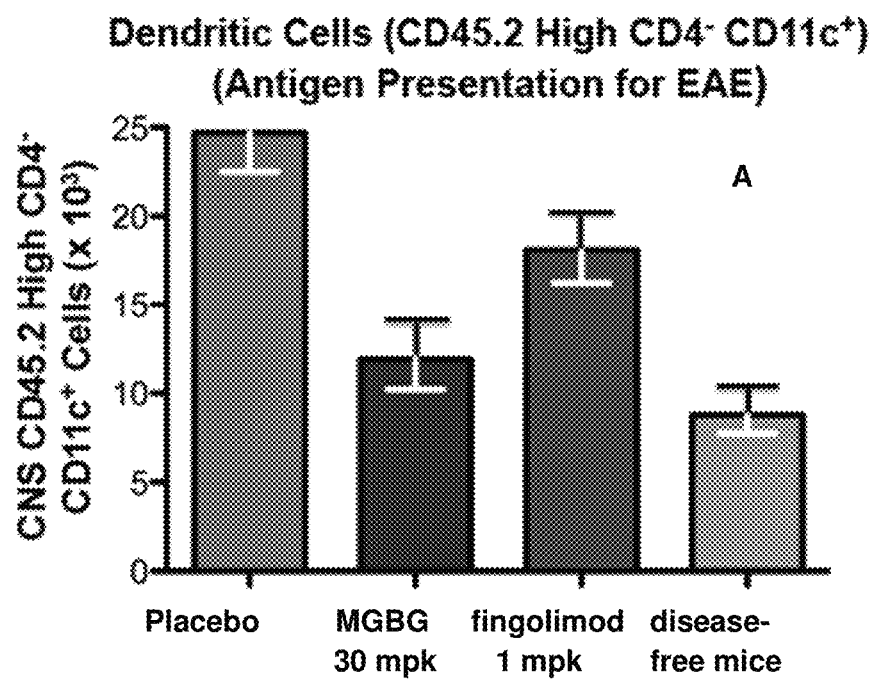
FIG. 8 shows that MGBG, but not fingolimod, reduces CNS A) CD11c+ dendritic cells associated with antigen presentation and B) IL12+ dendritic cells associated with promotion of the Th1 response.
Figure 8:
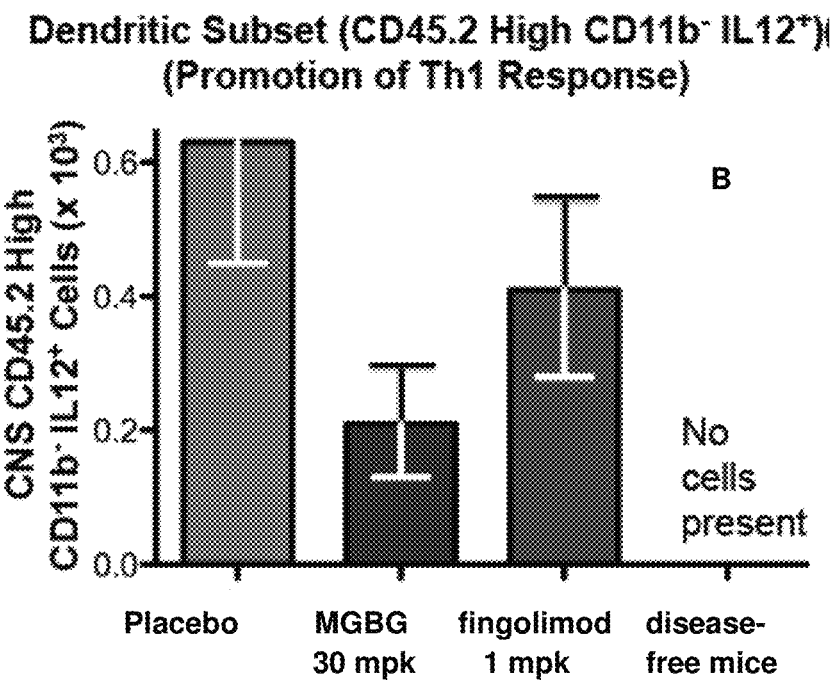
Figure 9:
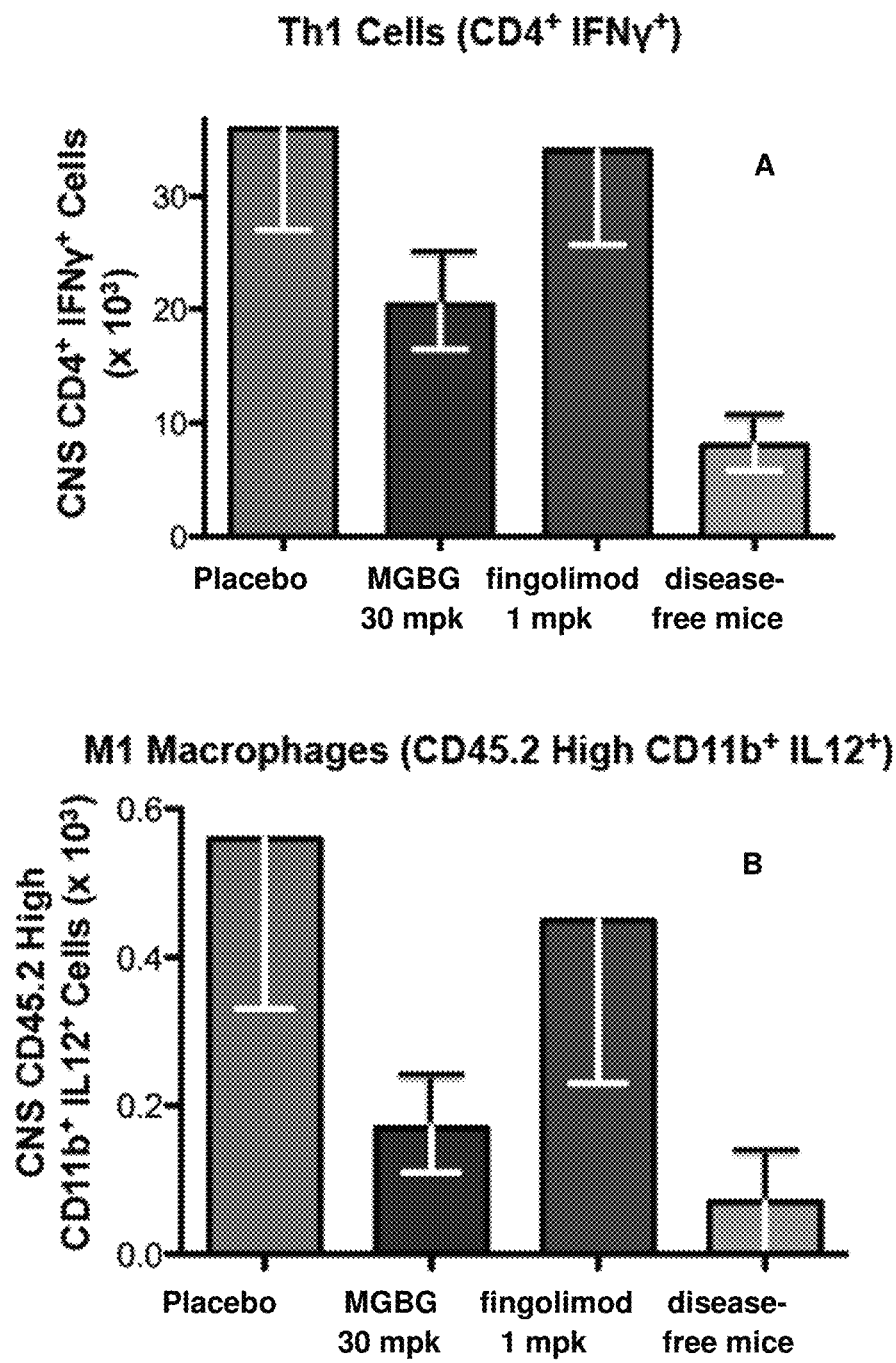
FIG. 9 shows that MGBG, but not fingolimod, reduces A) Th1 and B) M1 macrophages.
Figure 10:
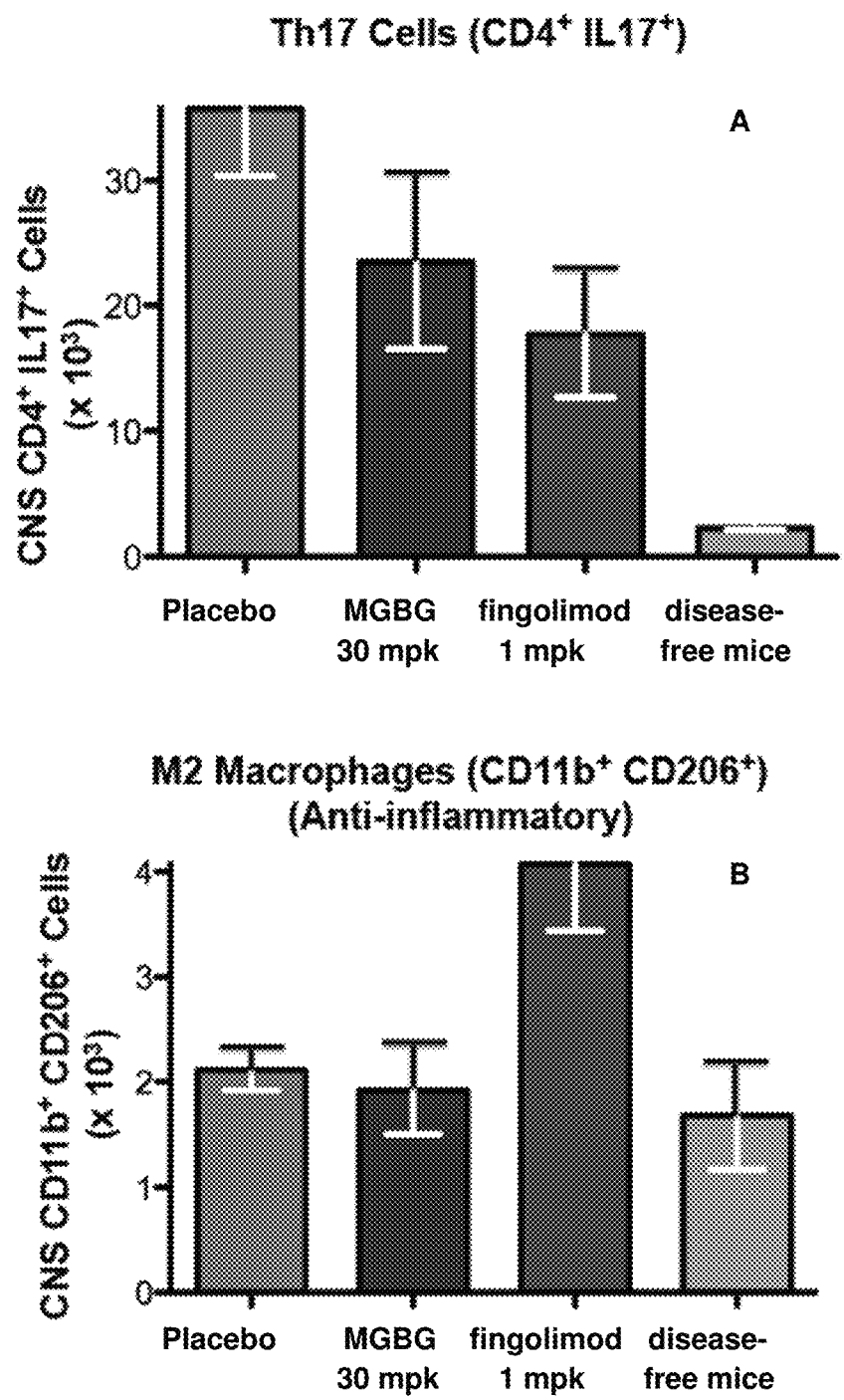
FIG. 10 shows that fingolimod preferentially A) suppresses Th17 and B) increases M2 macrophages; thus, MGBG and fingolimod have distinct, but therapeutically complementary activities in MS.

Histopathological results are shown in FIGS. 3-5, which confirm that MGBG, like fingolimod, reduces histopathological signs of MS such as neuroinflammation, demyelination (via both stains), and apoptosis. Additionally, the negative control group (data not shown) demonstrated scores of zero.

Second MOG EAE Protocol.

A second EAE experiment was run substantially as disclosed above, except that fingolimod was dosed at 1 mpk QD, and the pertussis toxin was administered at 165 ng/dose for both injections.

Results. EAE was more severe in this study than in the typical study conducted according to this protocol, and more severe than in the previous study. All mice in the vehicle group developed severe EAE. Disease development in the fingolimod-treated group was not as strongly suppressed as in the previous study or as in the typical study. This is not surprising, given that more severe disease is generally more difficult to suppress. Mice in the MGBG-treated group developed substantially reduced disease compared to that of the vehicle group, displaying comparable efficacy to that of fingolimod.

Results are given in FIGS. 6-10. Consistent with the previous study, MGBG was efficacious at postponing disease onset and reducing EAE severity.

Fluorescence-Activated Cell Sorting. In addition to clinical scoring, flow cytometric analysis was performed on CNS-infiltrating cells from 6 mice in each of the vehicle-, fingolimod- and MGBG-treated groups, as well as in all three mice from the mock-immunized (disease-free) group.

On Day 28, the brain and spinal cord tissue (from 6 of 12 mice from each of the MOG-immunized groups; and from all 3 mice from the mock-immunized group) in the second MOG EAE study were pooled and infiltrating cells were isolated by Percoll gradient. After isolating infiltrating cells from each mouse separately, cells were placed in culture with phorbol myristate acetate (PMA, 50 ng/mL), ionomycin (0.5 μg/mL) and brefeldin (1 μg/mL) and incubated for 4-5 hours. The cells were then washed and stained for flow cytometric analysis, as specified below. The following analyses were performed (Becton Dickinson FACScan):

Anti-CD4-Cy-5/anti-IL-17A-PE/anti-IFNγ-FITC (Th1/Th17 cells)

Anti-CD4-Cy-5/anti-CD11c-PE/anti-CD45.2-FITC (infiltrating dendritic cells)

Anti-CD11b-Cy-5/anti-IL-12-PE/anti-CD45.2-FITC (M1 macrophages)

Anti-CD11b-Cy-5/anti-CD206-PE/anti-IL-10-FITC (M2 macrophages)

The number of cells positive for relevant stains and stain combinations was computed both as a percentage of the analyzed cells and as the average number of cells per mouse for each group.

TABLE 8

| | Roles of CNS-infiltrating cells and cytokines |
|---|---|
| CD4+ | These cells trigger EAE. Mice with EAE are known to have more CNS-infiltrating CD4+ cells than disease-free mice, and the number of infiltrating CD4+ cells in the CNS often correlates with disease severity |
| IL-17A | A pro-inflammatory cytokine produced by Th-17 cells. Th-17 cells are believed to play a major pathogenic role in EAE development. |
| CD4+IL-17A+IFNγ+ | IFNγ is the main cytokine produced by Th-1 cells. While the role of IFNγ in EAE is not clear, it is believed to be highly pathogenic in EAE. |
| CD4+IFNγ+ | IFNγ is the main cytokine produced by Th-1 cells. While the role of IFNγ in EAE is not clear, it is believed that Th-1 cells, which produce IFNγ play a pathogenic role in EAE, especially during the chronic phase of disease. |
| Dendritic cells (DC) CD4−CD11c+ CD45.2 high | Play a critical role in presenting antigen to T cells and their activation. Therefore they play a critical role in controlling immune processes. |
| CD11b (integrin alpha M) | Part of integrin heterodimer (Mac-1) and is expressed primarily on macrophages (and microglia cells in the CNS) and other cells of the innate immune system (NK cells, granulocytes, some dendritic cells). Most of these cells are believed to play a pathogenic role in EAE development. |
| CD206 | A mannose receptor, which is up-regulated in M2 macrophages (which are believed to suppress Th-1 and Th-17 type T cell responses). This is usually measured on macrophages (CD11b+). |
| Arginase-1 | The final enzyme in the urea cycle. It converts L-arginine into L-ornithine and urea. It is expressed in cytoplasm and it competes with nitric oxide synthase for L-arginine. Arginase-1 is expressed in alternatively-activated macrophages (M2 type macrophages), and plays an important role in suppressing T cell functions. This is usually measured on macrophages (CD11b+). |
| CD11c | The main marker of dendritic cells. F4/80 is one of the markers of mature macrophages. Therefore CD11c+F4/80-cells are mostly dendritic cells. |
| IL-10 | An anti-inflammatory cytokine produced primarily by monocytes, macrophages (M2-type), Treg and Th-2 cells. |
| IL-12 | A cytokine produced by dendritic cells and macrophages. It is essential for Th-1 cell differentiation and is believed to play an important role in development of autoimmune diseases. |

Mice treated with MGBG had a significantly reduced relative and absolute number of CNS infiltrating dendritic cells (DCs, CD45RBhigh, CD11c$^+$) and a significantly reduced number of IL-12-producing cells among CNS-infiltrating CD11b-cells. Results are given in the tables below, where * indicates p<0.05 and ** indicates p<0.1. Tables 9 and 11 show results in terms of percentages of total cells, and Tables 10 and 12 shows results in terms of raw numbers of cells ($10^3$).

TABLE 9

| Treatment | Total # of CNS-infiltrating cells ($10^3$) | % of CD4+ cells | % IL-17A+ cells of CD4+ cells | % CD4+ IFNγ+ cells | % CD11c+ of CD45.2 high CD4− cells |
|---|---|---|---|---|---|
| vehicle (0.9% saline) | 723.33 +/− 258.43 | 34.32 +/− 5.36 | 14.77 +/− 2.14 | 15.75 +/− 6.98 | 12.05 +/− 4.75 |
| fingolimod, 1 mg/kg QD | 620.00 +/− 190.16 | 17.69 +/− 11.08* | 15.22 +/− 2.06 | 30.89 +/− 5.13* | 11.39 +/− 5.36 |
| MGBG, 30 mg/kg BID | 500.00 +/− 142.55** | 28.50 +/− 12.20 | 15.24 +/− 6.02 | 15.85 +/− 6.48 | 7.21 +/− 1.89* |
| Negative EAE control | 286.67 +/− 41.63* | 10.87 +/− 3.29* | 7.65 +/− 1.31* | 25.82 +/− 9.71 | 11.87 +/− 5.26 |

TABLE 10

| Treatment | Total # of CNS-infiltrating cells (10³) | CD4+ cells | CD4+ IL-17A+ cells | CD4+ IFNy+ cells | CD45.2 high CD4– CD11c+ cells |
|---|---|---|---|---|---|
| vehicle (0.9% saline) | 723.33 +/– 258.43 | 245.68 +/– 88.17 | 35.71 +/– 11.94 | 35.96 +/– 19.90 | 24.70 +/– 4.88 |
| fingolimod, 1 mg/kg QD | 620.00 +/– 190.16 | 117.89 +/– 76.59* | 17.67 +/– 12.15* | 34.06 +/– 20.34 | 18.10 +/– 4.64* |
| MGBG, 30 mg/kg BID | 500.00 +/– 142.55** | 152.11 +/– 82.13** | 23.55 +/– 17.12 | 20.40 +/– 9.59 | 11.90 +/– 4.14* |
| Negative EAE control | 286.67 +/– 41.63* | 30.26 +/– 4.25* | 2.28 +/– 0.21* | 8.03 +/– 3.82** | 8.87 +/– 1.79* |

TABLE 11

| Treatment | Total # of CNS-infiltrating cells (10^3) | % of CD11b+ cells | % CD206+ of CD11b+ cells | % IL10+ of CD11b+ cells | # of IL12+ cells (10^3) | % IL12+ of CD45.2 high CD11b– cells |
|---|---|---|---|---|---|---|
| vehicle (0.9% saline) | 723.33 +/– 258.43 | 21.04 +/– 3.83 | 1.48 +/– 0.21 | 3.31 +/– 1.42 | 1.89 +/– 1.15 | 0.14 +/– 0.08 |
| fingolimod, 1 mg/kg QD | 620.00 +/– 190.16 | 38.50 +/– 5.92 * | 1.81 +/– 0.65 | 1.65 +/– 0.70 * | 1.86 +/– 1.04 | 0.16 +/– 0.12 |
| MGBG, 30 mg/kg BID | 500.00 +/– 142.55 ** | 27.86 +/– 4.50 * | 1.39 +/– 0.65 | 2.37 +/– 1.19 | 0.89 +/– 0.41 ** | 0.06 +/– 0.06 ** |
| Negative EAE control | 286.67 +/– 41.63 * | 29.94 +/– 2.34 * | 2.07 +/– 1.27 | 1.36 +/– 0.82 ** | 0.20 +/– 0.19 * | 0.00 +/– 0.00 * |

TABLE 12

| Treatment | Total # of CNS-infiltrating cells (10^3) | CD11b+ cells | CD11b+ CD206+ cells | CD11b+ IL10+ cells | IL12+ cells | CD45.2 high CD11b– IL12+ cells |
|---|---|---|---|---|---|---|
| vehicle (0.9% saline) | 723.33 +/– 258.43 | 145.80 +/– 37.87 | 2.11 +/– 0.43 | 4.46 +/– 1.01 | 1.89 +/– 1.15 | 0.63 +/– 0.40 |
| fingolimod, 1 mg/kg QD | 620.00 +/– 190.16 | 244.75 +/– 95.47 * | 4.07 +/– 1.54 * | 4.22 +/– 2.64 | 1.86 +/– 1.04 | 0.41 +/– 0.33 |
| MGBG, 30 mg/kg BID | 500.00 +/– 142.55 ** | 137.88 +/– 38.51 | 1.92 +/– 1.03 | 3.37 +/– 2.14 | 0.89 +/– 0.41 ** | 0.21 +/– 0.20 * |
| Negative EAE control | 286.67 +/– 41.63 * | 85.54 +/– 11.29 * | 1.68 +/– 0.89 | 1.22 +/– 0.87 | 0.20 +/– 0.19 * | 0.00 +/– 0.00 * |

Third MOG EAE Protocol.

A third EAE experiment was run substantially as disclosed above, except that fingolimod was dosed at 0.1 mpk QD (which corresponds well with the typical human dose or 0.5 mg/day, scaling for body surface area), and an additional group combining MGBG 30 mpk and fingolimod 0.1 mpk was added. Here as well, the pertussis toxin was administered at 165 ng/dose for both injections.

Results. Both fingolimod and MGBG separately showed comparable efficacy in reducing disease severity and postponing disease onset at the doses tested. There were also significantly fewer inflammatory foci and significantly less demyelination in treated mice compared to the vehicle-treated mice. Importantly, no mice in the fingolimod/MGBG combination group developed EAE, and all other clinical readouts (e.g. body weights) were significantly improved (no signs of EAE) compared to the vehicle group—no disease was detectable in these mice.

Collectively, these results indicate that the combination of fingolimod and MGBG was highly efficacious at preventing development of EAE. In addition, mice which received the combination treatment had significantly improved clinical and histological readouts compared to the mice receiving either fingolimod or MGBG alone. The combination appeared to prevent disease from developing.

Other combinations of agents could be readily tested in a protocol similar to the above. For example, interferon beta-1a, interferon beta-1b, glatiramer acetate, mitoxantrone, natalizumab, laquinimod, dimethyl fumarate (tecfidera), and teriflunomide could each be tested in combination with MGBG. Other SAMDC inhibitors could be tested as well. It is expected that these combinations would be similarly efficacious. Without wishing to be bound by theory, the combination of MGBG, which appears to affect early events in the development of MS such as antigen presentation and the infiltration of dendritic cells into the CNS, should be efficacious in combination with other drugs, for example, those like fingolimod which act at a different (in certain embodiments, later) stage in the development of an episode or flare-up of multiple sclerosis, or another demyelinating disease.

Fourth MOG EAE Protocol.

A fourth EAE experiment was run similarly to the above, but was designed to examine the effect of MGBG on cell populations during onset and peak disease. In this protocol, there were 3 experimental groups with 20 mice/group and 1 mock-immunized group with 8 mice. Fingolimod was dosed at 1 mpk QD, MGBG at 30 mpk BID, and the pertussis toxin was administered at 165 ng/dose for both injections. Flow cytometric analysis was performed on CNS-infiltrating cells from 16 mice from each of the vehicle-, fingolimod- and MGBG-treated groups, as well as from all mice in the mock-immunized group. Half of the analyzed mice from each group were collected at the time of EAE onset in the vehicle group and half were collected at the time of EAE peak in the vehicle group. Mouse termination was over eight separate days, because individual mouse in the vehicle group reached EAE onset and EAE peak on different days. Eight (8) of the mice in the vehicle group were sacrificed at each time-point. For each of these mice, a matching mouse from each of Groups 2 and 3 was sacrificed on the same day. For each two (2) of these vehicle group mice, a matching mouse from Group 4 was sacrificed. When selecting matching mice from other groups for termination, the mouse with the highest EAE score was chosen. If no mouse in the group had signs of EAE, a mouse was chosen at random.

Results. CNS infiltration by proinflammatory cells was reduced in MGBG-treated mice, consistent with the clinical finding that MGBG reduces EAE development. Multiple proinflammatory cell populations were reduced in the CNS of MGBG-treated mice. Interestingly, the proportion and number of infiltrating dendritic cells was reduced in MGBG-treated mice more than in fingolimod-treated mice, and some of the differences were statistically significant. These results are consistent with previous studies, and suggest that MGBG selectively targets dendritic cells. In addition, the reduction in the number of IL-12 producing cells supports the notion that MGBG affects development of Th-1 type responses.

Results are given in the tables below, where * indicates $p<0.05$ and ** indicates $p<0.1$. Table 13 shows results in terms of percentages of total cells, and Table 14 shows results in terms of raw numbers of cells ($10^3$).

TABLE 13

| | Onset % cells unless otherwise indicated | | | | Peak % cells unless otherwise indicated | | | |
| --- | --- | --- | --- | --- | --- | --- | --- | --- |
| | vehicle | fingolimod | MGBG | (−) control | vehicle | fingolimod | MGBG | (−) control |
| Total # of cells ($10^3$) | 655.00 +/− 321.11 | 383.75 +/− 144.12* | 316.25 +/− 107.70* | 373.33 +/− 60.28 | 1032.50 +/− 320.35 | 343.75 +/− 75.077* | 346.25 +/− 82.10* | 387.50 +/− 97.43* |
| CD4+ | 27.27 +/− 4.42 | 5.35 +/− 1.21* | 10.42 +/− 3.09* | 8.77 +/− 2.79* | 29.42 +/− 4.50 | 5.82 +/− 1.29* | 13.40 +/− 5.16* | 7.40 +/− 2.79* |
| CD4+ IL-17A+ | 33.19 +/− 8.03 | 12.22 +/− 5.56* | 18.39 +/− 7.30* | 17.19 +/− 6.00* | 23.50 +/− 4.78 | 17.25 +/− 5.27* | 24.18 +/− 8.23 | 11.93 +/− 4.19* |
| CD4+ IL-17A+ IFNγ+ | 8.26 +/− 2.03 | 2.60 +/− 1.90* | 4.14 +/− 2.75* | 1.84 +/− 0.76* | 14.37 +/− 2.69 | 4.82 +/− 2.54* | 5.45 +/− 3.45* | 2.20 +/− 0.24 |
| CD4+ IFNγ+ | 12.34 +/− 3.69 | 15.16 +/− 3.37 | 9.57 +/− 3.73 | 12.33 +/− 2.40 | 20.01 +/− 6.51 | 17.15 +/− 3.77 | 9.37 +/− 1.87* | 15.19 +/− 4.15 |
| CD4− CD11c+ CD45.2 high | 6.47 +/− 1.44 | 5.42 +/− 0.95 | 3.68 +/− 1.39* | 4.98 +/− 1.66 | 7.36 +/− 2.36 | 5.41 +/− 1.74** | 4.39 +/− 2.07* | 4.64 +/− 0.86** |
| CD11b+ | 56.59 +/− 2.51 | 40.94 +/− 13.39* | 37.90 +/− 9.29* | 39.66 +/− 7.56* | 53.43 +/− 2.86 | 45.08 +/− 8.47* | 53.95 +/− 12.09 | 36.11 +/− 12.31* |
| CD11b+ CD206+ | 10.62 +/− 1.67 | 5.37 +/− 3.97* | 5.16 +/− 0.72* | 4.93 +/− 2.15* | 17.17 +/− 1.20 | 8.15 +/− 4.50* | 8.87 +/− 3.99* | 4.77 +/− 1.12* |
| CD11b+ Arginase-1+ | 3.28 +/− 0.94 | 3.85 +/− 1.92 | 3.08 +/− 1.30 | 3.81 +/− 0.54 | 7.62 +/− 1.35 | 2.31 +/− 0.98* | 2.54 +/− 0.98* | 1.57 +/− 0.30* |
| CD206+ Arginase-1+ | 1.04 +/− 0.60 | 0.38 +/− 0.21* | 0.51 +/− 0.24* | 0.35 +/− 0.11** | 2.75 +/− 0.36 | 0.49 +/− 0.34* | 0.86 +/− 0.59* | 0.16 +/− 0.09* |
| CD11c+ F4/80− | 5.59 +/− 1.01 | 3.40 +/− 1.53* | 2.85 +/− 1.35* | 2.75 +/− 0.48* | 3.71 +/− 1.15 | 4.22 +/− 1.21 | 4.66 +/− 2.54 | 2.44 +/− 0.69** |
| IL-12+ | 0.86 +/− 0.36 | 0.83 +/− 0.60 | 0.73 +/− 0.48 | 0.40 +/− 0.29** | 1.01 +/− 0.28 | 0.59 +/− 0.43* | 0.62 +/− 0.38* | 0.33 +/− 0.18* |

TABLE 14

| | Onset # cells ($10^3$) | | | | Peak # cells ($10^3$) | | | |
| --- | --- | --- | --- | --- | --- | --- | --- | --- |
| | vehicle | fingolimod | MGBG | (−) control | vehicle | fingolimod | MGBG | (−) control |
| Total # of cells ($10^3$) | 655.00 +/− 321.11 | 383.75 +/− 144.12* | 316.25 +/− 107.70* | 373.33 +/− 60.28 | 1032.50 +/− 320.35 | 343.75 +/− 75.77* | 346.25 +/− 82.10* | 387.50 +/− 97.43* |

TABLE 14-continued

|  | Onset # cells (10³) | | | | Peak # cells (10³) | | | |
| --- | --- | --- | --- | --- | --- | --- | --- | --- |
|  | vehicle | fingolimod | MGBG | (−) control | vehicle | fingolimod | MGBG | (−) control |
| CD4+ | 187.68 +/− 109.88 | 20.14 +/− 6.78* | 32.66 +/− 13.83* | 33.38 +/− 15.06* | 310.86 +/− 119.64* | 20.58 +/− 8.42* | 47.51 +/− 21.25* | 28.47 +/− 12.01* |
| CD4+ IL-17A+ | 102.99 +/− 12.16 | 2.19 +/− 0.46* | 6.52 +/− 4.74* | 6.34 +/− 5.09* | 76.35 +/− 39.56 | 3.82 +/− 2.54* | 12.44 +/− 7.83* | 3.74 +/− 2.46* |
| CD4+ IL-17A+ IFNy+ | 15.70 +/− 11.50 | 0.50 +/− 0.38* | 1.56 +/− 1.52* | 0.63 +/− 0.36** | 45.90 +/− 21.79 | 1.05 +/− 0.88* | 3.01 +/− 2.54* | 0.61 +/− 0.22* |
| CD4+ IFNy+ | 23.71 +/− 15.97 | 3.09 +/− 1.35* | 3.19 +/− 1.73* | 4.08 +/− 1.78** | 59.72 +/− 24.57 | 3.64 +/− 2.06* | 4.57 +/− 2.52* | 4.10 +/− 1.68* |
| CD4− CD11c+ CD45.2 high | 21.05 +/− 11.16 | 4.86 +/− 6.52* | 3.24 +/− 2.69* | 4.16 +/− 1.56* | 40.72 +/− 25.17 | 5.41 +/− 5.39* | 7.23 +/− 5.80* | 3.59 +/− 0.87* |
| CD11b+ | 369.52 +/− 182.73 | 156.62 +/− 90.68* | 122.50 +/− 56.93* | 150.98 +/− 52.07** | 549.02 +/− 168.79 | 158.88 +/− 62.33* | 188.13 +/− 59.60* | 135.31 +/− 37.49* |
| CD11b+ CD206+ | 39.32 +/− 19.97 | 6.92 +/− 2.92* | 6.26 +/− 2.78* | 7.89 +/− 5.84* | 94.45 +/− 31.09 | 14.36 +/− 14.30* | 17.89 +/− 10.67* | 6.61 +/− 2.77* |
| CD11b+ Arginase-1+ | 12.29 +/− 7.40 | 5.88 +/− 3.43 | 3.38 +/− 1.29* | 5.90 +/− 2.59 | 40.67 +/− 10.61 | 3.81 +/− 2.23* | 4.92 +/− 2.76* | 2.20 +/− 0.90* |
| CD206+ Arginase-1+ | 7.13 +/− 5.62 | 1.34 +/− 0.67* | 1.59 +/− 0.88* | 1.35 +/− 0.62 | 27.66 +/− 7.30 | 1.81 +/− 1.58 | 3.14 +/− 2.33 | 0.60 +/− 0.33 |
| CD11c+ F4/80− IL-12+ | 35.93 +/− 16.78 | 14.03 +/− 12.69* | 8.93 +/− 5.06* | 10.23 +/− 2.35* | 39.18 +/− 19.87 | 14.93 +/− 7.32 | 16.21 +/− 9.38 | 8.95 +/− 1.02 |
|  | 5.09 +/− 2.88 | 2.93 +/− 2.06 | 2.33 +/− 1.82* | 1.60 +/− 1.37* | 10.78 +/− 5.36 | 1.93 +/− 1.32 | 2.21 +/− 1.52 | 1.36 +/− 1.00 |

Table 15 below illustrates the effects seen in a subset of animals which did not develop disease at the time when vehicle-treated animals were at the peak of disease. MGBG, but not fingolimod, reduced the number of dendritic cells. This suggests that MGBG (and more broadly, a SAMDC inhibitor having an effect on dendritic cell antigen presentation and CNS infiltration) may be important component in preventing or reducing the severity of EAE and MS, and/or their progression and associated symptoms, such as demyelination.

TABLE 15

| Group | CD11c+ of CD4− CD45.2+ high cells In Peak of Disease in Animals Without EAE Disease |
| --- | --- |
| Fingolimod | 5.41 +/− 0.62 |
| MGBG | 2.93 +/− 0.37 |
| (−) Control | 4.64 +/− 0.5 |

Additional In Vivo Models of Therapeutic Efficacy

The following models, presented by way of example, may be used to evaluate compounds disclosed herein for efficacy in the treatment of a number of diseases and indications. It is within the capacity of one skilled in the art to modify these models to suit the needs of the study. Additionally, those skilled in the art will be familiar with additional models of disease which may be employed. It is expected that MGBG, as well as other polyamine analogs and polyamine biosynthesis inhibitors and compounds disclosed herein, will be efficacious in these models.

Neuropathy and Neuropathic Pain Models

Bennett Model of Neuropathic Pain:

A peripheral mononeuropathy is produced in adult rats by placing loosely constrictive ligatures around the common sciatic nerve. The postoperative behavior of these rats indicates that hyperalgesia, allodynia and, possibly, spontaneous pain (or dysesthesia) were produced. Hyperalgesic responses to noxious radiant heat are typically evident on the second postoperative day and lasted for over 2 months. Hyperalgesic responses to chemogenic pain were also present. The presence of allodynia may be inferred from nocifensive responses evoked by standing on an innocuous, chilled metal floor or by innocuous mechanical stimulation (e.g., with von Frey filaments), and by the rats' persistence in holding the hind paw in a guarded position. The presence of spontaneous pain is suggested by a suppression of appetite and by the frequent occurrence of apparently spontaneous nocifensive responses. The affected hind paw is typically abnormally warm or cool in about one-third of the rats. About one-half of the rats develop grossly overgrown claws on the affected side. In compound efficacy models, test compound is typically delivered prior to stimulation and vehicle serves as control. Experiments with this animal model may advance understanding of the neural mechanisms of neuropathic pain disorders in humans. Bennett G J, Xie Y K, 1988 "A peripheral mononeuropathy in rat that produces disorders of pain sensation like those seen in man.," *Pain*, April; 33(1):87-107 (PMID: 2837713).

Chung Model of Neuropathic Pain

Since its introduction in 1992, the spinal nerve ligation (SNL) model of neuropathic pain has been widely used for various investigative works on neuropathic pain mechanisms as well as in screening tests for the development of new analgesic drugs. This model was developed by tightly ligating one (L5) or two (L5 and L6) segmental spinal nerves in the rat. The operation results in long-lasting behavioral signs of mechanical allodynia, heat hyperalgesia, cold allodynia, and ongoing pain. In the process of widespread usage, many different variations of the SNL model have been produced, either intentionally or unintentionally, by different investigators. Although the factors that cause these variations themselves are interesting and important topics to be studied, the pain mechanisms involved in these variations are likely different from the original model. The method for producing the spinal nerve ligation model that will minimally induce potential factors that may contribute to these variations is described in detail in Chung J M, Kim H K, and Chung K, "Segmental spinal nerve ligation model of neuropathic pain," *Methods Mol Med.;* 2004 99:35-45 (PMID: 15131327).

Chung Model in NHP

In a model of painful neuropathy in the primate (*Macaca fascicularis*), a neuropathic state is induced by tight ligation of the L7 spinal nerve, just distal to the L7 dorsal root ganglion. Sensory testing may be done on the ventral surface of the foot, a region that includes the L7 dermatome. Within 1 week following surgery, primates typically develop a marked sensitivity to mechanical stimulation (e.g., with von Frey hairs), indicating the presence of mechanical allodynia. Increased sensitivity to mechanical stimulation is sometimes also observed on the contralateral side. The threshold for withdrawal to a heat stimulus decreases, indicating the presence of heat hyperalgesia. Presentation of various cooling stimuli, such as acetone and cold water baths, indicates that cold allodynia also develops. Observed behavioral phenomena are similar to those seen in humans diagnosed with peripheral neuropathic pain. Thus, the model is useful for assessing a number of parameters relevant to human neuropathy and neuropathic pain disorders, and for evaluating the efficacy of drug candidates as treatments for related disorders. See, e.g., Carlton S M et al., "Behavioral manifestations of an experimental model for peripheral neuropathy produced by spinal nerve ligation in the primate," *Pain* 1994 February; 56(2):155-66 (PMID: 8008406).

Tactile Allodynia Assessment with Von Frey Filaments

The following quantitative allodynia assessment technique may be modified to measure tactile allodynia in any of the various animal models of neuropathic pain. The following summary is given by way of example and refers to a rat surgical neuropathy model wherein nocifensive behaviors are evoked by light touch to the paw. Employing von Frey hairs from 0.41 to 15.1 g, the percent response at each stimulus intensity may first be characterized. A smooth log-linear relationship is typically observed. Additionally or alternatively, a paradigm using stimulus oscillation around the response threshold may be employed, which allows more rapid, efficient measurements. Correlation coefficient between the two methods is typically high. In neuropathic rats, good intra- and inter-observer reproducibility is found for the up-down paradigm; some variability may be seen in normal rats, attributable to extensive testing. The fact that thresholds in a sizable group of neuropathic rats show insignificant variability over 20 days, and after 50 days, 61% still met strict neuropathy criteria (using survival analysis), indicates that threshold measurement using the up-down paradigm, in combination with the neuropathic pain model, represents a powerful tool for analyzing the effects of manipulations of the neuropathic pain state. See, e.g., Chaplan S R et al., "Quantitative assessment of tactile allodynia in the rat paw.," *J Neurosci Methods,* 1994 July: 53(0:55-63 (PMID: 7990513).

Hargreaves Method of Assessing Thermal Nociception

Alternatively, a method to measure cutaneous hyperalgesia to thermal stimulation in unrestrained animals has been described. The testing paradigm uses an automated detection of the behavioral end-point; repeated testing does not contribute to the development of the observed hyperalgesia. Carrageenan-induced inflammation results in significantly shorter paw withdrawal latencies as compared to saline-treated paws and these latency changes corresponded to a decreased thermal nociceptive threshold. This sensitive thermal method detects dose-related hyperalgesia and its blockade by test compounds and allows for the measurement of other behavioral parameters in addition to the nociceptive threshold. See, e.g., Hargreaves K, et al., "A new and sensitive method for measuring thermal nociception in cutaneous hyperalgesia," *Pain,* 1988 January; 32(1):77-88 (PMID: 3340425).

Inflammatory and Autoimmune Models

Contact Dermatitis and Related Disorders

Contact hypersensitivity is a simple delayed type hypersensitivity in vivo assay of cell-mediated immune function, which can be used to assess potential therapeutic efficacy in a number of disorders having an inflammatory and/or autoimmune component. Such diseases include contact dermatitis, atopic dermatitis, psoriasis, allergic dermatitis, and dermal irritation. Compounds may be topically applied, optionally in a topical formulation, or may be delivered by a non-topical (e.g., oral, IV, etc) route.

Murine Model

In one procedure, cutaneous exposure to exogenous haptens gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. Murine models also typically have the additional benefit of being economical to run. A suitable procedure is described in detail in Gaspari A A and Katz S I, "Contact Hypersensitivity," *Current Protocols in Immunology,* Unit 4.2, John Wiley & Sons, Inc. (1994). See also Grabbe S and Schwarz T, "Immunoregulatory mechanisms involved in elicitation of allergic contact hypersensitivity," *Immun. Today* 19 (1): 37-44 (1998).

Porcine Model

The choice of animal can be important in dematological studies intended to predict human response. For this reason, pigs and in particular minipigs are favored due to the similarities between human and pig skin (particularly follicular density). See, for example, an exemplary model in Bilski A J and Thomson DS, "Allergic contact dermatitis in the domestic pig. A new model for evaluating the topical anti-inflammatory activity of drugs and their formulations," *Br J Dermatol,* 1984 July; 111 Suppl 27:143 (PMID: 6743545).

Hairless Guinea Pig Model

Allergic and irritant contact reactions have also been evaluated in the recently identified hairless guinea pig, Crl:IAF(HA)BR, a mutant from the Hartley strain. The irritant contact dermatitis may be induced by croton oil, 2,4-dinitrochlorobenzene (DNCB), or anthralin. Both hairless and hairy guinea pigs develop similar reactions to these chemicals. Photoallergic contact sensitization may be also induced with tetrachlorosalicylanilide (TCSA), or with cyclophosphamide before sensitization with tribromosalicylanilide (TBS). Cutaneous changes are observed macro- and microscopically according to methods known in the art. Thus, hairless guinea pigs can be used as animal models for assessment of test compounds in the treatment of immunologic and nonimmunologic contact reactions and related disorders. See, e.g., Miyauchi H and Horio T, "A new animal model for contact dermatitis: the hairless guinea pig," *J Dermatol.* 1992 March; 19(3):140-5(PMID: 1640019).

Simple dermal irritation may also be studied in hairless guinea-pigs. In an exemplary model, test compounds are delivered in one or more topical formulations for 30 min daily exposure for 4 days. Scoring is performed daily; evaporimetry (total epidermal water loss (TEWL)), hydration and colorimetry are measured at baseline (day 0) in the middle and at the end of treatment. Test compounds are applied twice daily. See, e.g., Andersen F et al., "The hairless guinea-pig as a model for treatment of cumulative irritation in humans," *Skin Res Technol.* 2006 February; 12(1):60-7 (PMID: 16420540).

Psoriasis Murine Chimera Model

Additionally, the compounds disclosed herein can be tested in animal models for psoriasis-like diseases. Research into the cause and pathophysiological mechanisms underlying expression of psoriatric skin lesions has been hampered by lack of an appropriate animal model for this common and enigmatic cutaneous disease. One suitable model is the human skin/scid mouse chimera prepared as described by Nickoloff B J et al., "Severe combined immunodeficiency mouse and human psoriatic skin chimeras. Validation of a new animal model," Am J Pathol., 1995 March; 146(3): 580-8 (PMID: 7887440). The methods described therein characterize normal skin, pre-psoriatic skin, and psoriatic plaque skin samples transplanted onto severe combined immunodeficiency mice. Either normal, prepsoriatic, or psoriatic plaque keratome skin samples are transplanted onto severe combined immunodeficiency mice reliably with high rates of graft survival (>85%) and with reproducible changes consistently observed over prolonged periods of engraftment. After transplantation, by clinical assessment and routine light microscopy, normal skin remains essentially normal whereas pre-psoriatic skin became thicker, and psoriatic plaque skin retains its characteristic plaque-type elevation and scale. By using a panel of antibodies and immunohistochemical analysis, the overall phenotype of human cell types (including immunocytes) that persisted in the transplanted skin was remarkably similar to the immunophenotype of pretransplanted skin samples. Additionally, clearly recognized interface zones between human and murine skin within the epidermal and dermal compartments can be identified by routine microscopy and immunostaining, with focal areas of chimerism. The many similarities between pre- and post-transplanted human samples of normal and psoriatic skin that are grafted onto severe combined immunodeficiency mice make this animal model appropriate for use in evaluating test compounds for efficacy in treating psoriasis and related disorders.

Psoriasis Murine scid/scid Model

Alternatively, the compounds disclosed herein can be tested in the scid/scid mouse model described by Schön M P et al., "Murine psoriasis-like disorder induced by naive CD4+ T cells," *Nat Med.,* 1997 February; 3(2):183-8 (PMID: 9018237). In this model, reconstitution of scid/scid mice with minor histocompatibility mismatched naive CD4+T lymphocytes results in skin alterations that strikingly resemble human psoriasis clinically, histopathologically and in cytokine expression.

Asthma

Compounds may additionally be evaluated for efficacy in the treatment of asthma and related pulmonary disorders. In one murine model of asthma, wild-type control [C57BL/6J, (+/+)] and ICAM-1 (intercellular adhesion molecule-1) knockout [C57BL/6J-ICAM-1, (−/−)] mice are sensitized to ovalbumin (OVA), and challenged with OVA delivered by aerosol (OVA-OVA) to induce a phenotype consistent with an asthmatic response. Bronchial responsiveness to methacholine and counts of cell numbers and measurements of eosinophil content and cytokine levels in bronchoalveolar lavage fluid (BALF) may be measured. Additionally, lymphocyte proliferation in response to antigen, eosinophil migration into the airways, and the development of airway hyperreactivity (AHR) in allergen-sensitized and -challenged mice may all be measures in vivo or ex vivio according to methods known in the art. See Wolyniec W W et al., "Reduction of antigen-induced airway hyperreactivity and eosinophilia in ICAM-1-deficient mice," *Am J Respir Cell Mol Biol.,* 1998 June; 18(6):777-85 (PMID: 9618382).

Inflammatory Bowel Disease, Crohn's Disease, and Ulcerative Colitis

The compounds disclosed herein can also be evaluated for activity in animal models of inflammatory bowel disease, Crohn's disease, and ulcerative colitis. The protocol described by Scheiffele F, Fuss I J, "Induction of TNBS colitis in mice," *Curr Protoc Immunol,* 2002 August; Chapter 15:Unit 15.19 (PMID: 18432874), is one of several that have been used to study the immunopathogenesis of these diseases. The model employs the use of 2,4,6-trinitrobenzenesulfonic acid (TNBS), which induces severe colonic inflammation when administered intrarectally in SJL/J mice. The colitis which results from this procedure presents clinical and histopathological findings that resemble those seen in Crohn's disease. Scheifflele and Fuss discuss the critical parameters needed for successful induction of TNBS-colitis as well methods for monitoring and grading disease levels, and give a support protocol for isolating lamina propria mononuclear cells from mouse colons. See also Morris G P et al. "Hapten-induced model of chronic inflammation and ulceration in the rat colon," *Gastroenterology,* 1989 March; 96(3):795-803 (PMID: 2914642), describing the original rat model of chronic colonic inflammation by the intraluminal instillation of a solution containing a "barrier breaker" (e.g., 0.25 ml of 50% ethanol) and a hapten (e.g., TNBS, 5-30 mg) At a dose of 30 mg, trinitrobenzenesulfonic acid/ethanol-induced ulceration and marked thickening of the bowel wall persisted for at least 8 weeks. Histologically, the inflammatory response included mucosal and submucosal infiltration by polymorphonuclear leukocytes, macrophages, lymphocytes, connective tissue mast cells, and fibroblasts. Granulomas (3 wk after induction of inflammation), Langhan's-type giant cells, segmental ulceration and inflammation. The characteristics and relatively long duration of inflammation and ulceration induced in these models afford an opportunity to study the pathophysiology of colonic inflammatory disease in a specifically controlled fashion, and to evaluate new treatments potentially applicable to inflammatory bowel disease in humans.

Exemplary Oral Pharmaceutical Formulations

The following are examples of compositions which may be used to orally deliver compounds disclosed herein as a capsule.

A solid form of a compound of Formula VI may be passed through one or more sieve screens to produce a consistent particle size. Excipients, too, may be passed through a sieve. Appropriate weights of compounds, sufficient to achieve the target dosage per capsule, may be measured and added to a mixing container or apparatus, and the blend is then mixed until uniform. Blend uniformity may be done by, for example, sampling 3 points within the container (top, middle, and bottom) and testing each sample for potency. A test result of 95-105% of target, with an RSD of 5%, would be considered ideal; optionally, additional blend time may be allowed to achieve a uniform blend. Upon acceptable blend uniformity results, a measured aliquot of this stock formulation may be separated to manufacture the lower strengths. Magnesium stearate may be passed through a sieve, collected, weighed, added to the blender as a lubricant, and mixed until dispersed. The final blend is weighed and reconciled. Capsules may then be opened and blended materials flood fed into the body of the capsules using a spatula. Capsules in trays may be tamped to settle the blend in each capsule to assure uniform target fill weight, then sealed by combining the filled bodies with the caps.

COMPOSITION EXAMPLES

In the composition examples below, target dosages may be adjusted to account for the weight of counterions and/or solvates if given as a salt or solvated polymorph thereof. In such a case the weight of the other excipients, typically the filler, is reduced. For example, with the dihydrochloride monohydrate MGBG salt, a correction factor of 1.49 is used (e.g., 360 mg of the salt to give 240.8 mg of the free base).

Example 1A 300 mg Capsule

Total fill weight of capsule is 500 mg, not including capsule weight. Target compound dosage is 300 mg per capsule

| Ingredient | Quantity per Capsule, mg |
|---|---|
| MGBG | 300.00 |
| Lactose monohydrate | 179.00 |
| Silicon dioxide | 3.00 |
| Crospovidone | 15.00 |
| Magnesium stearate (vegetable grade) | 3.00 |

Example 1B 150 mg Capsule

Total fill weight of capsule is 300 mg, not including capsule weight. Target compound dosage is 150 mg per capsule

| Ingredient | Quantity per Capsule, mg |
|---|---|
| MGBG | 150 |
| Microcrystalline cellulose (MCC) | 147 |
| Magnesium stearate (vegetable grade) | 3 |

MGBG-Fingolimod Combination Examples

Total fill weight of capsule is given below in mg, not including capsule weight.

| Ingredient | 2A | 2B | 2C | 2D | 2E | 2F |
|---|---|---|---|---|---|---|
| MGBG | 350 mg | 300 mg | 250 mg | 175 mg | 150 mg | 125 mg |
| Fingolimod | 0.5 mg | 0.5 mg | 0.5 mg | 0.25 mg | 0.25 mg | 0.25 mg |
| Mannitol, lactose, and/or microcrystalline cellulose (MCC) | 146.5 mg | 196.5 mg | 246.5 mg | 121.75 mg | 146.75 mg | 171.75 mg |
| Magnesium stearate (vegetable grade) | 3 mg | 3 mg | 3 mg | 3 mg | 3 mg | 3 mg |
| TOTAL FILL WEIGHT | 500 mg | 500 mg | 500 mg | 300 mg | 300 mg | 300 mg |

All references cited herein are incorporated by reference as if written herein in their entireties. From the foregoing description, one skilled in the art can easily ascertain the essential characteristics of this invention, and without departing from the spirit and scope thereof, can make various changes and modifications of the invention to adapt it to various usages and conditions. The invention disclosed herein provides for embodiments in which each of the embodiments above is combined with one or more of the other non-contradictory embodiments, such that the resulting embodiment includes the two or more recited elements and/or limitations.

What is claimed is:

1. A method of prevention of progression of a multiple sclerosis in a patient, comprising the administration of methylglyoxal bis(guanylhydrazone) (MGBG) to the patient in need thereof.

2. The method as recited in claim 1, wherein the symptoms in a relapse of multiple sclerosis are decreased.

3. The method as recited in claim 1, wherein the symptoms of multiple sclerosis are prevented to a clinically significant or detectable level.

4. The method as recited in claim 1, wherein the progression to an increased occurrence or severity of flare-ups of multiple sclerosis is prevented, the flare-up being characterized by increased demyelination or a reduced capacity for movement over time.

5. The method as recited in claim 1, wherein the administration of MGBG is oral.

6. The method as recited in claim 2, wherein MGBG is dosed at 20 mg/day to 400 mg/day.

7. The method as recited in claim 6, wherein administration occurs concomitant with a reduced incidence of at least one side effect chosen from cytopenia, nephrotoxicity, hepatotoxicity, cardiotoxicity, teratogenicity, decreased pulmonary function, macular edema, peripheral neuropathy, severe skin reactions, increased risk of infections (including latent bacterial and viral), impairment of innate immunity, impairment of adaptive immunity, and flushing, as compared to interferon beta-1a, interferon beta-1b, glatiramer acetate, peginterferon beta-1a, daclizumab, teriflunomide, fingolimod, dimethyl fumarate, alemtuzumab, mitoxantrone, or natalizumab.

8. The method as recited in claim 7, additionally comprising the administration of an agent chosen from interferon beta-1a, interferon beta-1b, glatiramer acetate, mitoxantrone, natalizumab, fingolimod, laquinimod, dimethyl fumarate, and teriflunomide.

9. The method as recited in claim 8, wherein the agent is fingolimod.

10. The method as recited in claim 9, wherein fingolimod is dosed at 0.5 mg per day.

11. The method as recited in claim 9, wherein fingolimod is dosed at less than 0.5 mg per day.

12. The method as recited in claim 9, wherein fingolimod is dosed at 0.25 mg per day.

13. The method as recited in claim 7, wherein administration occurs concomitant with a reduced incidence of at least one side effect chosen from cytopenia, nephrotoxicity, hepatotoxicity, cardiotoxicity, and teratogenicity.

14. The method as recited in claim 13, wherein the cytopenia is chosen from lymphopenia and neutropenia.

15. The method as recited in claim 7, wherein administration occurs concomitant with a reduced incidence of at least two side effects chosen from cytopenia, nephrotoxicity, hepatotoxicity, cardiotoxicity, and teratogenicity.

16. The method as recited in claim 15, wherein the cytopenia is chosen from lymphopenia and neutropenia.

17. The method as recited in claim 15, wherein administration occurs concomitant with a reduced incidence of cytopenia, nephrotoxicity, and hepatotoxicity.

18. The method as recited in claim 17, wherein the cytopenia is chosen from lymphopenia and neutropenia.

19. The method as recited in claim 17, wherein administration additionally occurs concomitant with a reduced incidence of cardiotoxicity, and teratogenicity.

* * * * *